United States Patent [19]

Chambers et al.

[11] Patent Number: 5,633,258

[45] Date of Patent: May 27, 1997

[54] PYRIDINE COMPOUNDS FOR TREATING LEUKOTRIENE-RELATED DISEASES

[75] Inventors: Pamela A. Chambers, King of Prussia; Robert A. Daines, Lansdale; Dalia R. Jakas, Norristown; William D. Kingsbury, Wayne; Israil Pendrak, Norristown, all of Pa.

[73] Assignee: SmithKline Beecham Corporation, Philadelphia, Pa.

[21] Appl. No.: 439,537

[22] Filed: May 11, 1995

Related U.S. Application Data

[63] Continuation of Ser. No. 211,063, Jul. 18, 1994, abandoned.
[51] Int. Cl.$^6$ .......... A61K 31/44; C07D 401/12; C07D 213/64; C07D 213/65
[52] U.S. Cl. .......... 514/277; 514/336; 514/357; 546/314; 546/326; 546/330; 546/334; 546/335; 546/340; 546/342
[58] Field of Search .......... 546/314, 326, 546/330, 334, 335, 340, 342, 268.4; 514/277, 357, 336

[56] References Cited

U.S. PATENT DOCUMENTS 5,109,009 4/1992 Nielsen et al. .......... 514/311

OTHER PUBLICATIONS

Chem Abstracts, vol. 116, (23), abst. No. 235,440w, Jun. 8, 1992.

Chem. Abstracts, vol. 120(21) Abst. No. 270,117a, May 23, 1994.

Primary Examiner—Alan L. Rotman
Attorney, Agent, or Firm—James M. Kanagy; Stephen Venetianer; Edward T. Lentz

[57] ABSTRACT

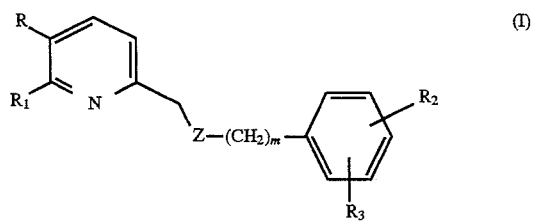

This invention relates to compounds of formula (I) which are useful as leukotriene antagonists.

4 Claims, No Drawings

PYRIDINE COMPOUNDS FOR TREATING LEUKOTRIENE-RELATED DISEASES

This is a continuation of application Ser. No. 08/211,063, filed Jul. 18, 1994, abandoned.

SCOPE OF THE INVENTION

This invention relates to certain compounds containing a substituted pyridyl group linked to a substituted phenyl group by an alkyl or heteroatom-containing tether and their use for treating diseases arising from or related to leukotrienes, particularly leukotriene $B_4$. As such their utility lies in antagonizing the effects of leukotrienes.

BACKGROUND OF THE INVENTION

The family of bioactive lipids known as the leukotrienes exert pharmacological effects on respiratory, cardiovascular, and gastrointestinal systems. The leukotrienes are generally divided into two sub-classes, the peptidoleukotrienes (leukotrienes $C_4$, $D_4$ and $E_4$) and the dihydroxyleukotrienes (leukotriene $B_4$). This invention is primarily concerned with the hydroxyleukotrienes (LTB) but is not limited to this specific group of leukotrienes.

Leukotrienes are critically involved in mediating many types of cardiovascular, pulmonary, dermatological, renal, allergic, and inflammatory diseases including asthma, adult respiratory distress syndrome, cystic fibrosis, psoriasis, and inflammatory bowel disease.

$LTB_4$ has been established as an inflammatory mediator in vivo. It has also been associated with airway hyper-responsiveness in the dog as well as being found in increased levels in lung lavages from humans with severe pulmonary dysfunction.

By antagonizing the effects of $LTB_4$, or other pharmacologically active mediators at the end organ, for example airway smooth muscle, the compounds and pharmaceutical compositions of the present invention are valuable in the treatment of diseases in subjects, including human or animals, in which leukotrienes are a factor.

SUMMARY OF THE INVENTION

This invention relates to novel benzylsulfides of formula 1

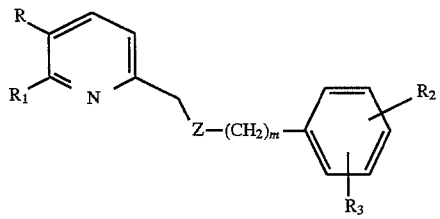

I or an N-oxide, or a pharmaceutically acceptable salt where

Z is O, NH, $NCH_3$ or $S(O)_q$ where q is 0, 1 or 2, m is 0–5;

R is $C_1$ to $C_{20}$-aliphatic, unsubstituted or substituted phenyl $C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O—, or R is unsubsfituted or substituted phenyl $C_1$ to $C_{10}$-aliphatic-O— where substituted phenyl has one or more radicals selected from the group consisting of lower alkoxy, lower alkyl, trihalomethyl, and halo;

$R_1$ is —($C_1$ to $C_5$ aliphatic)$R_4$, —($C_1$ to $C_5$ aliphatic)CHO, —($C_1$ to $C_5$ aliphatic)$CH_2OR_8$, —$R_4$, —$CH_2OH$, or CHO;

$R_2$ is H, halo, lower alkyl, lower alkoxy, —CN, —$(CH_2)_n R_4$, —$CH(NH_2)(R_4)$, or —$(CH_2)_n R_9$ where n is 0–5 and where $R_9$ is —$N(R_7)_2$ where each $R_7$ is independently H, or an aliphatic group of 1 to 10 carbon atoms, or acyl of 1–6 carbon atoms, or a cycloalkyl-$(CH_2)_n$— group of 4 to 10 carbons where n is 0–3, or both $R_7$ groups form a ring having 4 to 6 carbons; or $R_3$ is hydrogen, lower alkyl, lower alkoxy, halo, —CN, $R_4$, $NHCONH_2$, or OH;

each $R_4$ group is independently —$COR_5$ where $R_5$ is —OH, a pharmaceutically acceptable ester-forming group —$OR_6$, or —OX where X is a pharmaceutically acceptable cation, or $R_5$ is —$N(R_7)_2$ where each $R_7$ is independently H, or an aliphatic group of 1 to 10 carbon atoms, or a cycloalkyl-$(CH_2)_n$— group of 4 to 10 carbons where n is 0–3, or both $R_7$ groups form a ring having 4 to 6 carbons, or $R_4$ is a sulfonamide, or an amide, or tetrazol-5-yl; and $R_8$ is hydrogen, $C_1$ to $C_6$ alkyl, or $C_1$ to $C_6$-acyl, excluding those compounds where $R_2$ and $R_3$ are other than hydrogen and are substituted in the 2 and 6 positions.

In another aspect, this invention covers pharmaceutical compositions containing the instant compounds and a pharmaceutically acceptable excipient.

Treatment of diseases related to or caused by leukotrienes, particularly $LTB_4$, or related pharmacologically active mediators at the end organ are within the scope of this invention. This treatment can be effected by administering one or more of the compounds of formula I alone or in combination with a pharmaceutically acceptable excipient.

Processes for making these compounds are also included in the scope of this invention, which processes comprise:

a) forming a salt, or b) hydrolyzing an ester to give a salt or acid;

c) forming an ester, d) forming an amide;

e) oxidizing a thio ether, f) forming a compound of formula I by treating a 6-halomethylpyridyl compound with tha appropriate mercaptobenzoate or hydroxybenzoate.

DETAILED DESCRIPTION OF THE INVENTION

The following definitions are used in describing this invention and setting out what the inventors believe to be their invention herein.

"Aliphatic" is intended to include saturated and unsaturated radicals. This includes normal and branched chains, saturated or mono or poly unsaturated chains where both double and triple bonds may be present in any combination. The phrase "lower alkyl" means an alkyl group of 1 to 6 carbon atoms in any isomeric form, but particularly the normal or linear form. "Lower alkoxy" means the group lower alkyl-O—. "Halo" means fluoro, chloro, bromo or iodo. "Acyl" means the radical having a terminal carbonyl carbon.

When reference is made to a substituted phenyl ring, it is meant that the ring can be substituted with one or more of the named substituents as may be compatible with chemical synthesis. Multiple substituents may be the same or different, such as where there are three chloro groups, or a combination of chloro and alkyl groups and further where this latter combination may have different alkyl radicals in the chloro/alkyl substituent pattern.

The phrase "a pharmaceutically acceptable ester-forming group" in $R_2$ and $R_3$ covers all esters which can be made from the acid function(s) which may be present in these compounds. The resultant esters will be ones which are acceptable in its application to a pharmaceutical use. By that it is meant that the mono or diesters will retain the biological activity of the parent compound and will not have an untoward or deleterious effect in their application and use in treating diseases. Such esters are, for example, those formed with one of the following radicals: $C_1$ to $C_6$ alkyl, phenyl $C_1$–$C_6$alkyl, cycloalkyl, aryl, arylalkyl, alkylaryl, alkylarylalkyl, aminoalkyl, indanyl, pivaloyloxymethyl, acetoxymethyl, propionyloxymethyl, glycyloxymethyl, phenylglycyloxymethyl, or thienylglycyloxymethyl. The most preferred ester-forming radicals are those where $R_3$ is alkyl, particularly alkyl of 1 to 10 carbons, (ie $CH_3$—$(CH_2)_n$— where n is 0–9), or phenyl-$(CH_2)_n$— where n is 0–4.

When $R_2$ is referred to as being an amine, that includes the radical —$NH_2$ and mono- or dialkylate derivatives of this —$NH_2$ radical. Preferred alkylated amines are the mono- or disubstituted amines having 1 to 6 carbons. When $R_2$ is referred to as being an amide, that includes all acylate derivatives of the $NH_2$ radical. The preferred amides are those having 1 to 6 carbons.

Where there is an acid group, amides may be formed. The most preferred amides are those where —$R_6$ is hydrogen or alkyl of 1 to 6 carbon atoms. Particularly preferred is the diethylamide or dimethylamide.

Pharmaceutically acceptable salts of the instant compounds are intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner, in a suitable solvent. The parent compound in a suitable solvent is reacted with an excess of an organic or inorganic acid, in the case of acid addition salts, or an excess of organic or inorganic base in the case where $R_4$ is OH.

N-oxides may also be prepared by means of selected oxidizing agents. These oxides are useful as intermediates in preparing the compounds of formula I and have useful pharmaceutical activity in and of themselves. Hence one can administer the N-oxides of formula I to a subject who is susceptible to or is suffering from a disease related to or caused by $LTB_4$ or similar leukotrienes.

If by some combination of substituents, a chiral center is created or another form of an isomeric center is created in a compound of this invention, all forms of such isomer(s) are intended to be covered herein. These compounds may be used as a racemic mixture or the racemates may be separated and the individual enantiomer used alone. Olefins may have the cis or trans configuration (E or Z); either are useful in the practice of this invention.

As leukotriene antagonists, these compounds can be used in treating a variety of disease assoicated with or attributing their origin or affect to leukotrienes, particularly $LTB_4$. Thus it is expected that these compounds can be used to treat allergic diseases such of a pulmonary and non-pulmonary nature. For example these compounds will be useful in antigen-induced anaphylaxis; for treating asthma and allergic rhinitis; psoriasis, or irritable bowel disease; ocular diseases such as uveitis, and allergic conjunctivitis.

The preferred compounds are those where Z is O or $S(O)_q$; m is 0–3; n is 0–2; R is alkoxy of 8 to 15 carbon atoms or unsubstituted or substitutited pheny-$C_1$ to $C_{10}$-aliphatic-O—; and $R_1$ is —($C_1$ to $C_5$ aliphatic)$R_4$ or —($C_1$ to $C_5$-aliphatic)$CH_2OR_8$. The more preferred compounds of this invention are those where $R_1$ is $R_4CH=CH$— and $R_2$ is —$COR_5$ or —$NHSO_2CF_3$. Another set of preferred compounds are the anilines, those where $R_2$ is $N(R_7)_2$, particularly where $R_7$ is hydrogen. A third set of preferred compounds are those where both $R_2$ and $R_3$ are hydrogen.

The most preferred compounds are:

1-fluoro-3-[2-thia-3-[2-(E-2-carboxyethenyl)-3-[4-(4-methoxyphenyl)butyloxy]-6-pyridyl]propyl]benzene, lithium salt;

3-[2-thia-3-[2-(E-2-carboxyethenyl)-3-[4-(4-methoxyphenyl)butyloxy]-6-pyridyl]propyl]benzene, lithium salt;

3-[2-thia-3-[2-(2-carboxyethanyl)-3-[4-(4-methoxyphenyl)butyloxy]-6-pyridyl]propyl]benzene, lithium salt;

2-[2-thia-3-[2-(2-carboxyethenyl)-3-[4-(4-methoxyphenyl)butyloxy]-6-pyridyl]ethyl]benzene, lithium salt;

1-fluoro-4-[2-thia-3-[2-(2-carboxyethanyl)-3-[4-(4-methoxyphenyl)butyloxy]-6-pyridyl]propyl]benzene, lithium salt;

1-fluoro-4-[2-thia-3-[2-(E-2-carboxyethenyl)-3-[4-(4-methoxyphenyl)butyloxy]-6-pyridyl]propyl]benzene, lithium salt;

3-[1-thia-2-[2-(E-2-carboxyethenyl)-3-[8-(4-methoxyphenyl)octyloxy]-6-pyridyl]ethyl]benzoic acid, 3-[1-oxythia-2-[2-(E-2-carboxyethenyl)-3-[8-(4-methoxyphenyl)octyloxy]-6-pyridyl]ethyl]benzoic acid, 3-[1-thia-2-[2-(E-2-carboxyethenyl)-3-dodecyloxy-6-pyridyl]ethyl]benzoic acid, 3-[1-oxythia-2-[2-(E-2-carboxyethenyl)-3-dodecyloxy-6-pyridyl]ethyl]benzoic acid, 3-[1-dioxythia-2-[2-(E-2-carboxyethenyl)-3-dodecyloxy-6-pyridyl]ethyl]benzoic acid, 2-[1-oxythia-2-[2-(E-2-carboxyethenyl)-3-dodecyloxy-6-pyridyl]ethyl]benzoic acid, lithium salt N-[3-[1-thia-2-[2-(E-2-carboxyethenyl)-3-dodecyloxy-6-pyridyl]ethyl]phenyl]trifluoromethanesulfonamide, N-[3-[1-thia-2-[2-(E-2-carboxyethenyl)-3-(8-(4-methoxyphenyl)octyloxy)-6-pyridyl]ethyl]phenyl] trifluoromethanesulfonamide, N-[3-[1-oxythia-2-[2-(E-2-carboxyethenyl)-3-(8-(4-methoxyphenyl)octyloxy)-6-pyridyl]ethyl]phenyl]-trifluoromethanesulfonamide, N-[3-[1-oxythia-2-[2-(E-2-carboxyethenyl)-3-(8-(4-methoxyphenyl)octyloxy)-6-pyridyl]ethyl]phenyl]-phenylsulfonamide, N-[3-[1-thia-2-[2-(E-2-carboxyethenyl)-3-(8-(4-methoxyphenyl)octyloxy)-6-pyridyl]ethyl]-phenyl] phenylsulfonamide, 3-[1-oxa-2-[2-(E-2-carboxyethenyl)-3-dodecyloxy-6-pyridyl]ethyl]benzoic acid, 3-[1-oxa-2-[2-(E-2-carboxyethenyl)-3-[8-(4-methoxyphenyl)octyloxy]-6-pyridyl]ethyl]benzoic acid, 3-[1-oxa-2-[2-(E-2-carboxyethenyl)-3-[8-(4-methoxyphenyl)octan-1-yl]-6-pyridyl]ethyl]benzoic acid, 4-[2-thia-3-[2-(E-2-carboxyethenyl)-3-[8-(4-methoxyphenyl)octyloxy]-6-pyridyl]propyl]benzoic acid, 4-[2-thia-3-[2-(E-2-carboxyethenyl)-3-[4-(4-methoxyphenyl)butyloxy]-6-pyridyl]propyl]benzoic acid, 3-[2-thia-3-[2-(E-2-carboxyethenyl)-3-[8-(4-methoxyphenyl)octyloxy]-6-pyridyl]propyl]benzoic acid, 3-[2-thia-3-[2-(E-2-carboxyethenyl)-3-[4-(4-methoxyphenyl)butyloxy]-6-pyridyl]propyl]benzoic acid, 3-[2-thia-3-[2-(2-carboxyethanyl)-3-[8-(4-methoxyphenyl)octyloxy]-6-pyridyl]propyl]benzoic acid, 3-[2-thia-3-[2-(E-2-carboxyethenyl)-3-(8-(4-methoxyphenyl)octyloxy)-6-pyridyl]propyl]-N,N,-dimethylbenzamide, lithium salt 3-[2-thia-3-[2-(E-2-carboxyethenyl)-3-(4-(4-methoxyphenyl)butyloxy)-6-pyridyl]propyl]-N,N-dimethylbenzamide, lithium salt, 3-[2-thia-3-[2-(E-2-carboxyethenyl)-3-[4-phenylbutyloxy]-6-pyridyl]propyl]benzoic acid, 3-[2-thia-3-[2-(E-2-carboxyethenyl)-3-[8-phenyloctyloxy]-6-pyridyl]propyl]benzoic acid, 3-[2-thia-3-[2-(2-carboxyethanyl)-3-[4-(4-methoxyphenyl)butyloxy]-6-pyridyl]propyl]benzoic acid, 4-[2-thia-3-[2-(E-2-carboxyethenyl)-3-[8-(4-methoxyphenyl)octyloxy)-6-pyridyl]propyl]phenylacetic acid, 4-[2-oxythia-3-[2-(E-2-carboxyethenyl)-3-[8-(4-methoxyphenyl)octyloxy]-6-pyridyl]propyl]benzoic acid, 3-[2-oxythia-3-[2-(E-2-carboxyethenyl)-3-[8-(4-methoxyphenyl)octyloxy]-6-pyridyl]propyl]benzoic acid, 4-[2-oxythia-3-[2-(E-2-carboxyethenyl)-3-[8-(4-methoxyphenyl)octyloxy]-6-pyridyl]propyl]phenylacetic acid, 3-[2-dioxythia-3-[2-(E-2-carboxyethenyl)-3-[8-(4-methoxyphenyl)octyloxy]-6-pyridyl]propyl]benzoic acid, 5-[3-[2-thia-3-[2-(E-2-carboxyethenyl)-3-[8-(4-methoxyphenyl)octyloxy]-6-pyridyl]propyl]phenyl]tetrazole 3-[1-oxa-2-[2-(E-2-carboxyethenyl)-3-(8-(4-methoxyphenyl)octyloxy)-6-pyridyl]ethyl]aniline, 5-carboxy-3-[1-oxa-2-[2-(E-2-carboxyethenyl)-3-(8-(4-methoxyphenyl)octyloxy)-6-pyridyl]ethyl]aniline, 3-[1-thia-2-[2-(E-2-carboxyethenyl)-3-(8-(4-methoxyphenyl)octyloxy)-6-pyridyl]ethyl]aniline, 3-[1-thia-2-[2-(E-2-carboxyethenyl)-3-(8-(4-trifluoromethylphenyl)octyloxy)-6-pyridyl]ethyl]aniline, 3-[1-oxythia-2-[2-(E-2-carboxyethenyl)-3-(8-(4-trifluoromethylphenyl)octyloxy)-6-pyridyl]ethyl]aniline, lithium salt 3-[1-thia-2-[2-(E-2-carboxyethenyl)-3-(8-phenyloctyloxy)-6-pyridyl]ethyl]aniline, lithium salt 3-[1-oxythia-2-[2-(E-2-carboxyethenyl)-3-(8-(4-fluorophenyl)octyloxy)-6-pyridyl]ethyl]aniline, 3-[1-oxythia-2-[2-(E-2-carboxyethenyl)-3-(8-phenyl)octyloxy)-6-pyridyl]ethyl]aniline, 3-[1-thia-2-[2-(E-2-carboxyethenyl)-3-(8-(4-methoxyphenyl)octyloxy)-6-pyridyl]ethyl]-N,N-dimethylaniline, 3-[1-thia-2-[2-(E-2-carboxyethenyl)-3-(4-(4-methoxyphenyl)butyloxy)-6-pyridyl]ethyl]aniline, lithium salt 3-[1-oxythia-2-[2-(E-2-carboxyethenyl)-3-(4-(4-methoxyphenyl)butyloxy)-6-pyridyl]ethyl]aniline, lithium salt 3-[1-dioxythia-2-[2-(E-2-carboxyethenyl)-3-(4-(4-methoxyphenyl)butyloxy)-6-pyridyl]ethyl]aniline, lithium salt 3-[2-thia-3-[2-(E-2-carboxyethenyl)-3-(8-(4-methoxyphenyl)octyloxy)-6-pyridyl]propyl]-N,N-dimethylaniline, 3-[1-oxythia-2-[2-(E-2-carboxyethenyl)-3-(8-(4-methoxyphenyl)octyloxy)-6-pyridyl]ethyl]aniline, 3-[1-oxythia-2-[2-(E-2-carboxyethenyl)-3-(8-(4-methoxyphenyl)octyloxy)-6-pyridyl]ethyl]-N,N-dimethylaniline, 3-[1-dioxythia-2-[2-(E-2-carboxyethenyl)-3-(8-(4-methoxyphenyl)octyloxy)-6-pyridyl]ethyl]aniline, (E)-lithium 3-[3-[4-(4-methoxyphenyl)butyloxy]-6-[(2-phenylthio)methyl]-2-pyridinyl]-2-propenoate, (E)-lithium 3-[3-[4-(4-methoxyphenyl)butyloxy]-6-[(3,4-dichlorophenylthio)methyl]-2-pyridinyl]-2-propenoate, (E)-lithium 3-[3-[4-(4-methoxyphenyl)butyloxy]-6-[(4-chlorophenylthio)methyl]-2-pyridinyl]-2-propenoate, (E)-sodium 3-[3-[4-(4-methoxyphenyl)butyloxy]-6-[(4-fluorophenylthio)methyl]-2-pyridinyl]-2-propenoate, (E) lithium 3-[3-[4-(4-methoxyphenyl)butyloxy]-6-[(2-chlorophenylthio)methyl]-2-pyridinyl]-2-propenoate, (E)-sodium 3-[3-[4-(4-methoxyphenyl)butyloxy]-6-[(2-chlorobenzylthio)methyl]-2-pyridinyl]-2-propenoate, (E)-sodium 3-[3-[4-(4-methoxyphenyl)butyloxyl-6-[(2-methylpnenylthio)methyl]-2-pyridinyl]-2-propenoate.

(E)-sodium 3-[3-[4-(4-methoxyphenyl)butyloxy]-6-[(3-chlorophenylthio)methyl]-2-pyridinyl]-2-propeonate, (E)-sodium 3-[3-[4-(4-methoxyphenyl)butyloxy]-6-[(2-methoxyphenylthio)methyl]-2-pyridinyl]-2-propenoate, (E)-sodium 3-[3-[4-(4-methoxyphenyl)butyloxyl-6-[(2,4-dichlorophenylthio)methyl]-2-pyridinyl]-2-propenoate, (E)-sodium 3-[3-[4-(4-methoxyphenyl)butyloxy]-6-[(2-bromophenylthio)methyl]-2-pyridinyl]-2-propenoate, (E)-sodium 3-[3-[4-(4-methoxyphenyl)butyloxy]-6-[(2-methylphenylthio)methyl]-2-pyridinyl]-2-propenoate.

SYNTHESIS

There are several methods for preparing these compounds. One generic process comprises preparing a 6-(halomethyl)pyridyl adduct and then condensing this fragment with the appropriate mercaptan or alcohol to make compounds where Z is sulfur or oxygen. Usually, functional groups such as acid groups will be protected; any acid group may be derivatized in some manner to render it unreactive. After the condensation reaction, protecting groups may be removed to provide the parent functionality, e.g. an acid. Further modification of these reactive groups can then be carried out, such as forming a salt, an amide, an ester or the like. Sulfonamides are prepared from the corresponding amines by literature methods. Tetrazoles are prepared from the corresponding acid halide, e.g., the acid chloride, by literature methods.

More specific illustrations of chemistry for making these compounds is provided in the following reaction schemes. Scheme I outlines a means for making a substituted phenylalkyl tail which is R.

Scheme I

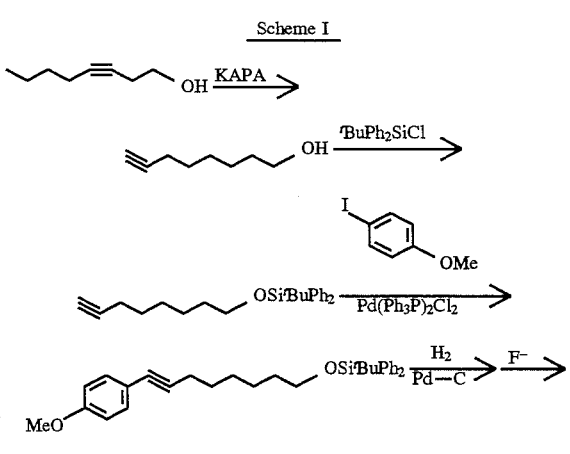

Scheme I -continued

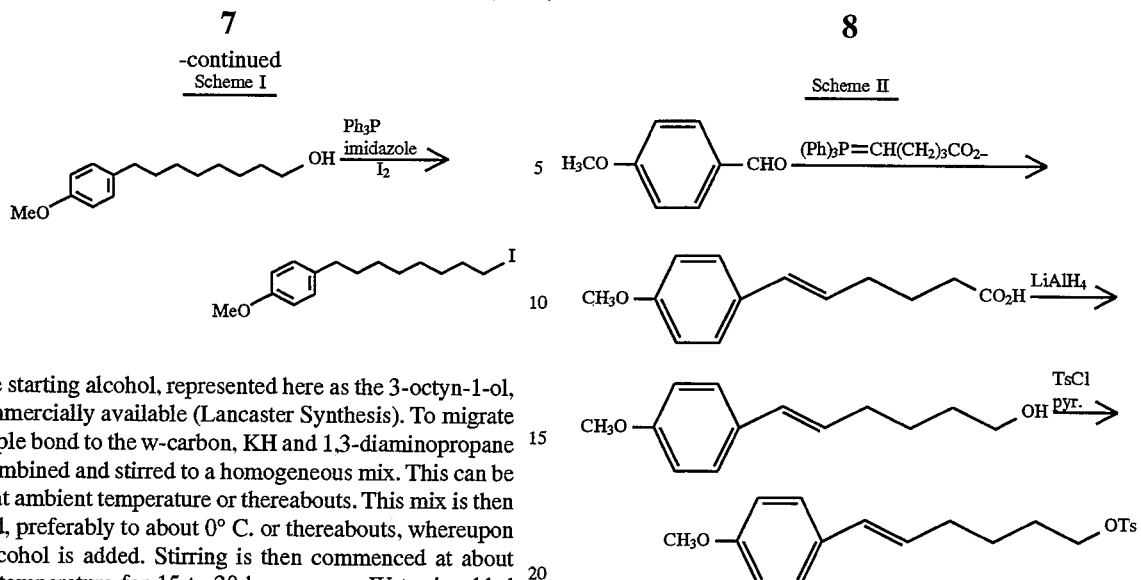

The starting alcohol, represented here as the 3-octyn-1-ol, is commercially available (Lancaster Synthesis). To migrate the triple bond to the w-carbon, KH and 1,3-diaminopropane are combined and stirred to a homogeneous mix. This can be done at ambient temperature or thereabouts. This mix is then cooled, preferably to about 0° C. or thereabouts, whereupon the alcohol is added. Stirring is then commenced at about room temperature for 15 to 20 hours or so. Water is added to quench the reaction and the product is recovered.

Protecting the alcohol is accomplished by forming a silyl ether illustrated here as the t-butyldiphenylsilyl ether. Other silyl ethers could be used. The alcohol is dissolved in a polar solvent, for example dimethylformamide, and imidazole is added followed by the desired silane. All this is carried out under an inert atmosphere such as argon. Ambient temperature is acceptable for effecting the reaction.

Adding the phenyl group is done in a dry environment using an amine for a solvent and an inert atmosphere. To a flask containing a solvent such as triethylamine under argon is added the silylether followed by a halophenyl compound, eg. iodoanisole, a palladium catalyst $(Ph_3P)_2PdCl_2$ and CuI, both of the latter in catalytic amounts. Heat is used to effect the reaction, usually a temperature of up to about 50° C. will be sufficient. Two or more hours, up to six but often about four at the elevated temperature will usually cause the reaction to go to completion.

The triple bond is then saturated, preferably by catalytic hydrogenation. For example, the silyl ether can be dissolved in a saturated solvent such as an alcohol, a heavy metal catalyst added (Pd-C) and the mixture put under $H_2$ for a time sufficient to reduce the triple bond. Stirring for 2 to 6 hours will usually effect the reaction.

Recovering the alcohol is done by treating the silyl ether with a fluoride source such as tetrabutylammonium fluoride. Reactants are combined at a mildly reduced temperature, eg. 0° C., then the reaction is allowed to run its course at ambient temperature or there about. Several hours may be needed for the reaction to go to completion. Product was recovered by extraction means.

Converting the alcohol to the iodo compound is accomplished using a phosphine, imidazole and $I_2$. In actual practice, this transformation is accomplished by adding to a solution of alcohol under argon, a molar excess of triphenylphosphine, for example, and a three-fold excess of imidazole followed by iodine. Materials are combined at room temperature, but then the reaction pot may be heated to between 50°–70° C. for a brief period, 10 minutes to an hour to complete the reaction. Standard procedures are then used to recover and purify the product.

Scheme II illustrates an alternative process for making R groups.

Scheme II

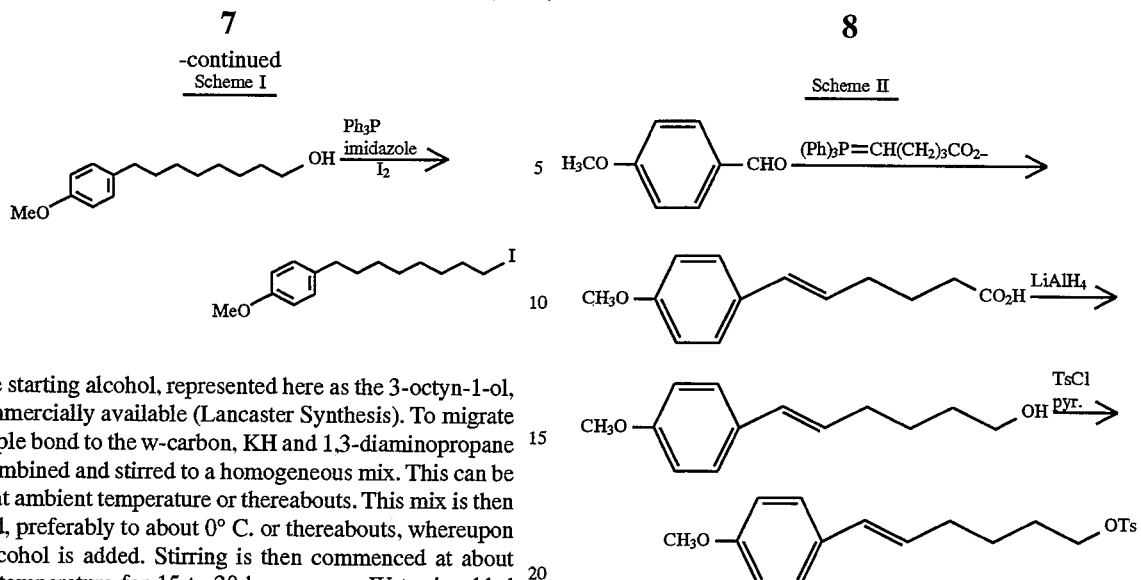

While the methoxyphenyl compound is illustrated here, this series of steps and reagents may be used to make other substituted-w-phenylaliphatic groups denoted by R. The starting material, the benzaldehydes, are commercially available or can be readily made by known methods.

To make the acid, first an alkylsilazide is added to an inert solvent under an inert atmosphere. Then the phosphonium salt is added. This addition can be done at room temperature or thereabouts. After a brief period of mixing, this mixture is usually a suspension, the benzaldehyde is added slowly at about room temperature. A slight molar excess of the phosphonium salt is employed. After an additional brief period of stirring at about room temperature, the reaction is quenched with water. The solution is acidified and the acid extracted with a suitable organic solvent. Further separatory and purification procedures may be employed as desired.

The alcohol is made by reducing the acid using a reducing agent. Lithium aluminum hydride or similar reducing agents may be employed, and conditions may be varied as needed to effect the reduction.

The tosylate is prepared in an inert solvent employing a base such as pyridine. Suitable conditions include carrying out the reaction at room temperature or thereabouts for a period of 1 to 5 hours. Other leaving groups similar in function to the tosylate may be prepared and will be useful as a means for forming the R moiety.

These procedures can be used to make the full spectrum of radicals represented by R where it has a terminal phenyl group, including the substituted phenylaliphatic radicals.

Benzyl mercaptans, or analogous compounds where m is 1 or greater, are commercially available or may be made by the process of Scheme III.

Scheme III

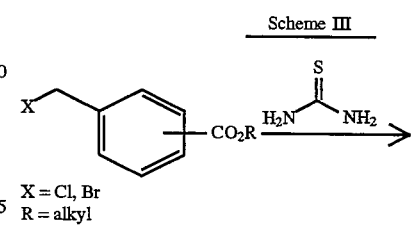

X = Cl, Br
R = alkyl

-continued
Scheme III

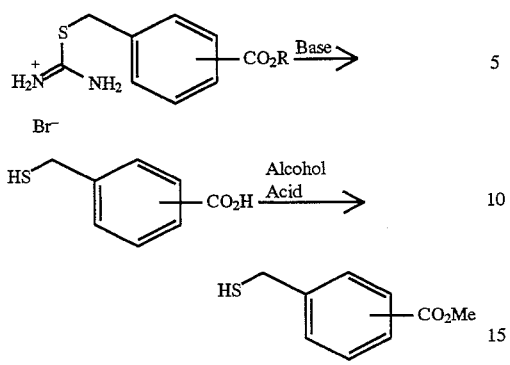

Starting material, the haloalkylbenzoates, are commercially available or can be made by methods known in the art. Thiourea is added to a solution of haloalkylbenzoate at ambient temperature or thereabouts. Any appropriate solvent may be used, acetone for example. A precipitate of the thiouronium salts should form under these conditions. The precipitate is collected and dissolved in water and the pH adjusted to about 10.5 with a base, for example a solution of NaOH. Refluxing is then commenced for between 1 and 4 hours. Product, as the free acid, is then recovered by some other separatory and purification means. Esterification is then carried out by mixing the acid with an alcohol, bubbling HCl through the solution, and letting sit the resulting solution for a time not more than several days; two days usually is sufficient to effect the reaction.

Compounds of formula I where Z is oxygen can be made by the sequence of steps given in Scheme IV.

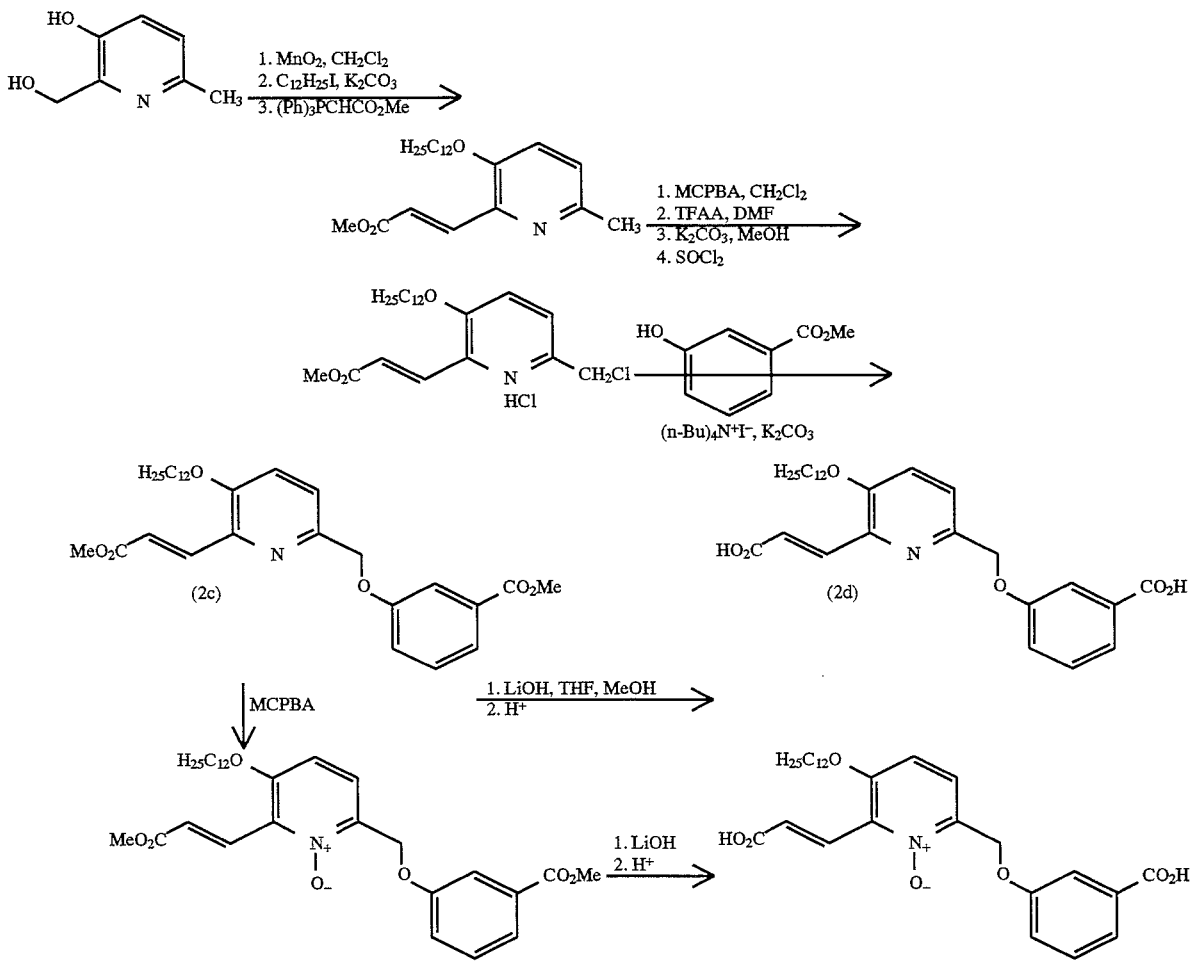

The starting material is available from Aldrich. It is treated with a mild oxidizing agent such as $MnO_2$ to oxidize the 2-hydroxyethyl group to the corresponding aldehyde.

The R group is then formed. In this case an ether is prepared under basic conditions using an a-halo intermediate. A tosylate made as per Scheme III, can also be used in this step. Introducing the acid function at position 2 is accomplished by means of a triphenylphosphoranylidene reagent. The acetate form is illustrated here but other similar reagents could be used. The N-oxide is then formed by means of a peroxy acid. Trifluoroacetic anhydride is used to oxidize the 6-position methyl group. This hydroxymethyl group is then converted to the corresponding halide, (in the hydrohalide form) in this case the chloride, by means of thionyl chloride. An alkyl hydroxybenzoate is then reacted with the 6-chloromethyl compound in the presence of tetrabutylammonium iodide and a weak base. The resulting diester can be hydrolyzed to the salt or, further, acidified to give the free acid. An oxidant can be used to regenerate the N-oxide which can then be treated with base to hydrolyze the esters. Esters can be converted to salts, the free acids and other derivatives. Catalytic hydrogenation can be used to reduce the double bond in the $R_1$ group described here.

Scheme V illustrates a method for making compounds where Z is a S and m is 0.

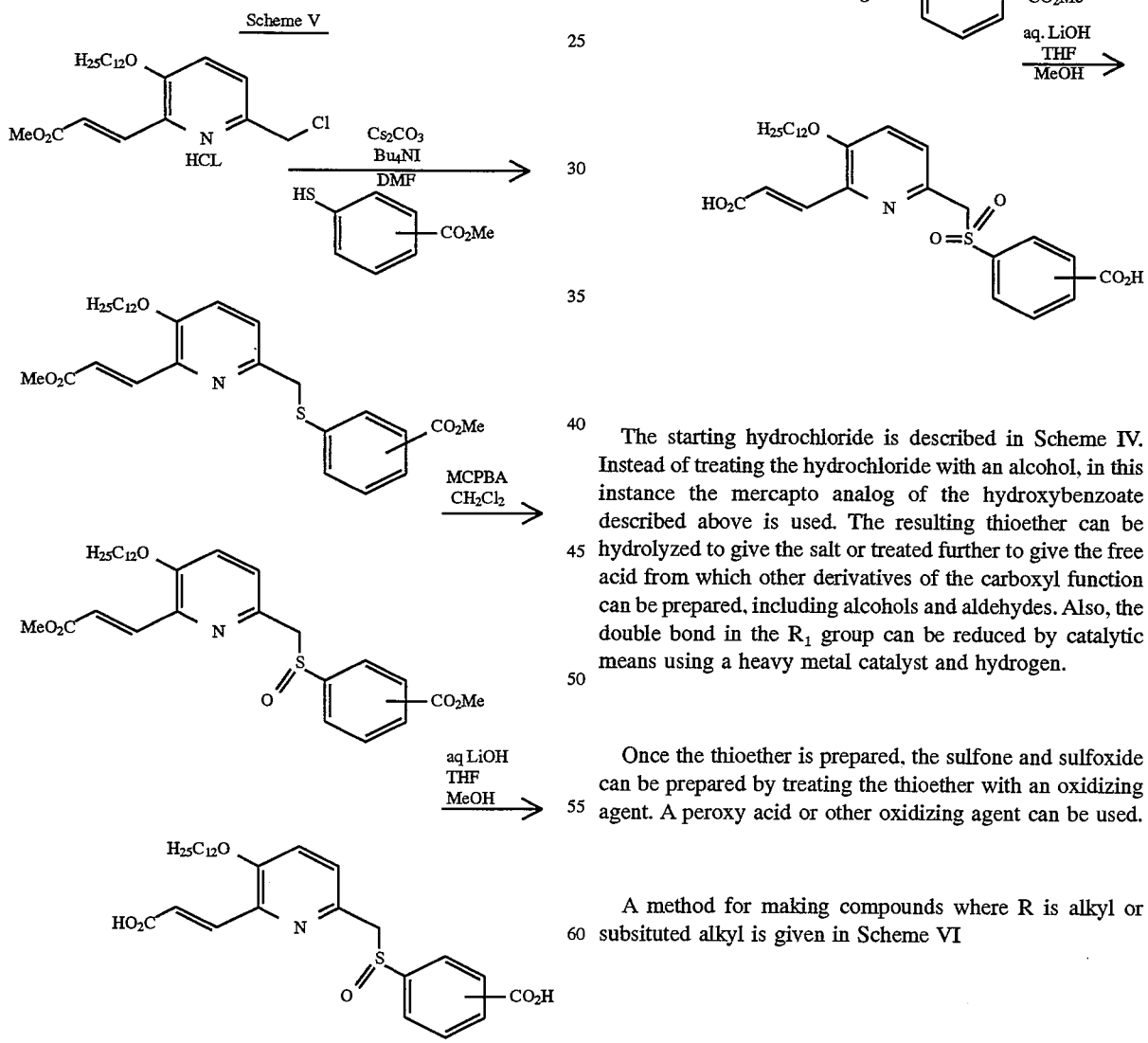

Scheme V

-continued
Scheme V

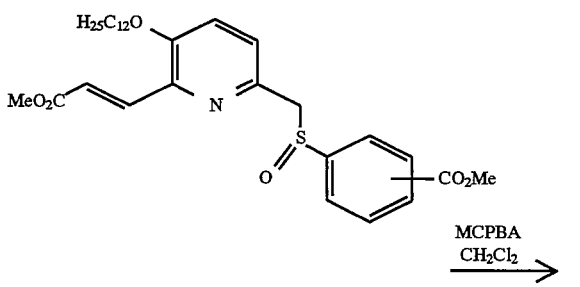

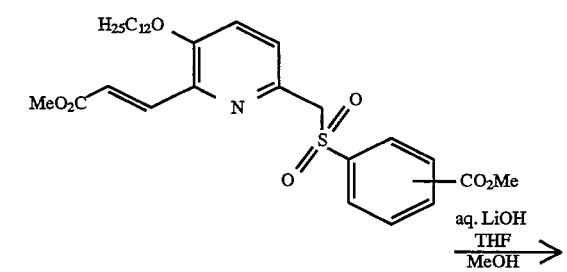

The starting hydrochloride is described in Scheme IV. Instead of treating the hydrochloride with an alcohol, in this instance the mercapto analog of the hydroxybenzoate described above is used. The resulting thioether can be hydrolyzed to give the salt or treated further to give the free acid from which other derivatives of the carboxyl function can be prepared, including alcohols and aldehydes. Also, the double bond in the $R_1$ group can be reduced by catalytic means using a heavy metal catalyst and hydrogen.

Once the thioether is prepared, the sulfone and sulfoxide can be prepared by treating the thioether with an oxidizing agent. A peroxy acid or other oxidizing agent can be used.

A method for making compounds where R is alkyl or subsituted alkyl is given in Scheme VI Scheme VI

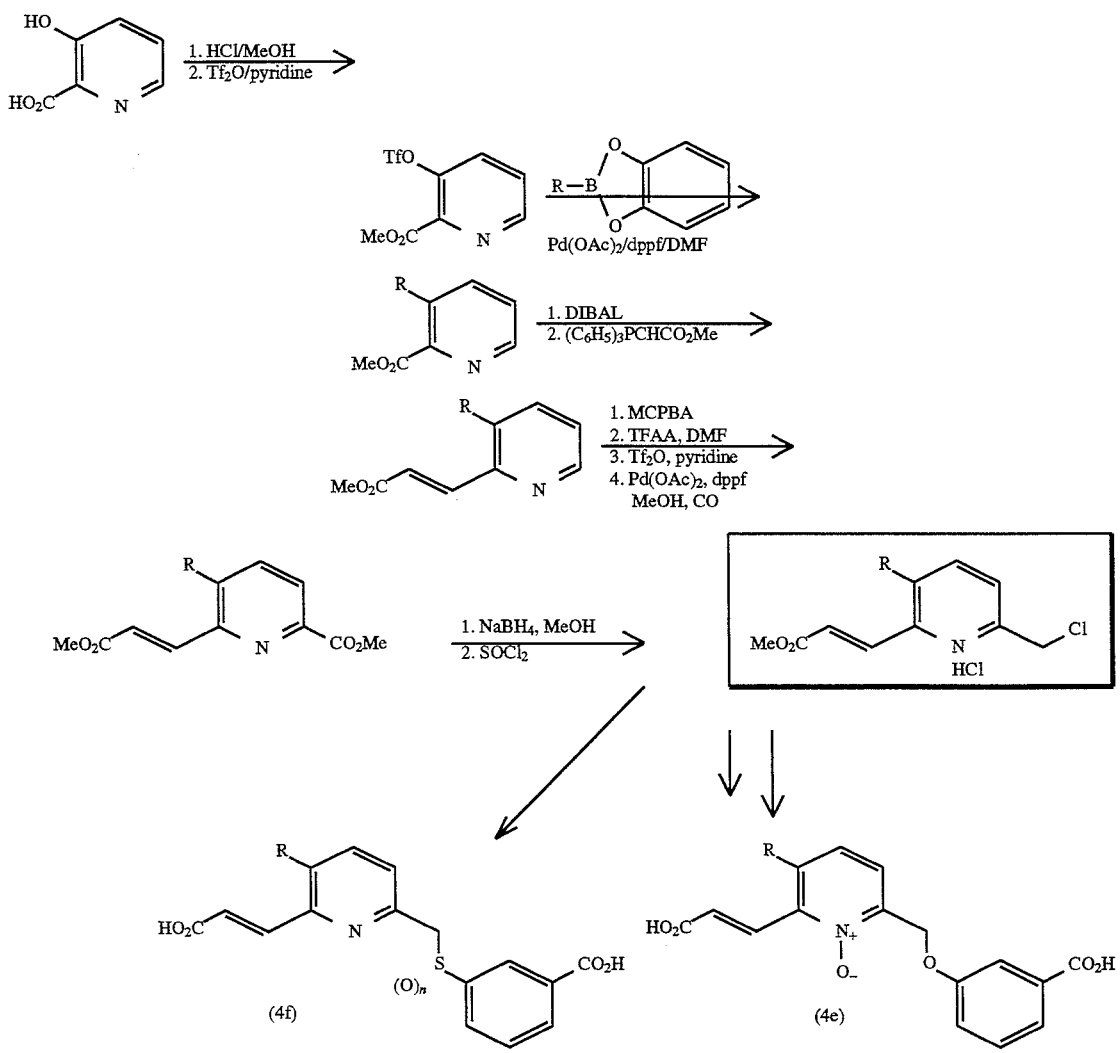

In this Scheme, 2-hydroxypicolinic acid is converted to the alkyl ester using the corresponding alcohol and an acid to catalyze the reaction. The hydroxyl group is then converted to the trifluoromethysulfonate by means of trifluoromethanesulfonic anhydride and a base, e.g. pyridine. The lipid tail is attached using the appropriate alkyl catechol boronate under palladium coupling conditions. For example, 1-iododecene and catechol borane are reacted to form the alkyl catechol boronate. Then the alkylation reaction is effected using Pd(OAc)$_2$. The ester is reduced to the corresponding aldehyde with a hydride such as diisobutylaluminum hydride (DIBAL). A Wittig olefination is then carried out using, for example, methyl(triphenylphosphoranylidene) acetate. The resulting pyridyl methyl acrylate is then oxidized to the N-oxide with an oxidizing agent such as 3-chloroperoxybenzoic acid. This oxide is then rearranged to the 2-pyridone with trifluoroacetic arthydride. A trifluoromethylsulfonate is then formed using trifluoromethanesulfonic anhydride and pyridine. Carbomethylation is then effected by means of Pd(OAc)$_2$, a simple alcohol, and carbon monoxide. Selectively reducing the pyridyl-ester (using a hydride such as NaBH$_4$ in a low molecular weight alcohol) yields the 2-(hydroxymethyl)-pyridine. This compound is treated with thionyl chloride to form the 6-chloromethyl compound. This intermediate is transformed to the ethers or thioether of formula I in the same manner as is illusrated in Schemes IV—VI.

Pharmaceutical compositions of the present invention comprise a pharmaceutical carrier or diluent and some amount of a compound of the formula (I). The compound may be present in an amount to effect a physiological response, or it may be present in a lesser amount such that the user will need to take two or more units of the compositon to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For parenteral administration the pharmaceutical composition will be in the form of a sterile injectable liquid such as an ampule or an aqueous or non-aqueous liquid suspension.

For topical administration the pharmaceutical composition will be in the form of a cream, ointment, liniment, lotion, pastes, and drops suitable for administration to the eye, ear, or nose.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingedients do not have a detrimental effect on the therapeutic action of the instant compositions.

The pharmaceutical preparations thus described are made following the conventional techniques of the pharmaceutical chemist as appropriate to the desired end product.

Formulations for treating psoriasis can take the form of oral or topical preparations. Topically applied formulations are preferred. Ointments, creams, liniments, lotions, pastes and similar preparations are examples of preferred topical formulations. Aerosols may also be used. These dosage forms will contain between 0.01 and 5 percent by weight of the active ingredient.

Usually a compound of formula I is administered, that is applied, to a subject in a composition comprising a nontoxic amount sufficient to produce an inhibition of the symptoms of a disease state. When administered orally, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg. When a topical formulation is used, the mount applied will depend on the size of the affected area and the severity and progress of the disease, ie. psoriasis.

Included within the scope of this disclosure is the method of treating a disease mediated by $LTB_4$ which comprises administering to a subject a therapeutically effective amount of a compound of formula I, preferably in the form of a pharmaceutical composition. For example, inhibiting the inflammatory response resulting from psoriasis by administration of an effective amount of a compound of formula I is included within the scope of this disclosure. The administration may be carried out in dosage units at suitable intervals or in single doses as needed. Usually this method will be practiced when relief of symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the condition or disease being treated, and so forth.

Pharmaceutical compositions and their method of use also include the combination of a compound of formula I with $H_1$ blockers where the combination contains sufficient amounts of both compounds to treat antigen-induced respiratory anaphylaxis or similar allergic reaction. Representative $H_1$ blockers useful here include: cromolyn sodium, compounds from the ethanolamines class (diphenhydramine), ethylenediamines (pyrilamine), the alkylamine class (chlorpheniramine), the piperazine class (chlorcyclizine), and the phenothiazine class (promethazine). $H_1$ blockers such as 2-[4-(5-bromo-3-methylpyrid-2-yl)butylamino]-5-[(6-methylpyrid-3-yl)methyl]-4-pyrimidone are particularly useful in this invention.

Bioassays

The specificity of the antagonist activity of a number of the compounds of this invention is demonstrated by relatively low levels of antagonism toward agonists such as potassium chloride, carbachol, histamine and $PGF_2$.

The receptor binding affinity of the compounds used in the method of this invention is measured by the ability of the compounds to bind to $[^3H]$-$LTB_4$ binding sites on human U937 cell membranes. The $LTB_4$ antagonist activity of the compounds used in the method of this invention is measured by their ability to antagonize in a dose dependent manner the $LTB_4$ elicited calcium transient measured with fura-2, the fluorescent calcium probe. The methods employed were as follows:

U-937 Cell Culture Conditions

U-937 cells were obtained from Dr. John Bomalaski (Medical College of PA) and Dr. John Lee (SmithKline Beecham Corp., Dept. of Immunology) and grown in RPMI-1640 medium supplemented with 10% (v/v) heat inactivated fetal calf serum, in a humidified environment of 5% $CO_2$, 95% air at 37° C. Cells were grown both in T-flasks and in Spinner culture. For differentiation of the U937 cells with DMSO to macrophagelike cells, the cells were seeded at a concentration of $1 \times 10^5$ cells/ml in the above medium with 1.3% DMSO and the incubation continued for 4 days. The cells were generally at a density of $0.75-1.25 \times 10^6$ cells/ml and were harvested by centrifugation at 800× g for 10 min.

Preparation of U-937 Cell Membrane Enriched Fraction

Harvested U-937 cells were washed with 50 mM Tris-HCl, pH 7.4 at 25° C. containing 1 mM EDTA (buffet A). Cells were resuspended in buffer A at a concentration of $5 \times 10^7$ cells/ml and disrupted by nitrogen cavitation with a Parr bomb at 750 psi for 10 min at 0° C. The broken cell preparation was centrifuged at 1,000× g for 10 min. The supernatant was centrifuged at 50,000× g for 30 min. The pellet was washed twice with buffer A. The pellet was resuspended at about 3 mg membrane protein/ml with 50 mM Tris-HCl, pH 7.4 at 25° C. and aliquots were rapidly frozen and stored at −7° C.

Binding of $[^3H]$-$LTB_4$ to U-937 Membrane Receptors $[^3H]$-$LTB_4$ binding assays were performed at 25° C., in 50 mM Tris-HCl (pH 7.5) buffer containing 10 mM $CaCl_2$, 10 mM $MgCl_2$, $[^3H]$-$LTB_4$, U937 cell membrane protein (standard conditions) in the presence or absence of varying concentrations of $LTB_4$, or test compounds. Each experimental point represents the means of triplicate determinations. Total and non-specific binding of $[^3H]$-$LTB_4$ were determined in the absence or presence of 2 mM of unlabeled $LTB_4$, respectively. Specific binding was calculated as the difference between total and non-specific binding. The radioligand competition experiments were performed, under standard conditions, using approximately 0.2 nM $[^3H]$-$LTB_4$, 20–40 mg of U937 cell membrane protein, increasing concentrations of $LTB_4$ (0.1 mM to 10 mM) or other competing ligands (0.1 mM to 30 mM) in a reaction volume of 0.2 ml and incubated for 30 minutes at 25° C. The unbound radioligand and competing drugs were separated from the membrane bound ligand by a vacuum filtration technique. The membrane bound radioactivity on the filters was determined by liquid scintillation spectrometry.

Saturation binding experiments for U937 cells were performed, under standard conditions, using approximately 15–50 mg of U-937 membrane protein and increasing concentrations of [$^3$H]-LTB$_4$ (0.02–2.0 nM) in a reaction volume of 0.2 ml and incubation at 22° C., for 30 minutes. LTB$_4$ (2 mM) was included in a separate set of incubation tubes to determine non-specific binding. The data from the saturation binding experiments was subjected to computer assisted non-linear least square curve fitting analysis and further analyzed by the method of Scatchard.

Loading Differentiated U-937 Cells with Fura-2

Harvested cells were resuspended at 2×10$^6$ cells/ml in Krebs Ringer Hensilet buffer containing 0.1% BSA (RIA grade), 1.1 mM MgSO$_4$, 1.0 mM CaCl$_2$ and 5 mM HEPES (pH 7.4, buffer B). The diacetomethoxy ester of fura-2 (fura-2/AM) was added to a final concentration of 2 mM and cells incubated in the dark for 30 minutes at 37° C. The cells were centrifuged at 800× g for 10 minutes and resuspended at 2×10$^6$ cells/ml in fresh buffer B and incubated at 37° C. for 20 minutes to allow for complete hydrolysis of entrapped ester. The cells were centrifuged at 800× g for 10 minutes and resuspended in cold fresh buffer B at 5×10$^6$ cells/ml Cells were maintained on ice in the dark until used for fluorescent measurements.

Fluorescent Measurements—Calcium Mobilization

The fluorescence of fura-2-containing U937 cells was measured with a fluorometer designed by the Johnson Foundation Biomedical Instrumentation Group. A fluorometer was equipped with temperature control and a magnetic stirrer under the cuvette holder. The wave lengths are set at 339 nm for excitation and 499 nm for emission. All experiments were performed at 37° C. with constant mixing.

U-937 cells were diluted with fresh buffer (B) to a concentration of 1×10$^6$ cells/ml and maintained in the dark on ice. Aliquots (2 ml) of the cell suspension were put into 4 ml cuvettes and the temperature brought up to 37° C., (maintained in 37° C., water bath for 10 min). Cuvettes were transferred to the fluorometer and fluorescence measured for about one minute before addition of stimulants or antagonists and followed for about 2 minutes post stimulus. Agonists and antagonists were added as 2 ml aliquots.

Antagonists were added first to the cells in the fluorometer in order to detect potential agonist activity. Then after about one minute 10 nM LTB$_4$ (a near maximal effective concentration) was added and the maximal Ca$^{2+}$ mobilization [Ca$^{2+}$]$_i$ was calculated using the following formula:

$$[Ca^{2+}]i = 244 \left\{ \frac{F - Fmin}{Fmax - F} \right\}$$

F was the maximum relative fluorescence measurement of the sample. Fmax was determined by lysing the cells with 10 ml of 10% Triton X-100 (final Concentration 0.02%). After Fmax was determined 67 ml of 100 mM EDTA solution (pH 10) was added to totally chelate the Ca$^{2+}$ and quench the fura-2 signal and obtain the Fmin. The [Ca$^{2+}$]$_i$ level for 10 nM LTB$_4$ in the absence of an antagonist was 100% and basal [Ca$^{2+}$]$_i$ was 0% . The IC$_{50}$ concentration is the concentration of antagonist which blocks 50% of the 10 nM LTB$_4$ induced [Ca$^{2+}$]$_i$ mobilization. The EC$_{50}$ for LTB$_4$ induced increase in [Ca$^{2+}$]$_i$ mobilization was the concentration for half maximal increase. The K$_i$ for calcium mobilization was determined using the formula:

$$K_i = \frac{IC_{50}}{1 + \frac{[LTB_4]}{[EC_{50}]}}$$

With the experiments described, the LTB$_4$ concentration was 10 nM and the EC$_{50}$ was 2 nM.

SPECIFIC EMBODIMENTS

The following examples are given to illustrate how to make and use the compounds of this invention. These Examples are just that, examples, and are not intended to circumscribe or otherwise limit the scope of this invention. Reference is made to the claims for defining what is reserved to the inventors by this document.

EXAMPLE 1

8-(4-Methoxyphenyl)octan-1-(4-toluenesulfonate)

1(a) 7-Octyn-1-ol.

35% KH in mineral oil (27 g, 240 mmol) under an argon atmosphere was washed with hexane and treated dropwise with 1,3-diaminopropane. The mixture was stirred at room temperature until it became homogeneous. The flask was cooled to 0∞C. and 3-octyn-1-ol (10 g, 79 mmol, Lancaster Synthesis) was slowly added. The reaction was then stirred at room temperature for 18 hours. The reaction was quenched with H$_2$O (50 mL) and the product was extracted into ether. The organic layer was washed with 10% HCl (3×15 mL) and brine and dried (MgSO$_4$). Evaporation gave the title product which was used without further purification: $^1$H NMR (90 MHz, CDCl$_3$) d 3.65 (t, J=5 Hz, 2H, OCH$_2$), 2.23 (m, 2H, CH$_2$), 2.0 (m, 1H, acetylenic), 1.7–1.2 (m, 8H, (CH$_2$)$_4$); IR (neat) u$_{max}$ 3350, 2930, 2125 cm$^{-1}$.

1(b) 7-Octyn-1-t-butyldiphenylsilyl ether.

7-Octyn-1-ol (3.8 g) was dissolved in dimethylformamide (10 mL) and treated with t-butylchlorodiphenylsilane (10.2 mL, 33 mmol) and imidazole (3.65 g, 45 mmol) at 0∞C. The reaction was stirred at 0∞C. for 10 minutes and at room temperature for 3 hours. Water was added and the product was extracted into ethyl acetate. The ethyl acetate extract was washed with H$_2$O and brine and dried (Na$_2$SO$_4$). The solvent was evaporated and the residue purified by flash column chromatography (silica, hexanes) to give a yellow oil: $^1$H NMR (250 MHz, CDCl$_3$)d7.7 (d, 4H, aryl), 7.4 (m, 6H, aryl), 3.63 (t, 2H, OCH$_2$), 2.23 (m, 2H, CH$_2$), 1.97 (t, 1H, acetylenic), 1.6–1.3 (m, 8H, (CH$_2$)$_4$), 1.05 (s, 9H, t-butyl); IR (film)u$_{max}$ 3321, 2940, 2125 cm$^{-1}$.

1(c) 8-(4-Methoxyphenyl)-7-octyn-1-t-butyldiphenylsilyl ether

To a flame-dried flask under an argon atmosphere was added 4-iodoanisole (5.34 g, 22 mmol) in triethylamine (50 mL) followed by the addition of 7-octyn-1-t-butyldiphenylsilyl ether (9.84 g, 27 mmol), (Ph$_3$P)$_2$PdCl$_2$ (350 mg, 0.44 mmol), and CuI (200 mg, 0.88 mmol). The resulting mixture was heated at 50∞C. for 4 hours. Upon cooling to room temperature the reaction mixture was filtered and the solvent evaporated. The residue was partitioned between ethyl acetate and H$_2$O and the organic layer was collected and washed with brine and dried (Na$_2$SO$_4$). The solvent was evaporated and the residue was purified by flash column chromatography (silica, 1% ethyl acetate in hexanes) to give an oil: $^1$H NMR (250 MHz, CDCl$_3$) δ7.7 (d, 4H, aryl), 7.4 (m, 6H, aryl), 7.35 (d, 2H, aryl), 6.8 (d, 2H, aryl), 3.8 (s, 3H, OCH$_3$), 3.7 (t, 2H, OCH$_2$), 2.4 (t, 2H, CH$_2$), 1.7–1.3 (m, 8H, (CH$_2$)$_4$), 1.05 (s, 9H, t-butyl).

1(d) 8-(4-Methoxyphenyl)octan-1-t-butyldiphenylsilyl ether.

To 8-(4-methoxyphenyl)-7-octyn-1-t-butyldiphenylsilyl ether (2.16 g, 4.6 mmol) in ethanol (10 mL) and ethyl acetate (10 mL) was added 5% Pd/C (100 mg). The mixture was subjected to 75 psi of $H_2$ for 4 hours. The reaction was filtered through Celite and the solvent evaporated to give an oil: $^1$H NMR (250 MHz, CDCl$_3$) δ7.7 (d, 4H, aryl), 7.4 (m, 6H, aryl), 7.05 (d, 2H, aryl), 6.8 (d, 2H, aryl), 3.8 (s, 3H, OCH$_3$), 3.6 (t, 2H, OCH$_2$), 2.5 (t, 2H, benzylic), 1.75–1.3 (m, 12H, (CH$_2$)$_6$), 1.0 (s, 9H, t-butyl):

1(e) 8-(4-Methoxyphenyl)octan-1-ol.

8-(4-Methoxyphenyl)octan-1-t-butyldiphenylsilyl ether (2.18 g, 4.6 mmol) in tetrahydrofuran (20 mL) was cooled to 0∞C. and treated with tetrabutylammonium fluoride (14 mL, 14 mmol, 1M in tetrahydrofuran). The cooling bath was removed and the reaction was stirred at room temperature for 24 hours. The reaction was diluted with ethyl acetate and was washed with H$_2$O and brine and dried (Na$_2$SO$_4$). The solvent was evaporated and the residue was purified by flash column chromatography (silica, 0–20% ethyl acetate in hexanes) to give a white solid: $^1$H NMR (250 MHz, CDCl$_3$) δ7.15 (d, 2H, aryl), 6.86 (d, 2H, aryl), 3.85 (s, 3H, OCH$_3$), 3.68 (t, 2H, OCH$_2$), 2.62 (t, 2H, benzylic), 1.75–1.3 (m, 12H, (CH$_2$)$_6$).

1(f) 8-(4-Methoxyphenyl)octan-1-(4-toluenesulfonate).

6-(4-Methoxyphenyl)octan-1-ol (5.91 g, 25 mmol) was dissolved in dry CH$_2$Cl$_2$ (100 mL) under an argon atmosphere and cooled to 0∞C. To this was added pyridine (2.5 mL, 30 mmol) and 4-toluenesulfonyl chloride (5.4 g, 28 mmol). The reaction was stirred at 0∞C. for 20 minutes and at room temperature for 24 hours. The reaction solution was washed with H$_2$O and brine and dried (Na$_2$SO$_4$). The solvent was evaporated and the residue purified by flash column chromatography (silica, 0–10% ethyl acetate in hexanes) to give a white solid: $^1$H NMR (250 MHz, CDCl$_3$) δ7.79 (d, 2H, aryl), 7.35 (d, 2H, aryl), 7.09 (d, 2H, aryl), 6.82 (d, 2H, aryl), 4.04 (s, 2H, OCH$_2$), 3.8 (s, 3H, OCH$_3$), 2.55 (t, 2H, benzylic), 2.46 (s, 3H, CH$_3$), 1.75–1.15 (m, 12H, (CH$_2$)6).

EXAMPLE 2

6-(4-Methoxyphenyl)hexan-1-(4-toluenesulfonate)

2(a) 5-Hexyn-1-t-butyldiphenylsilyl ether

5-Hexyn-1-ol (3 g, 30 mmol, Aldrich) was dissolved in dimethylformamide (10 mL) and treated with t-butylchlorodiphenylsilane (10.2 mL, 33 mmol) and imidazole (3.65 g, 45 mmol) at 0∞C. The reaction was stirred at 0∞C. for 10 minutes and at room temperature for 3 hours. Water was added and the product was extracted into ethyl acetate. The ethyl acetate extract was washed with H$_2$O and brine and dried (Na$_2$SO$_4$). The solvent was evaporated and the residue purified by flash column chromatography (silica, hexanes) to give a yellow oil: $^1$H NMR (250 MHz, CDCl$_3$) δ7.7 (d, 4H, aryl), 7.4 (m, 6H, aryl), 3.65 (t, 2H, OCH$_2$), 2.2 (m, 2H, CH$_2$), 1.9 (t, 1H, acetylenic), 1.7 (m, 4H, CH$_2$—CH$_2$), 1.05 (s, 9H, t-butyl).

2(b) 6-(4-Methoxyphenyl)-5-hexyn-1-t-butyldiphenylsilyl ether.

To a flame-dried flask under an argon atmosphere was added 4-iodoanisole (5.34 g, 22 mmol) in triethylamine (50 mL) followed by the addition of 5-hexyn-1-t-butyldiphenylsilyl ether (8.83 g, 27 mmol), (Ph$_3$P)$_2$PdCl$_2$ (350 mg, 0.44 mmol), and CuI (200 mg, 0.88 mmol). The resulting mixture was heated at 50∞C. for 4 hours. Upon cooling to room temperature the reaction mixture was filtered and the solvent evaporated. The residue was partitioned between ethyl acetate and H$_2$O and the organic layer was collected and washed with brine and dried (Na$_2$SO$_4$). The solvent was evaporated and the residue was purified by flash column chromatography (silica, 1% ethyl acetate in hexanes) to give an oil: $^1$H NMR (250 MHz, CDCl$_3$) δ7.7 (d, 4H, aryl), 7.4 (m, 6H, aryl), 7.35 (d, 2H, aryl), 6.8 (d, 2H, aryl), 3.8 (s, 3H, OCH$_3$), 3.7 (t, 2H, OCH$_2$), 2.4 (t, 2H, CH$_2$), 1.7 (m, 4H, CH$_2$—CH$_2$), 1.05 (s, 9H, t-butyl).

2(c) 6-(4-Methoxyphenyl)hexan-1-t-butyldiphenylsilyl ether.

To 6-(4-methoxyphenyl)-5-hexyn-1-t-butyldiphenylsilyl ether (2.0 g, 4.6 mmol) in ethanol (10 mL) and ethylacetate (10 mL) was added 5% Pd/C (100 mg). The mixture was subjected to 75 psi of H$_2$ for 4 hours. The reaction was filtered through Celite and the solvent evaporated to give an oil: $^1$H NMR (250 MHz, CDCl$_3$) δ7.7 (d, 4H, aryl), 7.4 (m, 6H, aryl), 7.05 (d, 2H, aryl), 6.8 (d, 2H, aryl), 3.8 (s, 3H, OCH$_3$), 3.6 (t, 2H, OCH$_2$), 2.5 (t, 2H, benzylic), 1.55 (m, 4H, CH$_2$—CH$_2$), 1.3 (m, 4H, CH$_2$—CH$_2$), 1.0 (s, 9H, t-butyl).

2(e) 6-(4-Methoxyphenyl)hexan-1-ol.

6-(4-Methoxyphenyl)hexan-1-t-butyldiphenylsilyl ether (2.0 g, 4.6 mmol) in tetrahydrofuran (20 mL) was cooled to 0∞C. and treated with tetrabutylammonium fluoride (14 mL, 14 mmol, 1M in tetrahydrofuran). The cooling bath was removed and the reaction was stirred at room temperature for 24 hours. The reaction was diluted with ethyl acetate and was washed with H$_2$O and brine and dried (Na$_2$SO$_4$). The solvent was evaporated and the residue was purified by flash column chromatography (silica, 0–20% ethyl acetate in hexanes) to give a white solid: $^1$H NMR (250 MHz, CDCl$_3$) δ7.05 (d, 2H, aryl), 6.8 (d, 2H, aryl), 3.8 (s, 3H, OCH$_3$), 3.65 (t, 2H, OCH$_2$), 2.55 (t,2H, benzylic), 1.6 (m, 4H, CH$_2$—CH$_2$), 1.4 (m, 4H, CH$_2$—CH$_2$).

2(f) 6-(4-Methoxyphenyl)hexan-1-(4-toluenesulfonate).

6-(4-Methoxyphenyl)hexan-1-ol (5.36 g, 25 mmol) was dissolved in dry CH$_2$Cl$_2$ (100 mL) under an argon atmosphere and cooled to 0∞C. To this was added pyridine (2.5 mL, 30 mmol) and 4-toluenesulfonyl chloride (5.4 g, 28 mmol). The reaction was stirred at 0∞C. for 20 minutes and at room temperature for 24 hours. The reaction solution was washed with H$_2$O and brine and dried (Na$_2$SO$_4$). The solvent was evaporated and the residue purified by flash column chromatography (silica, 0–10% ethyl acetate in hexanes) to give a white solid: $^1$H NMR (250 MHz, CDCl$_3$) δ1.6–1.3 (m, 8H, (CH$_2$)$_4$), 2.4 (s, 3H, CH$_3$), 2.5 (t, 2H, benzylic), 3.8 (s, 3H, OCH$_3$), 4.0 (t, 2H, OCH$_2$), 6.80 (d, 2H, aryl), 7.0 (d, 2H, aryl), 7.3 (d, 2H, aryl), 7.8 (d, 2H, aryl).

EXAMPLE 3

E-6-(4-methoxyphenyl)-1-(4-toluenesulfonate)-5-hexene

3(a) E-4-Methoxyphenyl-5-hexenoic acid.

To a freshly prepared solution of lithium hexamethyldisilazide (64 mmol) in tetrahydrofuran (30 mL), under an argon atmosphere, was added a suspension of (4-carboxybutyl)triphenylphosphonium bromide (17.6 g, 30 mmol) in tetrahydrofuran (45 mL) at room temperature. The reaction was stirred for 15 minutes during which time the orange-red color of the ylide developed. A solution of 4-anisaldehyde (4.5 g, 30 mmol) in tetrahydrofuran (30 mL) was added dropwise and stirring was continued for an additional 20 minutes. The reaction was quenched with H$_2$O (50 mL) and diluted with ether (30 mL). The aqueous layer was acidified to pH 1.0 with 3N HCl and the product was extracted into ethyl acetate (3×50 mL). The combined organic layers were dried (MgSO$_4$) and the product was purified by flash column chromatography (silica, 1% methanol in CH$_2$Cl$_2$) to yield the E-olefin as a solid: $^1$H NMR (200 MHz, CDCl$_3$) δ7.3 (d, 2H, aryl), 6.8 (d, 2H, aryl), 6.3 (d, 1H, olefin), 6.0 (m, 1H, olefin), 3.8 (s, 3H, OCH$_3$), 2.3 (m, 4H, allylic CH$_2$ and CH$_2$CO$_2$), 1.8 (q, 2H, CH$_2$).

3(b) E4-Methoxyphenyl-5-hexen-1-ol.

E4-Methoxyphenyl-5-hexenoic acid (1.1 g, 5.0 mmol) in dry ether (10 mL) was slowly added to a suspension of LiAlH$_4$ (240 mg, 6.0 mmol) in ether (10 mL) under an argon atmosphere. The reacfiofi mixture was refluxed for 45 minutes. Upon cooling to room temperature the reaction was quenched with H$_2$O (10 mL) followed by 6N H$_2$SO$_4$ (7 mL). Ethyl acetate (20 mL) was added and the organic layer was separated and dried (MgSO$_4$); evaporation gave a white crystalline solid: mp. 65–66∞C.; $^1$H NMR (200 MHz, CDCl$_3$) δ7.2 (d, 2H, aryl), 6.8 (d, 2H, aryl), 6.3 (d, 1H, olefin), 6.1 (m 1H, olefin), 3.8 (s, 3H, OCH$_3$), 3.6 (t, 2H, OCH$_2$), 2.2 (q, 2H, allylic), 1.5 (m, 4H, CH$_2$—CH$_2$); Anal. Calcd. for C$_{13}$H$_{18}$O$_2$:C,75.65; H, 8.80, found: C, 75.45: H, 8.95; MS (CI): 207 (M+H).

3(c) E-6-(4-methoxyphenyl)-1-(4-toluenesulfonate)-5-hexene.

E-4-Methoxyphenyl-5-hexen1-ol (1.6 g, 7.0 mmol) was dissolved in dry CH$_2$Cl$_2$ (50 mL) under an argon atmosphere and treated with 4-toluenesulfonyl chloride (7.0 g, 36 mmol) and pyridine (3 mL). The reaction solution was stirred at room temperature for 3.5 hours. Water (40 mL) was added to the reaction and the organic layer was separated and dried (MgSO$_4$). The product was purified by flash column chromatography (silica, 10% ethyl acetate in hexane) to give an oil: $^1$H NMR (200 MHz, CDCl$_3$) δ7.8 (d, 2H, aryl), 7.3 (d, 2H, aryl), 7.2 (d, 2H, aryl), 6.8 (d, 2H, aryl), 6.2 (d, 1H, olefin), 6.0 (m, 1H, olefin), 4.1 (t, 2H, OCH$_2$), 3.8 (s, 3H, OCH$_3$), 2.4 (s, 3H, CH$_3$), 2.1 (q, 2H, allylic), 1.6 (m, 4H, CH$_2$—CH$_2$); MS (CI): 361 (M+H).

EXAMPLE 4

1-Iodo-8-(4-methoxyphenyl)octane

4(a) 7-Octyn-1-ol.

Potassium hydride, (35%) in mineral oil (27 g, 240 mmol) under an argon atmosphere was washed with hexane and treated dropwise with 1,3-diaminopropane. The mixture was stirred at room temperature until it became homogeneous. The flask was cooled to 0° C. and 3-octyn-1-ol (10 g, 79 mmol, Lancaster Synthesis) was slowly added. The reaction was then stirred at room temperature for 18 hours. The reaction was quenched with H$_2$O (50 mL) and the product was extracted into ether. The organic layer was washed with 10% HCl and brine and dried (MgSO$_4$). Evaporation gave the captioned product as a colorless oil which was used without further purification: $^1$H NMR (90 MHz, CDCl$_3$) δ3.65 (t, J=5 Hz, 2H, O—CH$_2$), 2.23 (m, 2H, CH$_2$), 2.0 (m, 1H, acetylenic), 1.7–1.2 (m, 8H, (CH$_2$)$_4$); IR (neat) n$_{max}$ 3350, 2930, 2125 cm$^{-1}$.

4(b) 7-Octyn-1-tbutyldiphenylsilyl ether.

To a cooled (0° C.) solution of 7-octyn-1-ol (9.3 g, 73.7 mmol) in dimethylformamide (DMF) (70 mL) under an argon atmosphere was added imidazole (7.5 g, 110 mmol) followed by the dropwise addition of t-butylchlorodiphenylsilane (21 mL, 81 mmol). The reaction was then stirred at room temperature for 2 hours. The reaction solution was diluted with Et$_2$O and washed with H$_2$O and brine and dried (MgSO$_4$). Purification by flash column chromatography (silica, 3% EtOAc in hexane) provided the product as a colorless oil: $^1$H NMR (250 MHz, CDCl$_3$) δ7.7 (d, 4H, aryl), 7.4 (m, 6H, aryl), 3.63 (t, 2H, O—CH$_2$), 2.23 (m, 2H, CH$_2$), 1.97 (t, 1H, acetylchic), 1.6–1.3 (m, 8H, (CH$_2$)$_4$), 1.05 (s, 9H, t-butyl); IR (film) n$_{max}$ 3321, 2940, 2125 cm$^{-1}$.

4(c) 8-(4-Methoxyphenyl)-7-octyn-1-t-butyldiphenylsilyl ether.

To a flame dried flask containing triethylamine (140 mL) under an argon atmosphere was added 4-iodoanisole (13.3 g, 56.9 mmol), 7-octyn-1-t-butyldiphenylsilyl ether (24.9 g, 68.3 mmol), (Ph$_3$P)$_2$PdCl$_2$ catalyst (793 mg, 1.13 mmol), and CuI (431 mg, 2.27 mmol). The resulting mixture was heated at 50° C. for 4 hours. Upon cooling to room temperature the reaction mixture was filtered, the solids were washed with Et$_2$O and the solvent was evaporated. The residue was diluted with Et$_2$O and washed with 5% HCl, H$_2$O, NaHCO$_3$, and brine and dried (MgSO$_4$). Purification by flash column chromatography (silica, 2% EtOAc in hexane) gave the product as an orange oil: $^1$H NMR (250 MHz, CDCl$_3$) δ7.7 (d, 4H, aryl), 7.4 (m, 6H, aryl), 7.35 (d, 2H, aryl), 6.8 (d, 2H, aryl), 3.8 (s, 3H, OCH$_3$), 3.7 (t, 2H, O—CH$_2$), 2.4 (t, 2H, CH$_2$), 1.7–1.3 (m, 8H, (ch$_2$)$_4$), 1.05 (s, 9H, t butyl).

4(d) 8-(4-Methoxyphenyl)octan-1-t-butydiphenylsilyl ether.

8-(4-Methoxyphenyl)-7-octyn-1-t-butyldiphenylsilyl ether (30 g, 63.7 mmol) was dissolved in EtOH (125 mL) and EtOAc (125 mL) and treated with 5% Pd-C catalyst (3 g). The reaction was vigorously stirred under an H$_2$ atmosphere (balloon pressure) for 4 hours. The reaction mixture was filtered through a pad of Celite and the solvent was evaporated. The resulting pale yellow oil was pure by nmr analysis and was used directly for the next step: $^1$H NMR (250 MHz, CDCl$_3$) δ7.7 (d, 4H, aryl), 7.4 (m, 6H, aryl), 7.05 (d, 2H, aryl), 6.8 (d, 2H, aryl), 3.8 (s, 3H, OCH$_3$), 3.6 (t, 2H, O—CH$_2$), 2.5 (t, 2H, benzylic), 1.75–1.3 (m, 12H, (CH$_2$)$_6$), 1.0 (s, 9H, t-butyl).

4(e) 8-(4-Methoxyphenyl)octan-1-ol.

To a cooled (0° C.) solution of 8-(4-methoxyphenyl) octan-1-t-butyldiphenylsilyl ether (63 mmol) was added tetrabutylammonium fluoride (70 mL, 70 mmol; 1M solution in THF). The cooling bath was removed and the reaction was stirred at room temperature for 4.5 hours. The solvent was evaporated and the residue was dissolved in Et$_2$O. This was washed with H$_2$O, 5% HCl, NaHCO$_3$, and brine and dried (MgSO$_4$). Purification by flash column chromatography (silica, 30% EtOAc in hexane) gave the product as a colorless solid: $^1$H NMR (250 MHz, CDCl$_3$) δ7.15 (d, J=8.6 Hz, 2H, aryl), 6.86 (d, J=8.6 Hz, 2H, aryl), 3.85 (s, 3H, OCH$_3$), 3.68 (t, j=6.5 Hz, 2H, O—CH$_2$), 2.62 (t, J=7.6 Hz, 2H, benzylic), 1.75–1.3 (m, 12H, (CH$_2$)$_6$); MS (CI): 254.2 (M+NH$_4$); mp 47°–49° C.

4(f) 1-Iodo-8-(4-methoxyphenyl)octane.

To a stirred solution of 8-(4-methoxyphenyl)octan-1-ol (12.3 g, 52 mmol) in dry toluene (200 mL) under an argon atmosphere was added triphenylphosphine (17.8 g, 67.6 mmol) and imidazole (10.6 g, 156 mmol). After the imidazole had dissolved, I$_2$ (17.1 g, 67.6 mmol) was added. The reaction was then heated at 65° C. for 30 minutes. Upon cooling to room temperature the reaction was concentrated to ¼ volume. The remaining solution was diluted with Et$_2$O and washed with H$_2$O and brine and dried (MgSO$_4$). The solvent was removed and the resulting residue was dissolved in CH$_2$Cl$_2$ and applied to a flash chromatography column (silica). Elution with 2% EtOAc in hexane provided the product as a colorless oil (slight contamination with triphenylphosphine): $^1$H NMR (250 MHz, CDCl$_3$) δ7.08 (d, J=8.6 Hz, 2H, aryl), 6.82 (d, J=8.6 Hz, 2H, aryl), 3.78 (s, 3H, OCH$_3$), 3.17 (t, J=7.4 Hz, 2H, I-CH$_2$), 2.54 (t, J=7.6 Hz, 2H, benzylic), 1.85 (m, 2H, CH$_2$), 1.60 (m, 2H, CH$_2$), 1.31 (m, 8H, aliphatic); MS (CI): 364.2 (M+NH$_4$).

EXAMPLE 5

3-]1-Oxythia-2-[2-(E-2-carboxyethenyl)-3-dodecyloxy-6-pyridyl]ethyl]benzoic acid, dilithium salt 1(a) 3-Hydroxy-6-methyl-2-pyridine carboxaldehyde.

2,6-Lutidine-a$^2$,3-diol (1.0 g, 7.18 mmol, Aldrich) was suspended in dry CH$_2$Cl$_2$ (40 mL) and treated with MnO$_2$ (6.1 g, 70 mmol). The reaction was stirred at room temperature for 6 hours. The reaction mixture was filtered through a pad of Celite and the solvent was removed in vacuo. The aldehyde was used directly in the next step without further purification: $^1$H NMR (250 MHz, CDCl$_3$): δ10.65 (s, 1H, OH), 10.30 (s, 1H, CHO), 7.30 (dd, 2H, 4-pyridyl, 5-pyridyl), 2.55 (s, 3H, CH$_3$).

5(b) 3-Dodecyloxy-6-methyl-2-pyridine carboxaldehyde.

3-Hydroxy-6-methyl-2-pyridine carboxaldehye obtained above was dissolved in dry dimethylformamide (10 mL) and treated with 1-iodododecane (2.1 mL, 8.62 mmol) and anhydrous K$_2$CO$_3$ (3.0 g, 21.7 mmol) under an argon atmosphere. The reaction was heated at 90° C. for 1 h with vigorous stirring. Upon cooling to room temperature the reaction mixture was poured into ethyl acetate (100 mL); the ethyl acetate solution was washed with H$_2$O (3×20 mL) and brine and dried (MgSO$_4$). The solvent was removed under reduced pressure and the crude product was used directly in the next step without further purification: $^1$H NMR (250 MHz, CDCl$_3$): δ10.40 (s, 1H, CHO), 7.30 (m, 2H, 4-pyridyl, 5-pyridyl), 4.07 (t, J=6.5 Hz, 2H, OCH$_2$), 2.6 (s, 3H, CH$_3$), 1.85–0.89 (m, 23H, aliphatic).

5(c) 2-(E-2-Carboxymethylethenyl)-3-dodecyloxy-6-methylpyridine.

3-Dodecyloxy-6-methyl-2-pyridine carboxaldehyde obtained above was dissolved in dry toluene (12 mL) under an argon atmosphere and treated with methyl (triphenylphosphoranylidene)acetate (5.0 g, 15 mmol). The reaction was heated for 1 hour at 50∞C. Upon cooling to room temperature the reaction was diluted with ethyl acetate (100 mL) and washed with H$_2$O (2×20 mL) and brine and dried (MgSO$_4$). Purification by flash column chromatography (silica, 7.5% ethyl acetate in petroleum ether) gave a colorless solid: $^1$H NMR (250 MHz, CDCl$_3$): δ8.07 (d, J=15.7 Hz, 1H, olefin), 7.10 (m, 2H, 4-pyridyl, 5-pyridyl), 7.05 (d, J=15.7 Hz, 1H, olefin), 3.98 (t, J=6 Hz, 2H, OCH$_2$), 3.80 (s, 3H, CO$_2$CH$_3$), 2.49 (s, 3H, CH$_3$), 1.88–0.85 (m, 23H, aliphatic).

5(d) 2-(E-2-Carboxymethylethenyl)-3-dodecyloxy-6-methylpyridine N-oxide.

2-(E-2-Carboxymethylethenyl)-3-dodecyloxy-6-methylpyridine (2.15 g, 5.95 mmol) was dissolved in dry CH$_2$Cl$_2$ (20 mL) and cooled to 0∞C.; 85% m-chloroperoxybenzoic acid (1.45 g, 7.14 mmol) was added and the reaction was stirred at 0∞C. for 30 minutes and at room temperature for 16 hours. The reaction solution was poured into saturated aqueous NaHCO$_3$ (20 mL). The aqueous phase was extracted with CH$_2$Cl$_2$ (3×20 mL) and the combined CH$_2$Cl$_2$ extracts were washed with H$_2$O (20 mL) and brine and dried (MgSO$_4$). The crude pale yellow solid was used directly in the next step without further purification: $^1$H NMR (250 MHz, CDCl$_3$): δ8.23 (d, J=16.2 Hz, 1H, olefin), 7.58 (d, J=16.2 Hz, 1H, olefin), 7.13 (d, J=8.8 Hz, 1H, 5-pyridyl), 6.79 (d, J=8.8 Hz, 1H, 4-pyridyl), 4.06 (t, J=6.6 Hz, 2H, OCH$_2$), 3.81 (s, 3H, CO$_2$CH$_3$), 2.45 (s, 3H, CH$_3$), 1.92–0.85 (m, 23H, aliphatic); MS (CI): 378.2 (M+H).

5(e) 2-(E-2-Carboxymethylethenyl)-3-dodecyloxy-6-(hydroxymethyl)pyridine.

2-(E-2-Carboxymethylethenyl)-3-dodecyloxy-6-methylpyridine N-oxide obtained above was suspended in dry dimethylformamide (20 mL) and cooled to 0∞C. under an argon atmosphere. To this was slowly added trifluoroacetic anhydride (8.5 mL, 60.2 mmol). The reaction was stirred at 0∞C. for 10 minutes and then at room temperature for 16 hours; thin layer chromatography indicated that two reaction products were present (alcohol and trifluoroacetate). The reaction solution was slowly added to a cooled (0∞C.) saturated aqueous Na$_2$CO$_3$ solution (100 mL). The aqueous solution was extracted with ethyl acetate (2×50 mL) and the combined ethyl acetate extracts were washed with H$_2$O (2×20 mL) and brine and dried (MgSO$_4$); the solvent was removed in vacuo. The product mixture was dissolved in methanol (20 mL), treated with anhydrous K$_2$CO$_3$ (500 mg), and vigorously stirred for 20 minutes. The reaction was diluted with ethyl acetate (75 mL) and washed with H$_2$O (30 mL). The aqueous phase was extracted with ethyl acetate (2×20 mL) and the combined ethyl acetate extracts were washed with brine (2×20 mL) and dried (MgSO$_4$). Purification by flash column chromatography (silica, 25% ethyl acetate in petroleum ether) gave a colorless solid: $^1$H NMR (250 MHz, CDCl$_3$): δ8.09 (d, J=15.8 Hz, 1H, olefin), 7.24 (d, J=8.6 Hz, 1H, 5-pyridyl), 7.16 (d, J=8.6 Hz, 1H, 4-pyridyl), 7.03 (d, J=15.8 Hz, 1H, olefin), 4.69 (d, J=4.2 Hz, 2H, CH$_2$), 4.03 (t, J=6.6 Hz, 2H, OCH$_2$), 3.82 (s, 3H, CO$_2$CH$_3$), 3.61 (t, J=4.2 Hz, 1H, OH), 1.91–0.85 (m, 23H, aliphatic); MS (CI): 378.3 (M+H).

5(f) 2-(E-2-Carboxymethylethenyl)-3-dodecyloxy-6-(chloromethyl)pyridine hydrochloride.

2-(E-2-Carboxymethylethenyl)-3-dodecyloxy-6-(hydroxymethyl)pyridine (250 mg, 0.662 mmol) was dissolved in dry toluene (10 mL) under an argon atmosphere and cooled to 0∞C. Thionyl chloride (0.50 mL, 6.85 mmol) was slowly added and the solution was stirred at 0∞C. for 30 minutes followed by 1 h at room temperature. The solvent and excess thionyl chloride were removed at reduced pressure. The crude hydrochloride salt was then used directly in the next step without further purification.

5(g) Methyl 3-[1-thia-2-[2-(E-2-carboxymethylethenyl)-3-dodecyloxy-6-pyridyl]ethyl]benzoate.

2-(E-2-Carboxymethylethenyl)-3-dodecyloxy-6-(chloromethyl)pyridine hydrochloride (0.662 mmol), prepared as previously described, was dissolved in dry dimethylformamide (1 mL) and sequentially treated with methyl 3-mercaptobenzoate (167 mg, 0.993 mmol), anhydrous Cs$_2$CO$_3$ (970 mg, 2.98 mmol), and tetrabutylammonium iodide (25 mg, 0.068 mmol) under an argon atmosphere. The reaction was heated at 65∞C. for 45 minutes. Upon cooling to room temperature the reaction was diluted with ethyl acetate (30 mL) and washed with H$_2$O (2'15 mL) and brine and dried (MgSO$_4$). Purification by flash column chromatography (silica, petroleum ether: CH$_2$Cl$_2$:ethyl acetate, 70:25:5) gave a colorless oil: $^1$H NMR (250 MHz, CDCl$_3$): δ8.04 (s, 1H, 2-phenyl), 8.03 (d, J=15.7 Hz, 1H, olefin), 7.81 (d, J=7.9 Hz, 1H, 4-phenyl), 7.52 (d, J=7.9 Hz, 1H, 6-phenyl), 7.31 (dd, J=7.9 Hz, 5-phenyl), 7.29 (d, J=8.6 Hz, 1H, 5-pyridyl), 7.12 (d, J=8.6 Hz, 1H, 4-pyridyl), 6.98 (d, J=15.7 Hz, 1H, olefin), 4.26 (s, 2H, CH$_2$S), 3.97 (t, J=6.6 Hz, 2H, OCH$_2$), 3.90 (s, 3H, CO$_2$CH$_3$), 3.81 (s, 3H, CO$_2$CH$_3$), 1.85–0.85 (m, 23H, aliphatic).

Proceeding in a similar manner, but substituting the appropriate thiol for 3-mercaptobenzoate, and using known chemistry where appropriate, the following compounds were made:

N-[3-[1-thia-2-[2-(E-2-carboxyethenyl)-3-(8-(4-methoxyphenyl)octyloxy)-6-pyridyl]ethyl]phenyl] oxamic acid, dilithium salt, 3-[1-thia-2-[2-(E-2-carboxyethenyl)-3-(8-(4-methoxyphenyl)octyloxy)-6-pyridyl]ethyl]benzene, lithium salt, 3-[1-thia-2-[2-(E-2-carboxyethenyl)-3-(8-(4-methoxyphenyl)octyloxy)-6-pyridyl]ethyl]anisole, lithium salt, N-[3-[1-thia-2-[2-(E-2-carboxyethenyl)-3-(8-(4-methoxyphenyl)octyloxy)-6-pyridyl]ethyl]phenyl]benzene-sulfonamide, dilithium salt N-[3-[1-thia-2-[2-(E-2-carboxyethenyl)-3-(8-(4-methoxyphenyl)octyloxy)-6-pyridyl]ethyl]phenyl]-trifluoromethane-sulfonamide, dilithium salt, and 3-[1-thia-2-[2-(E-2-carboxyethenyl)-3-(8-(4-methoxyphenyl)octyloxy)-6-pyridyl]ethyl]benzoic acid, dilithium salt.

5(h) Methyl 3-[1-oxythia-2-[2-(E-2-carboxymethylethenyl)-3-dodecyloxy-6-pyridyl]ethyl]benzoate.

Methyl 3-[1-thia-2-[2-(E-2-carboxymethylethenyl)-3-dodecyloxy-6-pyridyl]ethyl]benzoate (320 mg, 0.606 mmol) was dissolved in dry $CH_2Cl_2$ (2.5 mL) and cooled to 0∞C. 85% m-Chloroperoxybenzoic acid (130 mg, 0.64 mmol) was added and the solution was stirred for 10 minutes at 0∞C. The reaction was diluted with ethyl acetate (60 mL) and washed with saturated aqueous $NaHCO_3$ (2×20 mL) and brine and dried ($MgSO_4$). Purification by flash colunto chromatography (silica, $CH_2Cl_2$:petroleum ether:ethyl acetate, 50:25:25) gave a colorless solid: $^1$H NMR (250 MHz, $CDCl_3$): δ8.11 (d, J=7.9 Hz, 1H, 4-phenyl), 8.10 (s, 1H, 2-phenyl), 7.94 (d, J=15.7 Hz, 1H, olefin), 7.67 (d, J=7.9 Hz, 1H, 6-phenyl), 7.53 (dd, J=7.9 Hz, 1H, 5-phenyl), 7.19 (d, J=8.6 Hz, 1H, 5-pyridyl), 7.14 (d, J=8.6 Hz, 1H, 4-pyridyl) 6.68 (d, J=15.7 Hz, 1H, olefin), 4.21 (d, J=12.5 Hz, 1H, CHS), 4.15 (d, J=12.5 Hz, 1H, CH'S), 3.99 (t, J=6.6 Hz, 2H, $OCH_2$), 3.93 (s, 3H, $CO_2CH_3$), 3.81 (s, 3H, $CO_2CH_3$), 1.87–0.85 (m, 23H, aliphatic); Anal. Calcd. for $C_{30}H_{41}O_6NS$: C, 66.27; H, 7.60; N, 2.58, found: C, 65.97; H, 7.22; N, 2.46; MS (CI): 544.3 (M+H).

5(i) 3-[1-Oxythia-2-[2-(E-2-carboxyethenyl)-3-dodecyloxy-6-pyridyl]ethyl]benzoic acid dilithium salt Methyl 3-[1-oxythia-2-[2-(E-2-carboxymethylethenyl)-3-dodecyloxy-6pyridyl]ethyl]benzoate (120 mg, 0.221 mmol) was dissolved in tetrahydrofuran (1.3 mL) and methanol (0.66 mL) under an argon atmosphere and treated with 1M LiOH (0.66 mL, 0.66 mmol). The reaction was stirred at room temperature for 18 hours. The tetrahydrofuran and methanol were removed under reduced pressure and the product was purified by Reversed Phased MPLC (RP-18 silica, 10–65% methanol in $H_2O$) and isolated by lyophilizafion to give a colorless amorphous solid: $^1$H NMR (250 MHz, $CD_3OD$): δ8.27 (s, 1H, 2-phenyl), 8.11 (d, J=7.9 Hz, 1H, 4-phenyl), 7.77 (d, J=15.7 Hz, 1H, olefin), 7.60 (d, J=7.9 Hz, 1H, 6-phenyl), 7.58 (dd, J=7.9 Hz, 1H, 5-phenyl), 7.27 (d, J=8.6 Hz, 1H, 5-pyridyl), 7.04 (d, J=15.7 Hz, 1H, olefin), 7.01 (d, J=8.6 Hz, 1H, 4-pyridyl), 4.33 (d, J=12.5 Hz, 1H, CHS), 4.25 (d, J=12.5 Hz, 1H, CH'S), 4.04 (t, J=6.5 Hz, 2H, $OCH_2$), 1.88–0.86 (m, 23H, aliphatic); Anal. Calcd. for $C_{28}H_{35}O_6NSLi_2 \cdot 2H_2O$: C, 59.68; H, 6.97; N, 2.49, found: C, 59.49; H, 6.98; N 2.58; FAB-MS: (+ve), 528.5 (M+H).

EXAMPLE 6

3-[1-Dioxythia-2-[2-(E-2-carboxyethenyl)-3-dodecyloxy -6-pyridyl]ehtyl]benzoic acid, dilithium salt 6(a) Methyl 3-[1-dioxythia-2-[2-(E-2-carboxymethyl-ethenyl)-3-dodecyloxy-6-pyridyl]ethyl]benzoate Methyl 3-[1-thia-2-[2-(E-2-carboxymethyethenyl)-3-dodecyloxy-6-pyridyl]ethyl]benzoate (107 mg, 0.197 mmol) was dissolved in dry $CH_2Cl_2$ (2 mL), cooled to 0∞C., and treated with 85% m-chloroperoxybenzoic acid (44 mg, 0.217 mmol). The reaction was stirred at 0∞C. for 1.5 hours. The reaction was diluted with ethyl acetate (30 mL) and washed with saturated aqueous $NaHCO_3$ (15 mL) and brine and dried ($MgSO_4$). The product was purified by flash column chromatogrphy (silica, petroleum ether:$CH_2Cl_2$:ethyl acetate, 60:25:15) to give a colorless solid: $^1$H NMR (250 MHz, $CDCl_3$): δ8.30 (s, 1H, 2-phenyl), 8.26 (d, J=7.7 Hz, 1H, 4-phenyl), 7.83 (d, J=7.7 Hz, 1H, 6-phenyl), 7.82 (d, J=15.7 Hz, 1H, olefin), 7.55 (dd, J=7.7 Hz, 1H, 5-phenyl), 7.42 (d, J=8.6 Hz, 1H, 5-pyridyl), 7.21 (d, J=8.6 Hz, 1H, 4-pyridyl), 6.28 (d, J=15.7 Hz, 1H, olefin), 4.52 (s, 2H, $CH_2SO_2$), 4.00 (t, J=6.6 Hz, 2H, $OCH_2$), 3.92 (s, 3H, $CO_2CH_3$), 3.78 (s, 3H, $CO_2CH_3$), 1.87–0.85 (m, 23H, aliphatic); Anal. Calcd. for $C_{30}H_{41}O_7NS$: C, 64.38; H, 7.38; N, 2.50, found: C, 64.71; H, 7.41; N, 2.57; MS (CI): 560.3 (M+H).

6(b) 3-[1-Dioxythia-2-[2-(E-2-carboxyethenyl)-3-dodecyloxy-6-pyridyl]ethyl]benzoic acid, dilithium salt.

Methyl 3-[1-dioxythia-2-[2-(E-2-carboxymethylethenyl)-3-dodecyloxy-6-pyridyl]ethyl]benzoate (20, 170 mg, 0.303 mmol) was dissolved in tetrahydrofuran (3.0 mL) and methanol (1.0 mL) and treated with 1M LiOH (1.0 mL, 1.0 mmol). The reaction was stirred at room temperature for 24 hours. The tetrahydrofuran and methanol were removed under reduced pressure and the product was purified by Reversed Phased MPLC (RP-18 silica, 10–65% methanol in $H_2O$) and isolated by lyophilization to give a colorless amorphous solid: $^1$H NMR (250 MHz, $CD_3OD$): δ8.40 (s, 1H, 2-phenyl), 8.22 (d, J=7.9 Hz, 1H, 4-phenyl), 7.69 (d, J=7.9 Hz, 1H, 6-phenyl), 7.67 (d, J=15.7 Hz, 1H, olefin), 7.53 (dd, J=7.9 Hz, 1H, 5-phenyl), 7.30 (d, J=8.6 Hz, 1H, 5-pyridyl), 7.18 (d, J=8.6 Hz, 1H, 4-pyridyl), 6.85 (d, J=15.7 Hz, 1H, olefin), 4.62 (s, 2H, $CH_2SO_2$), 4.03 (t, J=6.5 Hz, 2H, $OCH_2$), 1.87–0.86 (m, 23H, aliphatic); Anal. Calcd. for $C_{28}H_{35}O_7NSLi_2 \cdot \frac{3}{4}H_2O$: C, 58.48; H, 6.74; N, 2.44, found: C, 58.58; H, 6.74; N, 2.67; FAB-MS: (+ve), 544.3 (M+H); (–ve), 536.2 (M—Li).

EXAMPLE 7

4-[1-Oxythia-2-[2-(E-2-carboxyethenyl)-3-dodecyloxy-6-pyridyl]ethyl]benzoic acid, dilithium salt 4-[1-Oxythia-2-[2-(E-2-carboxyethenyl)-3-dodecyloxy-6-pyridyl)]ethyl]benzoic acid, dilithium salt was prepared according to the procedure described for 3-[1-oxythia-2-[2-(E-2-carboxyethenyl)-3-dodecyloxy-6-pyridyl]ethyl] benzoic acid, dilithium salt substituting methyl 4-mercaptobenzoate for methyl 3-mercaptobenzoate.

7(a) Methyl 4-[1-thia-2-[2-(E-2-carboxymethylethenyl)-3-dodecyloxy-6-pyridyl]ethyl]benzoate $^1$H NMR (250 MHz, $CDCl_3$): δ8.05 (d, J=15.7 Hz, 1H, olefin), 7.90 (d, J=8.5 Hz, 2H, aryl), 7.37 (d, J=8.5 Hz, 2H, aryl), 7.35 (d, J=8.6 Hz, 1H, 5-pyridyl), 7.14 (d, J=8.6 Hz, 1H, 4-pyridyl), 7.01 (d, J=15.7 Hz, 1H, olefin), 4.29 (s, 2H, $CH_2S$), 3.98 (t, J=6.5 Hz, 2H, $OCH_2$), 3.88 (s, 3H, $CO_2CH_3$), 3.86 (s, 3H, $CO_2CH_3$), 1.86–0.85 (m, 23H, aliphatic).

7(b) Methyl 4-[1-oxythia-2-[2-(E-2-carboxymethylethenyl)-3-dodecyloxy-6-pyridyl]ethyl]benzoate.

mp. 107–109∞C.; $^1$H NMR (250 MHz, $CDCl_3$) δ8.13 (d, J=8.5 Hz, 2H, aryl), 7.95 (d, J=15.7 Hz, 1H, olefin), 7.56 (d, J=8.5 Hz, 2H, aryl), 7.18 (d, J=8.6 Hz, 1H, 5-pyridyl), 7.11 (d, J=8.6 Hz, 1H, 4-pyridyl), 6.62 (d, J=15.7 Hz, 1H, olefin), 4.22 (d, J=12.5 Hz, 1H, CHS), 4.13 (d, J=12.5 Hz, 1H, CH'S), 4.03 (t, J=6.5 Hz, 2H, $OCH_2$), 3.99 (s, 3H, $CO_2CH_3$), 3.78 (s, 3H, $CO_2CH_3$), 1.92–0.85 (m, 23H, aliphatic); Anal. Calcd. for $C_{30}H_{41}O_6NS$: C, 66.27; H, 7.60; N, 2.58, found: C, 65.99; H, 7.55; N, 2.27; MS (CI): 544 (M+H).

7(c) 4-[1-Oxythia-2-[2-(E-2-carboxyethenyl)-3-dodecyloxy-6-pyridyl]ethyl]benzoic acid, dilithium salt.

mp. 205–207°C. (dec.); $^1$H NMR (250 MHz, CD$_3$OD): δ8.09 (d, J=8.5 Hz, 2H, aryl), 7.78 (d, J=15.7 Hz, 1H, olefin), 7.59 (d, J=8.5 Hz, 2H, aryl), 7.26 (d, J=8.6 Hz, 1H, 5-pyridyl), 7.07 (d, J=15.7 Hz, 1H, olefin), 6.98 (d, J=8.6 Hz, 1H, 4-pyridyl), 4.33 (d, J=12.5 Hz, 1H, CHS), 4.22 (d, J=12.5 Hz, 1H, CH'S), 4.04 (t, J=6.5 Hz, 2H, OCH$_2$), 1.88–0.86 (m, 23H, aliphafic); Anal. Calcd. for C$_{28}$H$_{35}$O$_6$NSLi$_2$.$\frac{3}{2}$H$_2$O: C, 60.64; H, 6.91; N, 2.53, found: C, 60.41; H, 6.73; N, 2.60; FAB-MS: (+ve), 528.5 (M+H).

EXAMPLE 8

2-[1-Oxythia-2-[2-(E-2-carboxyethenyl)-3-dodecyloxy-6-pyridyl]ethyl]benzoic acid, dilithium salt.

2-[1-Oxythia-2-[2-(E-2-carboxyethenyl)-3-dodecyloxy-6-pyridyl]ethyl]benzoic acid, dilithium salt, was prepared according to the procedure described for 3-[1-oxythia- 2-[2-(E-2-carboxyethenyl)-3-dodecyloxy-6-pyridyl]ethyl] benzoic acid, dilithium salt, but substituting methyl 2-mercaptobenzoate for methyl 3-mercaptobenzoate.

8(a) Methyl 2-[1-thia-2-[2-(E-2-carboxymethylethenyl)-3-dodecyloxy-6-pyridyl]ethyl]benzoate $^1$H NMR (250 MHz, CDCl$_3$): δ8.07 (d, J=15.7 Hz, 1H, olefin), 7.96 (d, J=7.8 Hz, 1H, 3-phenyl), 7.56 (d, J=7.8 Hz, 1H, 6-phenyl), 7.43 (d, J=8.6 Hz, 1H, 5-pyridyl), 7.42 (m, 1H, aryl), 7.14 (d, J=8.6 Hz, 1H, 4-pyridyl), 7.10 (m, 1H, aryl), 7.06 (d, J=15.7 Hz, 1H, olefin), 4.27 (s, 2H, CH$_2$S), 3.98 (t, J=6.6 Hz, 2H, OCH$_2$), 3.91 (s, 3H, CO$_2$CH$_3$), 3.83 (s, 3H, CO$_2$CH$_3$), 1.86–0.86 (m, 23H, aliphatic).

8(b) Methyl 2-[1-oxythia-2-[2-(E-2-carboxymethylethenyl)-3-dodecyloxy-6-pyridyl]ethyl]benzoate.

mp. 60–62°C.;
$^1$H NMR (250 MHz, CDCl$_3$): δ8.13 (d, J=7.8 Hz, 1H, 3-phenyl), 7.87 (d, J=15.7 Hz, 1H, olefin), 7.68 (d, J=7.8 Hz, 1H, 6-phenyl), 7.53 (m, 2H, aryl), 7.33 (d, J=8.6 Hz, 1H, 5-pyridyl), 7.16 (d, J=8.6 Hz, 1H, 4-pyridyl), 6.46 (d, J=15.7 Hz, 1H, olefin), 4.42 (d, J=12.6 Hz, 1H, CHS), 4.30 (d, J=12.6 Hz, 1H, CH'S), 4.03 (s, 3H, CO$_2$CH$_3$), 4.0 (t, J=6.6 Hz, 2H, OCH$_2$), 3.81 (s, 3H, CO$_2$CH$_3$), 1.87–0.85 (m, 23H, aliphatic); Anal. Calcd. for C$_{30}$H$_{41}$O$_6$NS: C, 66.27; H, 7.60; N, 2.58, found: C, 66.37; H, 7.67; N, 2.56; MS (CI): 544 (M+H).

8(c) 2-[1-oxythia-2-[2-(E-2-carboxyethenyl)-3-dodecyloxy-6-pyridyl]ethyl]benzoic acid, dilithium salt.

mp. 235°C. (dec); $^1$H NMR (250 MHz, CD$_3$OD): δ8.07 (d, J=7.8 Hz, 1H, 3-phenyl), 7.76 (d, J=7.8 Hz, 1H, 6-phenyl), 7.71 (d, J=15.7 Hz, 1H, olefin), 7.53 (m, 2H, aryl), 7.31 (s, 2H, pyridyl), 6.92 (d, J=15.7 Hz, 1H, olefin), 4.72 (d, J=12.6 Hz, 1H, CHS), 4.12 (d, J=12.6 Hz, 1H, CH'S), 4.05 (t, J=6.5 Hz, 2H, OCH$_2$), 1.88–0.86 (m, 23H, aliphatic); FAB-MS: (+ve), 528.3 (M+H).

In addition, by subsituting the appropriate reagents and intermediates for those recited in 4(a)–4(c), and by using chemistry available in the art, the following compounds were made:

3-[1-oxythia-2-[2-(E-2-carboxyethenyl)-3-(8-(4-methoxyphenyl)octyloxy)-6-pyridyl]ethyl]benzoic acid, dilithium salt, N-[3-[1-oxythia-2-[2-(E-2-carboxyethenyl)-3-dodecyloxy-6-pyridyl]ethyl]phenyl]trifluoro-methanesulfonamide, dilithium salt, N-[3-[1-oxythia-2-[2-(E-2-carboxyethenyl)-3-(8-(4-methoxyphenyl)octyloxy)-6-pyridyl]ethyl]phenyl] trifluoro-methanesulfonamide, dilithium salt, N-[3-[1-oxythia-2-[2-(E-2-carboxyethenyl)-3-(8-(4-methoxyphenyl)octyloxy)-6-pyridyl]ethyl]phenyl]-benzenesulfonamide, dilithium salt 3-[1-oxythia-2-[2-(E-2-carboxyethenyl)-3-(8-(4-methoxyphenyl)octyloxy)-6-pyeidyl]ethyl]anisole, lithium salt, 3-[1-oxythia-2-[2-(E-2-carboxyethenyl)-3-(8-(4-methoxyphenyl)octyloxy)-6-pyridyl ethyl]benzene, lithium salt.

EXAMPLE 9

3-[1-Oxa-2-[2-(E-2-carboxyethenyl)-3-dodecyloxy-6-pyridyl]ethyl]benzoic acid, dilithium salt 9(a) Methyl 3-[1-oxa-2-[2-(E-2-carboxymethylethenyl)-3-dodecyl-oxy-6-pyridyl]ethyl]benzoate.

2-(E-2-Carboxymethylethenyl)-3-dodecyloxy-6-(chloromethyl)pyridine hydrochloride, prepared as per Example 1(a)–1(f), was dissolved in dry dimethylformamide (2 mL) and treated sequentially with methyl 3-hydroxybenzoate (152 mg, 1.00 mmol, Aldrich), anhydrous K$_2$CO$_3$ (500 mg, 3.62 mmol), and tetrabutylammonium iodide (24.4 mg, 0.066 mmol) under an argon atmosphere. The reaction was heated at 90°C. for 1 hour. Upon cooling to room temperature the reaction was diluted with ethyl acetate (50 mL) and washed with H$_2$O (3×15 mL) and brine and dried (MgSO$_4$). Purification by flash colunto chromatography (silica, CH$_2$Cl$_2$: petroleum ether: ethyl acetate, 50:48:2) gave a colorless solid: $^1$H NMR (250 MHz, CDCl$_3$): δ8.09 (d, J=15.8 Hz, 1H, olefin), 7.69 (s, 1H, 2-phenyl), 7.65 (d, J=7.9 Hz, 1H, 4-phenyl), 7.44 (d, J=8.6 Hz, 1H, 5-pyridyl), 7.34 (dd, J=7.9 Hz, 1H, 5-phenyl), 7.22 (d, J=8.6 Hz, 1H, 4-pyridyl), 7.16 (d, J=7.9 Hz, 1H, 6-phenyl), 7.07 (d, J=15.8 Hz, 1H, olefin), 5.18 (s, 2H, CH$_2$), 4.02 (t, J=6.6 Hz, 2H, OCH$_2$), 3.91 (s, 3H, CO$_2$CH$_3$), 3.82 (s, 3H, CO$_2$CH$_3$), 1.90–0.88 (m, 23H, aliphatic); Anal. Calcd. for C$_{30}$H$_{41}$O$_6$N.⅛ mole toluene: C, 70.88; H, 8.09; N, 2.68, found: C, 70.98; H, 8.19; N, 2.64; MS (CI): 512.4 (M+H).

9(b) 3-[1-Oxa-2-[2-(E-2-carboxyethenyl)-3-dodecyloxy-6-pyridyl]ethyl]benzoic acid, dilithium salt.

Methyl 3-[1-oxa-2-[2-(E-2-carboxymethylethenyl)-3-dodecyloxy-6-pyridyl]ethyl]benzoate (80 mg, 0.156 mmol) was dissolved in tetrahydrofuran (1.34 mL) and methanol (0.50 mL) and treated with 1M LiOH (0.50 mL, 0.50 mmol). The reaction was stixred at room temperature for 20 hours. The tetrahydrofuran and methanol were removed at reduced pressure and the product was purified by Reversed Phased MPLC (RP-18 silica, 10–65% methanol in H$_2$O) and isolated by lyophilization to give a colorless amorphous solid: $^1$H NMR (250 MHz, CD$_3$OD): δ7.81 (d, J=15.7 Hz, 1H, olefin), 7.62 (s, 1H, 2-phenyl), 7.56 (d, J=7.9 Hz, tH, 4-phenyl), 7.44 (d,,J=8.6 Hz, 1H, 5-pyridyl), 7.40 (d, J=8.6 Hz, 1H, 4-pyridyl), 726 (rid, J=7.9 Hz, 1H, 5-phenyl), 7.07 (d, J=15.7 Hz, 1H, olefin), 7.05 (d, J=7.9 Hz, 1H, 6-phenyl), 5.13 (s, 2H, CH$_2$), 4.07 (t, J=6.5 Hz, 2H, OCH$_2$), 1.89–0.89 (m, 23H, aliphatic); Anal. Calcd. for C$_{28}$H$_{35}$O$_6$NLi$_2$.$\frac{1}{2}$H$_2$O: C, 62.22; H, 7.46; N, 2.59, found: C, 62.06: H, 7.37; N, 2.82: FAB-MS: (+ve), 502.3 (M+Li); (–ve), 488.2 (M—Li).

9(c) 3-[1-Oxa-2-[2-(E-2-carboxyethenyl)-3-dodecyloxy-6-pyridyl]ethyl]benzoic acid, N-oxid, dilithium salt.

Methyl 3-[1-oxa-2-[2-(E-2-carboxymethylethenyl)-3-dodecyloxy-6-pyridyl]ethyl]benzoate, N-oxide.

Methyl 3-[1-oxa-2-[2-(E-2-carboxymethylethenyl)-3-dodecyloxy-6-pyridyl]ethyl]benzoate (130 mg, 0.254 mmol) was dissolved in dry CH$_2$Cl$_2$ (1.5 mL), cooled to 0∞C., and treated with 85% m-chloroperoxybenzoic acid (57 mg, 0.28 mmol). The reaction was stirred at 0∞C. for 10 minutes and then for 20 hours at room temperature. The reaction was diluted with ethyl acetate (30 mL) and washed with saturated aqueous NaHCO$_3$ (15 mL), H$_2$O (10 mL), and brine and dried (MgSO$_4$). The product was purified by flash column chromatography (silica, CH$_2$Cl$_2$: petroleum ether:ethyl acetate, 50:40:10) to give a colorless solid. $^1$H NMR (250 MHz, CDCl$_3$): δ8.24 (d, J=16.2 Hz, 1H, olefin), 7.71 (d, J=8.0 Hz, 1H, 4-phenyl), 7.68 (s, 1H, 2-phenyl), 7.60 (d, J=16.2 Hz, 1H, olefin), 7.46 (d, J=9.0 Hz, 1H, 5-pyridyl), 7.38 (dd, J=8.0 Hz, 1H, 5-phenyl), 7.22 (d, J=8.0 Hz, 1H, 6-phenyl), 6.9 (d, J=9.0 Hz, 1H, 4-pyridyl), 5.32 (s, 2H, CH$_2$), 4.10 (t, J=6.6 Hz, 2H, OCH$_2$), 3.92 (s, 3H, CO$_2$CH$_3$), 3.83 (s, 3H, CO$_2$CH$_3$), 1.94–0.88 (m, 23H, aliphatic); Anal. Calcd. for C$_{30}$H$_{41}$O$_7$N: C, 68.29; H, 7.83; N, 2.65, found: C, 68.27; H, 7.82; N, 2.66; MS (CI): 528.3 (M+H).

9(d) 3-[1-Oxa-2-[2-(E-2-carboxyethenyl)-3-dodecyloxy-6-pyrid$_e$]ethyl]benzoic acid N-oxide, dilithium salt.

Methyl 3-[1-oxa-2-[2-(E-2-carboxymethylethenyl)-3-dodecyloxy-6-pyridyl]ethyl]benzoate, N-oxide (110 mg, 0.208 mmol) was dissolved in tetrahydrofuran (2 mL) and methanol (0.65 mL) and treated with 1M LiOH (0.65 mL). The reaction was stirred at room temperature for 20 hours. The tetrahydrofuran and methanol were removed under reduced pressure and the product was purified by Reversed Phase MPLC (RP-18 silica, 10–65% methanol in H$_2$O) and isolated by lyophilization to give a colorless amorphous solid. $^1$H NMR (250 MHz, CD$_3$OD): δ7.99 (d, J=16.2 Hz, 1H, olefin), 7.64 (s, 1H, 2-phenyl), 7.60 (d, J=8.0 Hz, 1H, 4-phenyl), 7.52 (d, J=9.0 Hz, 1H, 5-pyridyl), 7.45 (d, J=16.2 Hz, 1H, olefin), 7.30 (d, J=9.0 Hz, 1H, 4-pyridyl), 7.29 (dd, J=8.0 Hz, 1H, 5-phenyl), 7.08 (d, J=8.0 Hz, 1H, 6-phenyl), 5.30 (s, 2H, CH$_2$), 4.17 (t, J=6.6 Hz, 2H, OCH$_2$), 1.95–0.86 (m, 23H, aliphatic); Anal. Calcd. for C$_{28}$H$_{35}$O$_7$NLi$_2$.3H$_2$O: C, 59.47; H, 7.31; N, 2.48, found: C, 59.46; H, 6.91: N 2.50; FAB-MS: (+ve), 512.2 (M+H); (–ve), 504.5 (M—Li).

Proceeding in a similar manner, but substituting the appropriate intermediates, the following compounds were made:

3-[1-oxa-2-[2-(E-2-carboxyethenyl)-3-(8-(4-methoxyphenyl)-octyloxy)-6-pyridyl]ethyl]benzoic acid, N-oxide, dilithium salt, 3-[1-oxa-2-[2-(E,E-4-carboxybuta-1,3-dienyl)-3-(8-(4-methoxyphenyl)octyloxy)-6-pyridyl]ethyl]benzoic acid, N-oxide, dilithium salt, 3-[1-oxa-2-[2-(E-2-carboxyethenyl)-3-(8-(4-methoxyphenyl)-nonyloxy)-6-pyridyl]ethyl]benzoic acid, N-oxide, dilithium salt, N-[3-[1-oxa-2-[2-(E-2-carboxyethenyl)-3-(8-(4-methoxyphenyl)octyloxy)-6-pyridyl]ethyl]phenyl] trifluoromethane-sulfonamide, N-oxide, dilithium salt, 4-methoxy-3-[1-oxa-2-[2-(E-2-carboxyethenyl)-3-(8-(4-methoxyphenyl)octyloxy)-6-pyridyl]ethyl]benzoic acid, dilithium salt, N-[3-[1-oxa-2-[2-(E-2-carboxyethenyl)-3-(8-(4-methoxyphenyl)octyloxy)-6pyrdyl]ethyl]phenyl] acetamide, N-oxide, lithium salt, 3-[1-oxa-2-[2-(E-2-carboxyethenyl)-3-(7-(4-methoxybenzyl-sulfonyl)heptyloxy)-6-pyridyl]ethyl] benzoic acid, N-oxide, dilithium salt, 3-[1-oxa-2-[2-(E-2-carboxyethenyl)-3-(7-(4-methoxyphenyl-sulfonyl)heptyloxy)-6-pyridyl]ethyl] benzoic acid, N-oxide, dilithium salt, 3-[1-oxa-2-[2-(E-2<diethylphosphonoethenyl)-3-dodecyloxy-6-pyridyl]ethyl]benzoic acid, N-oxide, lithium salt, N-[3-[1-oxa-2-[2-(E-2-carboxyethenyl)-3-(8-(4-methoxyphenyl)octyloxy)-6-pyridyl]ethyl]phenyl] oxamic acid, dilithium salt, N-[6-methoxy-3-[1-oxa-2-[2-(E-2-carboxyethenyl)-3-(8-(4-methoxyphenyl)octyloxy)-6-pyridyl]ethyl]phenyl]-trifluommethane-sulfonamide, N-oxide, dilithium salt, N-[6-methoxy-3-[1-oxa-2-[2-(E-2-carboxyethenyl)-3-(8-(4-methoxyphenyl)octyloxy)-6-pyridyl]ethyl]phenyl]-trifluoromethane-sulfonamide, dilithium salt, N-[3-[1-oxa-2-[2-(E-2-carboxyethenyl)-3-(8-(4-methoxyphenyl)octyloxy)-6-pyridyl]ethyl]phenyl] oxamic acid, N-oxide, dilithium salt, 3-[1-oxa-2-[2-(E-2-ethylphosphonoethenyl)-3-dodecyloxy-6-pyridyl]ethyl]benzoic acid, N-oxide, dilithium salt, 5-[1-oxa-2-[2-(E-2-carboxyethenyl)-3-(8-(4-methoxyphenyl)octyloxy)-6-pyridyl]ethyl]benzene, lithium salt, 3-[1-oxa-2-[2-(E-2-carboxyethenyl)-3-(8-(4-methoxyphenyl)octyloxy)-6-pyridyl]ethyl]phenylurea, lithium salt, 3-[1-oxa-2-[2-(E-2-carboxyethenyl)-3-(8-(4-methoxyphenyl)octyloxy)-6-pyridyl]ethyl]benzonitrile, lithium salt, 3-[1-oxa-2-[2-(E-2-carboxyethenyl)-3-(8-(4-methoxyphenyl)octyloxy)-6-pyridyl]ethyl]phenol, lithium salt, and 3-[1-oxa-2-[2-(E-2-carboxyethenyl)-3-(8-(4-methoxyphenyl)octyloxy)-6-pyridyl]ethyl]benzamide, lithium salt.

EXAMPLE 10

1-Oxa-2-[2-(E-2-carboxyethenyl)-3-(8-(4-methoxyphenyl)octyloxy)-6-pyridyl]ethyl]aniline lithium salt 10(a) 7-Octyn-1-ol.

35% KH in mineral oil (27 g, 240 mmol) under an argon atmosphere was washed with hexane and treated dropwise with 1,3-diaminopropane. The mixture was stirred at room temperature until it became homogeneous. The flask was cooled to 0° C. and 3-octyn-1-ol (10 g, 79 mmol, Lancaster Synthesis) was slowly added. The reaction was then stirred at room temperature for 18 hours. The reaction was quenched with H$_2$O (50 mL) and the product was extracted into ether. The organic layer was washed with 10% HCl and brine and dried (MgSO$_4$). Evaporation gave a colorless oil which was used without further purification: $^1$H NMR (90 MHz, CDCl$_3$) δ3.65 (t, J=5 Hz, 2H, O—CH$_2$), 2.23 (m, 2H, CH$_2$), 2.0 (m, 1H, acetylenic), 1.7–1.2 (m, 8H, (CH$_2$)$_4$); IR (neat) n$_{max}$ 3350, 2930, 2125 cm$^{-1}$.

10(b) 7-Octyn-1-$^t$butyldiphenylsilyl ether.

To a cooled (0° C.) solution of 7-octyn-1-ol (9.3 g, 73.7 mmol) in DMF (70 mL) under an argon atmosphere was added imidazole (7.5 g, 110 mmol) followed by the dropwise addition of $^t$butylchlorodiphenylsilane. The reaction was then stirred at room temperature for 2 hours. The reaction solution was diluted with Et$_2$O and washed with H$_2$O and brine and dried (MgSO$_4$). Purification by flash column chromatography (silica, 3% EtOAc in hexane) provided a colorless oil: $^1$H NMR (250 MHz, CDCl$_3$) δ7.7 (d, 4H, aryl), 7.4 (m, 6H, aryl), 3.63 (t, 2H, O—CH$_2$), 2.23 (m, 2H, CH$_2$), 1.97 (t, 1H, acetylenic), 1.6–1.3 (m, 8H, (CH$_2$)$_4$), 1.05 (s, 9H, $^t$butyl); IR (film) n$_{max}$ 3321, 2940, 2125 cm$^{-1}$.

10(c) 8-(4-Methoxyphenyl)-7-octyn-1-$^t$butyldiphenylsilyl ether.

To a flame dried flask containing triethylamine (140 mL) under an argon atmosphere was added 4-iodoanisole (13.3 g, 56.9 mmol), 7-octyn-1-t-butyldiphenylsilyl ether (24.9 g, 68.3 mmol), (Ph$_3$P)$_2$PdCl$_2$ catalyst (93 mg, 1.13 mmol), and CuI (431 mg, 2.27 mmol). The resulting mixture was heated at 50° C. for 4 hours. Upon cooling to room temperature the reaction mixture was filtered, the solids were washed with Et$_2$O and the solvent was evaporated. The residue was diluted with Et2O and washed with 5% HCl, H$_2$, O Na-HCO$_3$, and brine and dried (MgSO$_4$). Purification by flash column chromatography (silica, 2% EtOAc in hexane) gave an orange oil: $^1$H NMR (250 MHz, CDCl$_3$) δ7.7 (d, 4H, aryl), 7.4 (m, 6H, aryl), 7.35 (d, 2H, aryl), 6.8 (d, 2H, aryl), 3.8 (s, 3H, OMe), 3.7 (t, 2H, O—CH$_2$), 2.4 (t, 2H, CH$_2$), 1.7–1.3 (m, 8H, (CH$_2$), 1.05 (s, 9H, $^t$butyl).

10(d) 8-(4-Methoxyphenyl)octan-1-$^t$butyldiphenylsilyl ether.

8-(4-Methoxyphenyl)-7-octyn-1-t-butyldiphenylsilyl ether (30 g, 63.7 mmol) was dissolved in EtOH (125 mL) and EtOAc (125 mL) and treated with 5% Pd-C catalyst (3 g). The reaction was vigorously stirred under an H$_2$ atmosphere (balloon pressure) for 4 hours. The reaction mixture was filtered through a pad of celite and the solvent was evaporated. The resulting pale yellow oil was pure by nmr analysis and was used directly for the next step: $^1$H NMR (250 MHz, CDCl$_3$) δ7.7 (d, 4H, aryl), 7.4 (m, 6H, aryl), 7.05 (d, 2H, aryl), 6.8 (d, 2H, aryl), 3.8 (s, 3H, OMe), 3.6 (t, 2H, O—CH$_2$), 2.5 (t, 2H, benzylic), 1.75–1.3 (m, 12H, (CH$_2$)$_6$), 1.0 (s, 9H, $^t$butyl).

10(e) 8-(4-Methoxyphenyl)octan-1-ol. To a cooled (0° C.) solution of 8-(4-methoxyphenyl)octan-1-$^t$butyldiphenylsilyl ether (63 mmol) was added tetrabutylammonium fluoride (70 mL, 70 mmol; 1M solution in THF). The cooling bath was removed and the reaction was stirred at room temperature for 4.5 hours. The solvent was evaporated and the residue was dissolved in Et$_2$O. This was washed with H$_2$O, 5% HCl, NaHCO$_3$, and brine and dried (MgSO$_4$). Purification by flash column chromatography (silica, 30% EtOAc in hexane) gave a colorless solid: $^1$H NMR (250 MHz, CDCl$_3$) δ7.15 (d, 2H, aryl), 6.86 (d, 2H, aryl), 3.85 (s, 3H, OMe), 3.68 (t, 2H, O—CH$_2$), 2.62 (t, 2H, benzylic), 1.75–1.3 (m, 12H, (CH$_2$)$_6$); MS (CI): 254.2 (M+NH$_4$); mp 47°–49° C.

10(f) 1-Iodo-8-(4-methoxyphenyl)octane.

To a stirred solution of 8-(4-methoxyphenyl)octan-1-ol (12.3 g, 52 mmol) in dry toluene (200 mL) under an argon atmosphere was added triphenylphosphine (17.8 g, 67.6 mmol) and imidazole (10.6 g, 156 mmol). After the imidazole had dissolved I$_2$ (17.1 g, 67.6 mmol) was added. The reaction was then heated at 65° C. for 30 minutes. Upon cooling to room temperature the reaction was concentrated to ¼ volume. The remaining solution was diluted with Et$_2$O and washed with H$_2$O and brine and dried (MgSO$_4$). The solvent was removed and the resulting residue was dissolved in CH$_2$Cl$_2$ and applied to a flash chromatography column (silica). Fludon with 2% EtOAc in hexane provided a colorless oil (slight contamination with triphenylphosphine): $^1$H NMR (250 MHz, CDCl$_3$) δ7.08 (d, J=8.6 Hz, 2H, aryl), 6.82 (d, J=8.6 Hz, 2H, aryl), 3.78 (s, 3H, OMe), 3.17 (t, J=7.4 Hz, 2H, I—CH$_2$), 2.54 (t, J=7.6 Hz, 2H, benzylic), 1.85 (m, 2H, CH$_2$), 1.60 (m, 2H, CH$_2$), 1.31 (m, 8H, aliphatic); MS (CI): 364.2 (M+NH$_4$).

10(g) 3-Hydroxy-6-methyl-2-pyridine carboxaldehyde.

2,6-Lutidine-a$^2$,3-diol (15 g, 107.8 mmol; Aldrich) was suspended in dry CH$_2$Cl$_2$ (200 mL) and treated with MnO$_2$ (47 g, 539 mmol). The reaction was stirred at room temperature for 6 hours. The reaction mixture was filtered through a pad of celite and the solvent was evaporated. The crude aldehyde was obtained as a tan solid and was used directly for the next step: $^1$H NMR (250 MHz, CDCl$_3$) δ10.65 (s, 1H, OH), 10.30 (s, 1H, aldehyde), 7.30 (m, 2H, 4,5-pyridyl), 2.55 (s, 3H, methyl).

10(f) 3-[8-(4-Methoxyphenyl)octyloxy]-6-methyl-2-pyridine carboxaldehyde.

To a solution of 1-iodo-8-(4-methoxyphenyl)octane (16.3 g, 47.1 mmol) in dry DMF (45 mL) under an argon atmosphere was added 3-hydroxy-6-methyl-2-pyridine carboxaldehyde (7.7 g, 56.2 mmol) and anhydrous K$_2$CO$_3$ (32 g, 235 mmol). The reaction was vigorously stirred at 90° C. for 1.5 hours. Upon cooling to room temperature the reaction was diluted with EtOAc and washed with H$_2$O, aq NH$_4$Cl, and brine and dried (MgSO$_4$). Evaporation provided crude aldehyde as a dark oil that was used without further purification.

10(g) 2-(E-2-Carboxymethylethenyl)-3-[8-(4-methoxyphenyl)octyloxy]-6-methylpyridine 3-[8-(4-Methoxyphenyl)octyloxy]-6-methyl-2-pyridine carboxaldehyde obtained above was dissolved in dry toluene (100 mL) under an argon atmosphere and treated with methyl (triphenylphosphoranylidene)acetate (16 g, 48 mmol). The reaction was heated for 1 hour at 50° C. Upon cooling to room temperature the reaction was diluted with EtOAc and washed with H$_2$O and brine and dried (MgSO$_4$). Purification by flash column chromatography (silica, 20% EtOAc in hexane) gave a pale yellow oil: $^1$H NMR (250 MHz, CDCl$_3$) δ8.07 (d, J=15.7 Hz, 1H, olefin), 7.10 (m, 4H, phenyl, 4,5-pyridyl), 7.07 (d, J=15.7 Hz, 1H, olefin), 6.81 (d, J=8.6 Hz, 2H, phenyl), 3.97 (t, J=6.5 Hz, 2H, O—CH$_2$), 3.79 (s, 3H, methyl ester), 3.78 (s, 3H, OMe), 2.54 (t, J=7.6 Hz, 2H, benzylic), 2.48 (s, 3H, methyl), 1.85 (m, 2H, CH$_2$), 1.60 (m, 2H, CH$_2$), 1.37 (m, 8H, aliphatic); MS (CI): 412.3 (M+H).

10(h) 2-(E-2-Carboxymethylethenyl)-3-[-(4-methoxyphenyl)octyloxy]-6-methylpyridine N-oxide.

2-(E-2-Carboxymethylethenyl)-3-[8-(4-methoxyphenyl) octyloxy]-6-methylpyridine (17.1 g, 41.5 mmol) was dissolved in dry CH$_2$Cl$_2$ (105 mL) and cooled to 0° C.; 50% mCPBA (15.8 g, 45.8 mmol) was added in three portions over 10 minutes. The cooling bath was removed and the reaction was stirred for 15 hours at room temperature. The reaction was poured into aqueous NaHCO$_3$ and the product extracted into CH$_2$Cl$_2$. The organic extract was washed with H$_2$O and brine and dried (MgSO$_4$). The crude product was obtained as a yellow solid and was used without further purification.

10(i) 2-(E-2-Carboxymethylethenyl)-3-[8-(4-methoxyphenyl)octyloxy]-6-hydroxymethylpyridine.

2-(E-2-Carboxymethylethenyl)-3-[8-(4-methoxyphenyl) octyloxy]-6-methylpyridine N-oxide obtained above was suspended in dry DMF (130 mL) and cooled to 0° C. under an argon atmosphere. To this was slowly added trifluoroacetic anhydride (56 mL, 400 mmol). The reaction was maintained at 0° C. for 20 minutes followed by 18 hours at room temperature. The reaction solution was slowly added to a solution of saturated aqueous Na$_2$CO$_3$ and stirred for 1 hour. The product was then extracted into EtOAc; the combined organic extracts were washed with H$_2$O and brine and dried (MgSO$_4$). Purification by flash column chromatography (silica, EtOAc:hexane:CH$_2$Cl$_2$, 30:20:50) gave a waxy solid: $^1$H NMR (250 MHz, CDCl$_3$) δ8.08 (d, J=15.7 Hz, 1H, olefin), 7.23 (d, J=8.6 Hz, 1H, 5-pyridyl), 7.16 (d, J=8.6 Hz, 1H, 4-pyridyl), 7.09 (d, J=8.6 Hz, 2H, phenyl), 7.03 (d, J=15.7 Hz, 1H, olefin), 6.82 (d, J=8.6 Hz, 2H, phenyl), 4.69 (d, J=4.1 Hz, 2H, CH$_2$—OH), 4.01 (t, J=6.5 Hz, 2H, O—CH$_2$), 3.82 (s, 3H, methyl ester), 3.78 (s, 3H, OMe), 3.62 (t, J=4.1 Hz, 1H, OH), 2.55 (t, J=7.6 Hz, 2H, benzylic), 1.85 (m, 2H, CH$_2$), 1.58 (m, 2H, CH$_2$), 1.44 (m, 8H, aliphatic); MS (CI): 428.2 (M+H).

10(i) 3-Aminophenol 'butylcarbamate.

3-Aminophenol (2.0 g, 18.3 mmol; Aldrich) was dissolved in $CH_2Cl_2$ (18 mL) and DMF (6 mL) and treated with di-'butyl dicarbonate (5.0 mL, 21.7 mmol). The reaction was stirred under an argon atmosphere for 18 hours. The reaction solution was diluted with EtOAc and washed with $H_2O$ and brine and dried ($MgSO_4$). Purification by flash column chromatography (silica, EtOAc:hexane:$CH_2Cl_2$, 15:60:25) gave a colorless solid: $^1$H NMR (250 MHz, $CDCl_3$) δ7.15 (m, 2H, aryl), 6.72 (m, 1H, aryl), 6.53 (m, 2H, aryl, OH), 6.0 (s, 1H, NH), 1.54 (s, 9H, 'butyl); MS (CI): 210.2 (M+H); mp 95°–97° C.

10(k) 2-(E-2-Carboxymethylethenyl)-3-[8-(4-methoxyphenyl)octyloxy]-6-[(3-phenoxymethyl]pyridine 'butylcarbamate.

To a cooled (0° C.) solution of $SOCl_2$ (0.51 mL, 7.0 mmol) in dry toluene (2 mL) under an argon atmosphere was added a solution of 2-(E-2-carboxymethylethenyl)-3-[8-(4-methoxyphenyl)octyloxy]-6-hydroxymethylpyridine (300 mg, 0.70 mmol) in toluene (5 mL). After 5 minutes the cooling bath was removed and the reaction was stirred for 2 hours at room temperature. The toluene and excess $SOCl_2$ were evaporated. To this was added dry DMF (0.90 mL), 3-aminophenol 'butylcarbamate (209 mg, 1.0 mmol), and anhydrous $Cs_2CO_3$ (1.63 g, 5.0 mmol). The reaction was heated at 90 ° C. under an atmosphere of argon for 2 hours. Upon cooling to room temperature the reaction was diluted with EtOAc and washed with $H_2O$, 10% NaOH, $H_2O$, and brine and dried ($MgSO_4$). Purification by flash column chromatography (silica, EtOAc:hexane:$CH_2Cl_2$, 7:63:30) yielded a colorless oil: $^1$H NMR (250 MHz, $CDCl_3$) δ8.09 (d, J=15.7 Hz, 1H, olefin), 7.44 (d, J=8.6 Hz, 1H, aryl), 7.15 (m, 5H, aryl), 7.05 (d, J=15.7 Hz, 1H, olefin), 6.90 (m, 1H, aryl), 6.82 (d, J=8.6 Hz, 2H, aryl), 6.65 (m, 1H, aryl), 6.51 (s, 1H, NH), 5.12 (s, 2H, $CH_2$—O), 4.0 (t, J=6.5 Hz, 2H, O—$CH_2$), 3.81 (s, 3H, methyl ester), 3.78 (s, 3H, OMe), 2.54 (t, J=7.6 Hz, 2H, benzylic), 1.88 (m, 2H, $CH_2$), 1.51 (s, 9H, 'butyl), 1.46 (m, 10H, aliphatic).

10(l) 3-[1-Oxa-2-[2-(E-2-carboxymethylethenyl)-3-(8 -(4-methoxy-phenyl)octyloxy)-6-pyridyl]ethyl]aniline.

2-(E-2-Carboxymethylethenyl)-3-[8-(4-methoxyphenyl)-octyloxy]-6-[(3-amino)phenoxymethyl]pyridine 'butylcarbamate (348 mg, 0.562 mmol) was dissolved in dry $CH_2Cl_2$ (3.0 mL) under an argon atmosphere and cooled to 0∞C. Anisole (0.09 mL, 0.83 mmol) was added followed by trifluoroacetic acid (0.6 mL). The reaction was stirred for 1 hour at 0° C. and then for 3 hours at room temperature. The reaction was quenched with aqueous $NaHCO_3$. The product was extracted into $CH_2Cl_2$ and the organic extracts were washed with brine and dried ($MgSO_4$). Purification by flash column chromatography (silica, EtOAc:hexane:$CH_2Cl_2$, 20:50:30) gave a pale yellow oil: $^1$H NMR (250 MHz, $CDCl_3$) δ8.09 (d, J=15.7 Hz, 1H, olefin), 7.44 (d, J=8.6 Hz, 1H, 5-pyridyl), 7.17 (d, J=8.6 Hz, 1H, 4-pyridyl), 7.08 (m, 3H, aryl), 7.05 (d, J=15.7 Hz, 1H, olefin), 6.88 (d, J=8.6 Hz, 2H, aryl), 6.42 (m, 1H, aryl), 6.31 (m, 1H, aryl), 6.29 (m, 1H, aryl), 5.10 (s, 2H, $CH_2$—O), 4.02 (t, J=6.5 Hz, 2H, O—$CH_2$), 3.81 (s, 3H, methyl ester), 3.78 (s, 3H, OMe), 3.70 (broad singlet, 2H, $NH_2$), 2.54 (t, J=7.6 Hz, 2H, benzylic), 1.88 (m, 2H, $CH_2$), 1.62 (m, 2H, $CH_2$), 1.40 (m, 8H, aliphatic); Analysis calcd for $C_{31}H_{38}N_2O_5$·½ $H_2O$: C, 70.56; H, 7.45; N, 5.31; found: C, 70.74; H, 7.36; N, 5.06; MS (CI): 519.3 (M+H).

10(m) 3-[1-Oxa-2-[2-(E-2-carboxyethenyl)-3-(8-(4-methoxyphenyl)-octyloxy)-6-pyridyl]ethyl]aniline, lithium salt.

3-[1-Oxa-2-[2-(E-2-carboxymethylethenyl)-3-(8-(4-methoxyphenyl)octyloxy)-6-pyridyl]ethyl]aniline (30 mg, 0.0578 mmol) was dissolved in THF (0.36 mL) and MeOH (0.24 mL) and treated with 1.0M LiOH (0.12 mL, 0.12 mmol). The reaction was stirred under an argon atmosphere for 6 hours. The solvent was evaporated and the product purified by Reversed Phased MPLC (RP-18 silica, $H_2O$MeOH gradient). Lyophilization yielded a colorless amorphous solid: $^1$H NMR (250 MHz, $d^4$-MeOH) δ7.80 (d, J=15.7 Hz, 1H, olefin), 7.38 (s, 2H, 4,5-pyridyl), 7.0 (d, J=15.7 Hz, 1H, olefin), 7.05 (d, J=8.6Hz, 2H, phenyl), 6.97 (t, J=8.0 Hz, 1H, 5'-phenyl), 6.78 (d, J=8.6 Hz, 2H, phenyl), 6.39 (m, 1H, 2'-phenyl), 6.35 (m, 2H, 4', 6'-phenyl), 5.04 (s, 2H, $CH_2$—O), 4.04 (t, J=6.5 Hz, 2H, O—$CH_2$), 3.74 (s, 3H, OMe), 2.52 (t, J=7.6 Hz, 2H, benzylic), 1.85 (m, 2H, $CH_2$), 1.57 (m, 4H, aliphatic), 1.36 (m, 6H, aliphatic); Analysis calcd for $C_{30}H_{35}N_2O_5Li$·¾$H_2O$: C, 65.38;H, 7.22;N, 5.08; found: C, 65.39;H, 7.24;N, 5.23; MS (FAB): 511 (M+H), 517 (M+Li).

EXAMPLE 11

5-Carboxy-3-[1-oxa-2-[2-(E-2-carboxyethenyl)-3-(8-(4-methoxyphenyl)octyloxy)-6-pyridyl]ethyl]aniline, dilithium salt 11(a) 3-Amino-5-carboxymethylphenol HCl gas was bubbled through a solution of 3-amino-5-hydroxybenzoic acid hydrochloride (1.9 g, 10 mmol; Lancaster Synthesis) in MeOH (50 mL) at 0° C. for 30 minutes. The reaction was stoppered and allowed to sit for 5 hours. The solvent was removed in vacuo and the residue was dissolved in $H_2O$. The aqueous solution was neutralized with 5% $Na_2CO_3$ and the product was extracted into EtOAc. The organic solution was then dried ($MgSO_4$) and evaporated producing 1.5 g (89%) of ester as an off-white solid that was used without additional purification: $^1$H NMR (250 MHz, $CDCl_3$) δ6.85 (dd, J=1.9 Hz, 1H, aryl), 6.80 (dd, J=1.9 Hz, 1H, aryl), 6.30 (dd, J=1.9 Hz, 1H, aryl), 3.80 (s, 3H, methyl ester).

11(b) 3-Amino-5-carboxymethylphenol 'butylcarbamate

A solution of 3-amino-5-carboxymethylphenol (1.5 g, 8.0 mmol) in DMF (8 mL) under an argon atmosphere was treated with di-'butyldicarbonate (2.1 g, 10 mmol). The reaction was stirred at room temperature for 16 hours. The reaction was diluted with EtOAc and washed with $H_2O$ and brine and dried ($MgSO_4$). Recrystallization from $Et_2O$—hexane gave a tan solid: $^1$H NMR (250 MHz, $CDCl_3$) δ7.35 (dd, J=1.9 Hz, 1H, aryl), 7.15 (dd, J=1.9 Hz, 1H, aryl), 6.65 (dd, J=1.9 Hz, 1H, aryl), 6.45 (s, 1H, NH), 3.80 (s, 3H, methyl ester), 1.4 (s, 9H, 'butyl).

11(c) 2-(E-2-Carboxymethylethenyl)-3-[8-(4-methoxyphenyl)-octyloxy]-6-[(3-amino-5-carboxymethyl)phenoxymethyl]pyridine 'butylcarbamate.

To a cooled (0° C.) solution of $SOCl_2$ (0.34 mL, 4.6 mmol) in dry toluene (1.5 mL) under an argon atmosphere was added a solution of 2-(E-2-carboxymethylethenyl)-3-[8-(4-methoxyphenyl)octyloxy]-6-hydroxymethylpyridine (197 mg, 0.46 mmol) in toluene (3 mL). After 5 minutes the cooling bath was removed and the reaction was stirred for 2 hours at room temperature. The toluene and excess $SOCl_2$ were evaporated. To this was added dry DMF (1.0 mL), 3-amino-5-carboxymethylphenol 'butylcarbamate (150 mg, 0.5 mmol), and anhydrous $Cs_2CO_3$ (1.0 g, 3.0 mmol). The reaction was heated at 90° C. under an atmosphere of argon for 2 hours. Upon cooling to room temperature the reaction was diluted with EtOAc and washed with $H_2O$, 10% NaOH, $H_2O$, and brine and dried ($MgSO_4$).

Purification by flash column chromatography (silica, 20% EtOAc in hexane) yielded a colorless oil: $^1$H NMR (250

MHz, CDCl$_3$) δ8.09 (d, J=15.7 Hz, 1H, olefin), 7.55 (dd, J=1.9 Hz, 1H, aryl), 7.9 (dd, J=1.9 Hz, 1H, aryl), 7.46 (d, J=8.6 Hz, 1H, 5-pyridyl) 7.38(dd, J=1.9 Hz, 1H, aryl), 7.22 (d, J=8.6 Hz, 1H, 4-pyridyl), 7.12 (d, J= 8.6 Hz, 2H, phenyl), 7.07 (d, J=15.7 Hz, 1H, olefin), 6.82 (d, J=8.6 Hz, 2H, phenyl), 6.58 (s, 1H, NH), 5.16 (s, 2H, CH$_2$—O), 4.04 (t, J=6.5 Hz, 2H, O—CH$_2$), 3.92 (s, 3H, methyl ester), 3.82 (s, 3H, methyl ester), 3.78 (s, 3H, OMe), 2.58 (t, J=7.6 Hz, 2H, benzylic), 1.88 (m, 2H, CH$_2$), 1.55 (s, 9H, $^t$butyl), 1.46 (m, 10H, aliphatic); MS (CI): 677 (M+H).

11(d) 5-Carboxymethyl-3-[1-oxa-2-[2-(E-2-carboxymethylethenyl)-3-(8-(4-methoxyphenyl)octyloxy)-6-pyridyl]ethyl]aniline 2-(E-2-Carboxymethylethenyl)-3-[8-(4-methoxyphenyl) octyloxy]-6-[(3-amino-5-carboxymethyl)phenoxymethyl] pyridine $^t$butylcarbamate (200 mg, 0.29 mmol) was dissolved in dry CH$_2$Cl$_2$ (3.0 mL) under an argon atmosphere and cooled to 0° C. Anisole (0.05 mL, 0.46 mmol) was added followed by trifluoroacetic acid (0.3 mL). The reaction was stirred for 30 minutes at 0° C. and then for 3.5 hours at room temperature. The reaction was quenched with aqueous NaHCO$_3$. The product was extracted into CH$_2$Cl$_2$ and the organic extracts were washed with brine and dried (MgSO$_4$). Purification by flash column chromatography (silica, 25% EtOAc in hexane) gave a colorless oil: $^1$H NMR (250 MHz, CDCl$_3$) δ8.09 (d, J=15.7 Hz, 1H, olefin), 7.44 (d, J=8.6 Hz, 1H, 5-pyridyl), 7.17 (d, J=8.6 Hz, 1H, 4-pyridyl), 7.08 (m, 3H, aryl), 7.05 (d, J=15.7 Hz, 1H, olefin), 6.96 (dd, J=1.9 Hz, 1H, aryl), 6.88 (d, J=8.6 Hz, 2H, phenyl), 6.49 (dd, J=1.9 Hz, 1H, aryl), 5.12 (s, 2H, CH$_2$—O), 4.04 (t, J=6.5 Hz, 2H, O—CH$_2$), 3.92 (s, 3H, methyl ester), 3.82 (s, 3H, methyl ester), 3.78 (s, 3H, OMe), 2.54 (t, J=7.6 Hz, 2H, benzylic), 1.88 (m, 2H, CH$_2$), 1.62 (m, 2H, CH$_2$), 1.40 (m, 8H, aliphatic); Analysis calcd for C$_{33}$H$_{40}$N$_2$O$_7$. ½H$_2$O: C, 67.67; H, 7.06; N, 4.78; found: C, 67.42; H, 6.96; N, 4.69; MS (CI): 577 (M+H).

11(e) 5-Carboxy-3-[1-oxa-2-[2-(E-2-carboxyethenyl)-3-(8-(4-methoxyphenyl)octyloxy)-6-pyridyl]ethyl]aniline, dilithium salt.

5-Carboxymethyl-3-[1-oxa-2-[2-(E-2-carboxymethylethenyl)-3-(8-(4-methoxyphenyl)octyloxy)-6-pyridyl]ethyl]aniline (120 mg, 0.208 mmol) was dissolved in THF (1.0 mL) and MeOH (0.5 mL) and treated with 1.0M LiOH (0.5 mL, 0.5 mmol). The reaction was stirred under an argon atmosphere for 16 hours. The solvent was evaporated and the product purified by Reversed Phased MPLC (RP-18 silica, H$_2$O-MeOH gradient). Lyophilization yielded a colorless amorphous solid: $^1$H NMR (250 MHz, d$^4$-MeOH) δ7.80 (d, J=15.7 Hz, 1H, olefin), 7.42 (d, J=8.6 Hz, 1H, 5-pyridyl), 7.38 (d, J=8.6 Hz, 1H, 4-pyridyl), 7.06 (d, J=15.7 Hz, 1H, olefin), 7.05 (d, J=8.6 Hz, 2H, phenyl), 6.98 (dd, J=1.9 Hz, 1H, aryl), 6.92 (dd, J=1.9 Hz, 1H, aryl), 6.80 (d, J=8.6 Hz, 2H, phenyl), 6.47 (dd, J=1.9 Hz, 1H, aryl), 5.11 (s, 2H, CH$_2$—O), 4.05 (t, J=6.5 Hz, 2H, O—CH$_2$), 3.74 (s, 3H, OMe), 2.52 (t, J=7.6 Hz, 2H, benzylic), 1.85 (m, 2H, CH$_2$), 1.57 (m, 4H, aliphatic), 1.36 (m, 6H, aliphatic); Analysis calcd for C$_{31}$H$_{34}$N$_2$O$_5$Li$_2$. 2⅛H$_2$O: C, 58.04; H, 6.70; N, 4.36; found: C, 57.87; H, 6.34; N, 4.22; MS (FAB): 561 (M+H).

EXAMPLE 12

3-[1-Thia-2-[2-(E-2-carboxyethenyl)-3-(8-(4-methoxyphenyl)octyloxy)-6-pyridyl]ethyl]aniline, lithium salt 12(a) 3-[1-Thia-2-[2-(E-2-carboxymethylethenyl)-3-(8-(4-methoxy-phenyl)octyloxy)-6-pyridyl]ethyl]aniline.

To a cooled (0° C.) solution of SOCl$_2$ (0.26 mL, 3.5 mmol) in dry toluene (1 mL) under an argon atmosphere was added a solution of 2-(E-2-carboxymethylethenyl)-3-[8-(4-methoxyphenyl)octyloxy]-6-hydroxymethylpyridine (150 mg, 0.35 mmol) in toluene (2.5 mL). After 5 minutes the cooling bath was removed and the reaction was stirred for 2 hours at room temperature. The toluene and excess SOCl$_2$ were evaporated. The crude product was dissolved in dry DMF (1 mL) and added to a solution of sodium 3-aminothiophenoxide, prepared from 3-aminothiophenol (0.09 mL, 0.84 mmol; Aldrich) and NaH (34 mg, 0.084 mmol; 60% in mineral oil) in DMF (2 mL), under an argon atmosphere. The reaction was stirred at room temperature for 3 hours. The reaction was diluted with EtOAc and washed with H$_2$O and brine and dried (MgSO$_4$). Purification by flash column chromatography (silica, 30% EtOAc in hexane) gave a colorless solid: $^1$H NMR (250 MHz, CDCl$_3$) δ8.06 (d, J=15.7 Hz, 1H, olefin), 7.27 (d, J=8.6 Hz, 1H, 5-pyridyl), 7.08 (m, 5H, 4-pyridyl, 5'-phenyl, olefin, phenyl), 6.81 (d, J=8.6 Hz, 2H, phenyl), 6.74 (m, 2H, 2',4'-phenyl), 6.46 (ddd, J=8.0, 1.9 Hz, 1H, 6'-phenyl), 4.20 (s, 2H, CH$_2$—S), 3.96 (t, J=6.5 Hz, 2H, O—CH$_2$), 3.81 (s, 3H, methyl ester), 3.78 (s, 3H, OMe), 3.65 (broad singlet, 2H, NH$_2$), 2.55 (t, J=7.6 Hz, 2H, benzylic), 1.83 (m, 2H, CH$_2$), 1.60 (m, 2H, CH$_2$), 1.45 (m, 2H, CH$_2$), 1.35 (m, 6H, aliphatic); Analysis calcd for C$_{31}$H$_{38}$N$_2$O$_4$S . ¼H$_2$O: C, 69.06; H, 7.20; N, 5.20; found: C, 69.02; H, 7.16; N, 5.21; MS (CI): 535 (M+H); mp 57°–60° C.

12(b) 3-[1-Thia-2-[2-(E-2-carboxyethenyl)-3-(8-(4-methoxyphenyl)octyloxy)-6-pyridyl]ethyl]aniline, lithium salt.

3-[1-Thia-2-[2-(E-2-carboxymethylethenyl)-3-(8-(4-methoxyphenyl)octyloxy)-6-pyridyl]ethyl]aniline (75 mg, 0.14 mmol) was dissolved in THF (0.56 mL) and MeOH (0.28 mL) and treated with 1.0M LiOH (0.28 mL, 0.28 mmol). The reaction was stirred under an argon atmosphere for 6 hours. The solvent was evaporated and the product purified by Reversed Phased MPLC (RP-18 silica, H$_2$O-MeOH gradient). Lyophilization yielded a colorless amorphous solid: $^1$H NMR (250 MHz, d$^4$-MeOH) δ7.76 (d, J=15.7 Hz, 1H, olefin), 7.25 (d, J=8.6 Hz, 1H, 5-pyridyl), 7.24 (d, J=8.6 Hz, 1H, 4-pyridyl), 7.09 (d, J=8.6 Hz, 2H, phenyl), 7.04 (d, J=15.7 Hz, 1H, olefin), 6.97 (dd, J=8.0 Hz, 1H, 5'-phenyl), 6.80 (d, J=8.6 Hz, 2H, phenyl), 6.72 (dd, J=1.9 Hz, 1H, 2'-phenyl), 6.67 (ddd, J=8.0, 1.9 Hz, 1H, 4'-phenyl 6.51 (ddd, J=8.0, 1.9 Hz, 1H, 6'-phenyl), 4.16 (s, 2H, CH$_2$—S), 4.00 (t, J=6.5 Hz, 2H, O—CH$_2$), 3.74 (s, 3H, OMe), 2.52 (t, J=7.6 Hz, 2H, benzylic), 1.80 (m, 2H, CH$_2$), 1.49 (m, 4H, aliphatic), 1.33 (m, 6H, aliphatic); Analysis calcd for C$_{30}$H$_{35}$N$_2$O$_4$SLi. ½H$_2$O: C, 63.03; H, 7.05; N, 4.90; found: C, 62.67; H, 6.72; N, 4.72; MS (FAB): 527 (M+H), 521 (M+H; free acid).

Proceeding in a similar manner, but substituting the appropriate intermediates for those indicated here, and using chemistry well known in the art, the following compounds were prepared:

3-[1-thia-2-[2-(E-2-carboxyethenyl)-3-(4-(4-methoxyphenyl)butyloxy)-6-pyridyl ethyl]aniline, lithium salt;

Colorless amorphous solid: $^1$H NMR (360 MHz, d$^6$-DMSO) δ7.43 (d, J=15.7 Hz, 1H, olefin), 7.33 (d, J=8.6 Hz, 1H, pyridyl), 7.23 (d, J=8.6 Hz, 1H, pyridyl), 7.13 (d, J=8.6 Hz, 2H, phenyl), 6.92 (dd, J=7.8 Hz, 1H, 5'-phenyl), 6.86 (d J=15.7 Hz, 1H, olefin), 6.82 (d, J=8.6 Hz, 2H, phenyl), 6.61 (s, 1H, 2'-phenyl), 6.51 (d, J=7.8 Hz, 1H, 4'-phenyl), 6.37 (d, J=7.8 Hz, 1H, 6'-phenyl), 5.10 (broad singlet, 2H, NH$_2$), 4.16 (s, 2H, CH$_2$—S), 4.01 (t, J=6.5 Hz, 2H, O—CH$_2$), 3.72 (s, 3H, OMe), 2.58 (t, J=7.6 Hz, 2H, benzylic), 1.71 (m, 4H, aliphatic); Analysis calcd for C$_{26}$H$_{27}$N$_2$O$_4$SLi . 1¾H$_2$O: C, 62.20; H, 6.12; N, 5.58; found: C, 62.23; H, 5.82; N, 5.44; MS (ES$^+$): 464.3 (M+; free acid); (ES$^-$): 463.0 (M–H; free acid);

3-[1-thia-2-[2-(E-2-carboxyethenyl)-3-(8-(4-trifluoromethylphenyl)octyloxy)-6-pyridyl]ethyl]aniline, lithium salt;

Colorless amorphous solid: $^1$H NMR (250 MHz, d$^4$-MeOH) δ7.78 (d, J=15.7 Hz, 1H, olefin), 7.53 (d, J=8.6 Hz, 2H, phenyl), 7.34 (d, J=8.6 Hz, 2H, phenyl), 7.25 (d, J=8.6 Hz, 1H, pyridyl), 7.24 (d, J=8.6 Hz, 1H, pyridyl), 7.04 (d, J=15.7 Hz, 1H, olefin), 6.97 (dd, J=8.0 Hz, 1H, 5'-phenyl), 6.72 (dd, J=1.9 Hz, 1H, 2'-phenyl), 6.67 (ddd, J=8.0, 1.9 Hz, 1H, 4'-phenyl), 6.51 (ddd, J=8.0, 1.9 Hz, 1H, 6'-phenyl), 4.16 (s, 2H, CH$_2$—S), 4.01 (t, J=6.5 Hz, 2H, O—CH$_2$), 2.68 (t, J=7.6 Hz, 2H, benzylic), 1.85 (m, 2H, CH$_2$), 1.68 (m, 2H, CH$_2$), 1.50 (m, 2H, CH$_2$), 1.37 (m, 6H, aliphatic); Analysis calcd for C$_{30}$H$_{32}$F$_3$N$_2$O$_3$SLi · 1½H$_2$O: C, 60.91; H, 5.96; N, 4.74; found: C, 60.53; H, 5.56; N, 4.51; MS (ES+): 559.0 (M+H; free acid), (ES–): 557.0 (M–H; free acid); and 3-[1-thia-2-[2-(E-2-carboxyethenyl)-3-(8-phenyl)octyloxy-6-pyridyl]ethyl]aniline, lithium salt Colorless amorphous solid: $^1$H NMR (250 MHz, d$^4$-MeOH) δ7.72 (d, J=15.7 Hz, 1H, olefin), 7.20 (m, 7H, pyridyl, phenyl), 7.04 (d, J=15.7 Hz, 1H, olefin), 6.97 (dd, J=8.0 Hz, 1H, 5'-phenyl), 6.72 (dd, J=1.9 Hz, 1H, 2'-phenyl), 6.67 (ddd, J=8.0, 1.9 Hz, 1H, 4'-phenyl), 6.51 (ddd, J=8.0, 1.9 Hz, 1H, 6'-phenyl), 4.16 (s, 2H, CH$_2$—S), 4.02 (t, J=6.5 Hz, 2H, O—CH$_2$), 2.52 (t, J=7.6 Hz, 2H, benzylic), 1.83 (m, 2H, CH$_2$), 1.59 (m, 2H, CH$_2$), 1.50 (m, 2H, CH$_2$), 1.37 (m, 6H, aliphatic); MS (ES+): 491.0 (M+H; free acid), (ES–): 489.0 (M–H; free acid).

EXAMPLE 13

3-[1-Oxythia-2-[2-(E-2-carboxyethenyl)-3-(8-(4-methoxyphenyl)octyloxy)-6-pyridyl]ethyl]aniline, lithium salt 13(a) 3-[1-Oxythia-2-[2-(E-2-carboxymethylethenyl)-3-(8-(4-methoxyphenyl)octyloxy)-6-pyridyl]ethyl]aniline.

To a cooled (−15° C.) solution of 3-[1-thia-2-[2-(E-2-carboxymethylethenyl)-3-(8-(4-methoxyphenyl)octyloxy)-6-pyridyl]ethyl]aniline (150 mg, 0.28 mmol) in CH$_2$Cl$_2$ (4 mL) under an argon atmosphere was added 85% mCPBA (63 mg, 0.31 mmol) in two portions over 15 minutes. The reaction was maintained at −15° C. for a total of 40 minutes. The reaction was quenched with aq NaHCO$_3$ solution and the product extracted into EtOAc. The organic extract was washed with H$_2$O and brine and dried (MgSO$_4$). The product was recrystallized from EtOAc—hexane to give a colorless solid: $^1$H NMR (250 MHz, CDCl$_3$) δ8.03 (d, J=15.7 Hz, 1H, olefin), 7.22 (dd, J=8.0 Hz, 1H, 5'-phenyl), 7.15 (m, 2H, 4,5-pyridyl), 7.11 (d, J=8.6 Hz, 2H, phenyl), 6.92 (m, 1H, 2'-phenyl), 6.85 (d, J=15.7 Hz, 1H, olefin), 6.80 (m, 3H, phenyl, 4'-phenyl), 6.73 (ddd, J=8.0, 1.9 Hz, 1H, 6'-phenyl), 4.12 (s, 2H, CH$_2$—S), 4.00 (t, J=6.5 Hz, 2H, O—CH$_2$), 3.99 (broad singlet, 2H, NH$_2$), 3.82 (s, 3H, methyl ester), 3.79 (s, 3H, OMe), 2.56 (t, J=7.6 Hz, 2H, benzylic), 1.85 (m, 2H, CH$_2$), 1.60 (m, 2H, CH$_2$), 1.48 (m, 2H, CH$_2$), 1.36 (m, 6H, aliphatic); Analysis calcd for C$_{31}$H$_{38}$N$_2$O$_5$S: C, 67.61; H, 6.95; N, 5.09; found: C, 67.73; H, 7.17; N, 4.82; MS (CI): 551 (M+H); mp 109°–111° C.

13(b) 3-[1-Oxythia-2-[2-(E-2-carboxyethenyl)-3-(8-(4-methoxy-phenyl)octyloxy)-6-pyridyl]ethyl]aniline, lithium salt.

3-[1-Oxythia-2-[2-(E-2-carboxymethylethenyl)-3-(8(4-methoxyphenyl)octyloxy)-6-pyridyl]ethyl]aniline (109 mg, 0.198 mmol) was dissolved in THF (0.80 mL) and MeOH (0.40 mL) and treated with 1.0M LiOH (0.40 mL, 0.40 mmol). The reaction was stirred under an argon atmosphere for 6 hours. The solvent was evaporated and the product purified by Reversed Phased MPLC (RP-18 silica, H$_2$O-MeOH gradient). Lyophilization yielded a colorless amorphous solid: $^1$H NMR (250 MHz, d$^4$-MeOH) δ7.75 (d, J=15.7 Hz, 1H, olefin), 7.28 (d, J=8.6 Hz, 1H, 5-pyridyl), 7.15 (dd, J=8.0 Hz, 1H, 5'-phenyl), 7.03 (m, 4H, 4-pyridyl, olefin, phenyl) 6.86 (dd, J=1.9 Hz, 1H, 2'-phenyl), 6.75 (m, 4H, 4',6'-phenyl, phenyl), 4.20 (q, J=13 Hz, 2H, CH$_2$—S), 4.02 (t, J=6.5 Hz, 2H, O—CH$_2$), 3.72 (s, 3H, OMe), 2.52 (t, J=7.6 Hz, 2H, benzylic), 1.85 (m, 2H, CH$_2$), 1.53 (m, 4H, aliphatic), 1.37 (m, 6H, aliphatic); Analysis calcd for C$_{30}$H$_{35}$N$_2$O$_5$SLi · 2H$_2$O: C, 62.27; H, 6.79; N, 4.84: found: C, 62.13; H, 6.89; N, 5.01; MS (FAB): 543 (M+H), 537 (M+H; free acid).

Proceeding in a similar manner, them was there 3-[1-oxythia-2-[2-(E-2-carboxyethenyl)-3-(4-(4-methoxyphenyl))-6-pyridyl]ethyl]aniline, lithium salt;

Colorless amorphous solid: $^1$H NMR (250 MHz, d$^4$-MeOH) δ7.75 (d, J=15.7 Hz, 1H, olefin), 7.28 (d, J=8.6 Hz, 1H, pyridyl), 7.20 (d, J=8.6 Hz, 1H, pyridyl), 7.12 (d, J=8.6 Hz, 2H, phenyl), 7.06 (s, 1H, 2'-phenyl), 7.02 (d, J=7.8 Hz, 1H, 4'-phenyl), 6.81 (m, 5H, 5',6'-phenyl, olefin, phenyl), 4.20 (q, J=13 Hz, 2H, CH$_2$—S(O)), 4.02 (t, J=6.5 Hz, 2H, O—CH$_2$), 3.72 (s, 3H, OMe), 2.62 (t, J=7.6 Hz, 2H, benzylic), 1.80 (m, 4H, aliphatic); Analysis calcd for C$_{26}$H$_{27}$N$_2$O$_5$SLi · 2⅝H$_2$O: C, 58.50; H, 6.09; N, 5.25; found: C, 58.18; H, 5.67; N, 5.12; MS (ES$^+$): 481.2 (M+H; free acid), (ES–): 479.0 (M–H; free acid).

3-[1-oxythia-2-[2-(E-2-carboxyethenyl)-3-(8-(4-trifluoromethylphenyl)octyloxy)-6-pyridyl]ethyl]aniline, lithium salt;

Colorless amorphous solid: $^1$H NMR (250 MHz, d$^4$-MeOH) δ7.75 (d, J=15.7 Hz, 1H, olefin), 7.53 (d, J=8.6 Hz, 2H, phenyl), 7.34 (d, J=8.6 Hz, 2H, phenyl), 7.24 (d, J=8.6 Hz, 1H, pyridyl), 7.18 (d, J=8.6 Hz, 1H, pyridyl), 7.04 (d, J=8.0 Hz, 1H, 4'-phenyl), 7.02 (d, J=15.7 Hz, 1H, olefin), 6.89 (s, 1H, 2'-phenyl), 6.78 (m, 2H, 5',6'-phenyl), 4.20 (q, J=13 Hz, 2H, CH$_2$—S(O)), 4.02 (t, J=6.5 Hz, 2H, O—CH$_2$), 2.52 (t, J=7.6 Hz, 2H, benzylic), 1.88 (m, 2H, CH$_2$), 1.69 (m, 2H, CH$_2$), 1.50 (m, 2H, CH$_2$), 1.39 (m, 6H, aliphatic); Analysis calcd for C$_{30}$H$_{32}$F$_3$N$_2$O$_4$SLi · 1¾H$_2$O: C, 58.87; H, 5.85; N, 4.58; found: C, 58.92; H, 5.55; N, 4.48; MS (ES +): 575.2 (M+H; free acid);

3-[1-oxythia-2-[2-(E-2-carboxyethenyl)-3-(8-phenyl)octyloxy-6-pyridyl]ethyl]aniline, lithium salt;

Colorless amorphous solid: $^1$H NMR (250 MHz, d$^4$-MeOH) δ7.75 (d, J=15.7 Hz, 1H, olefin), 7.20 (m, 7H, pyridyl, phenyl), 7.04 (d, J=8.0 Hz, 1H, 4'-phenyl 7.02 (d, J=15.7 Hz, 1H, olefin), 6.89 (s, 1H, 2'-phenyl), 6.78 (m, 2H, 5', 6'-phenyl), 4.20 (q, J=13 Hz, 2H, CH$_2$—S(O)), 4.02 (t, J=6.5 Hz, 2H, O—CH$_2$), 2.52 (t, J=7.6 Hz, 2H, benzylic), 1.88 (m, 2H, CH$_2$), 1.69 (m, 2H, CH$_2$), 1.50 (m, 2H, CH$_2$), 1.39 (m, 6H, aliphatic); Analysis calcd for C$_{29}$H$_{33}$N$_2$O$_4$SLi · 1 H$_2$O: C, 65.65; H, 6.65; N, 5.28; found: C, 65.62; H, 6.39; N, 4.90; MS (ES+): 507.0 (M+H; free acid), (ES–): 505.0 (M–H; free acid);

3-[1-oxythia-2-[2-(E-2-carboxyethenyl)-3-(8-(4-fluorophenyl)octyloxy)-6-pyridyl]ethyl]aniline, lithium salt;

Colorless amorphous solid: $^1$H NMR (250 MHz, d$^4$-MeOH) δ7.75 (d, J=15.7 Hz, 1H, olefin), 7.30–6.90 (multiplet, 8H, pyridyl, phenyl, olefin, 4'-phenyl), 6.89 (s, 1H, 2'-phenyl), 6.78 (m, 2H, 5',6'-phenyl), 4.20 (q, J=13 Hz, 2H, CH$_2$—S(O)), 4.02 (t, J=6.5 Hz, 2H, O—CH$_2$), 2.52 (t, J=7.6 Hz, 2H, benzylic), 1.88 (m, 2H, CH$_2$), 1.59 (m, 2H, CH$_2$), 1.50 (m, 2H, CH$_2$), 1.39 (m, 6H, aliphatic): MS (ES+): 525.2 (M+H; free acid), (ES–): 523.0 (M–H; free acid).

EXAMPLE 14

3-[Dioxythia-2-[2-(E-2-carboxyethenyl)-3-(8-(4-methoxyphenyl)octyloxy)-6-pyridyl]ethyl]aniline, lithium salt

14(a) 3-[1-Dioxythia-2-[2-(E-2-carboxymethylethenyl)-3-(8-(4-methoxyphenyl)octyloxy-6-pyridyl]ethyl]aniline To a cooled (0° C.) solution of 3-[1-thia-2-[2-(E-2-carboxymethylethenyl)-3-(8-(4-methoxyphenyl)octyloxy)-6-pyridyl]ethyl]aniline (75 mg, 0.14 mmol) in $CH_2Cl_2$ (3 mL) under an argon atmosphere was added 85% mCPBA (63 mg, 0.308 mmol). After 1 hour the reaction was quenched with aq $NaHCO_3$ solution and the product extracted into EtOAc. The organic extracts were washed with $H_2O$ and brine and dried ($MgSO_4$). Purification by flash column chromatography (silica, 50% EtOAc in hexane) gave a colorless solid: $^1H$ NMR (250 MHz, $CDCl_3$) $\delta$7.90 (d, J=15.7 Hz, 1H, olefin), 7.39 (d, J=8.6 Hz, 1H, 5-pyridyl), 7.21 (t, J=8.0 Hz, 1H, 5'-phenyl), 7.19 (d, J=8.6 Hz, 1H, 4-pyridyl), 7.11 (d, J=8.6 Hz, 2H, phenyl), 7.03 (m, 2H, 2',4'-phenyl), 6.86 (m, 1H, 6'-phenyl), 6.81 (d, J=8.6 Hz, 2H, phenyl), 6.54 (d, J=15.7 Hz, 1H, olefin), 4.46 (s, 2H, $CH_2$—S), 3.99 (t, J=6.5 Hz, 2H, O—$CH_2$), 3.86 (broad singlet, 2H, $NH_2$), 3.79 (s, 3H, methyl ester), 3.78 (s, 3H, OMe), 2.55 (t, J=7.6 Hz, 2H, benzylic), 1.82 (m, 2H, $CH_2$), 1.60 (m, 2H, $CH_2$), 1.45 (m, 2H, $CH_2$), 1.35 (m, 6H, aliphatic); Analysis calcd for $C_{31}H_{38}N_2O_6S$ . ⅓ mol $C_6H_{14}$: C, 66.57; H, 7.22; N, 4.70; found: C, 66.45; H, 7.24; N, 4.89; MS (CI): 567 (M+H); mp 92°–95° C.

14(b) 3-[1-Dioxythia-2-[2-(E-2-carboxyethenyl)-3-(8-(4-methoxyphenyl)octyloxy) -6-pyridyl]ethyl]aniline, lithium salt.

3-[1-Dioxythia-2-[2-(E-2-carboxymethylethenyl)-3-(8-(4-methoxyphenyl)octyloxy)-6-pyridyl]ethyl]aniline (51 mg, 0.09 mmol) was dissolved in THF (0.30 mL) and MeOH (0.18 mL) and treated with 1.0M LiOH (0.18 mL, 0.18 mmol). The reaction was stirred under an argon atmosphere for 6 hours. The solvent was evaporated and the product purified by Reversed Phased MPLC (RP-18 silica, $H_2O$—MeOH gradient). Lyophilization yielded a colorless amorphous solid: $^1H$ NMR (250 MHz, $d^4$-MeOH) $\delta$7.65 (d, J=15.7 Hz, 1H, olefin), 7.26 (d, J=8.6 Hz, 1H, 5-pyridyl), 7.24 (d, J=8.6 Hz, 1H, 4-pyridyl), 7.17 (dd, J=8.0 Hz, 1H, 5'-phenyl), 7.06 (d, J=8.6 Hz, 2H, phenyl), 6.97 (dd, J=1.9 Hz, 1H, 2'-phenyl), 6.85 (m, 2H, 4', 6'-phenyl), 6.78 (d, J=8.6 Hz, 2H, phenyl), 6.75 (d, J=15.7 Hz, 1H, olefin), 4.55 (s, 2H, $CH_2$—S), 4.04 (t, J=6.5 Hz, 2H, O—$CH_2$), 3.74 (s, 3H, OMe), 2.52 (t, J=7.6 Hz, 2H, benzylic), 1.86 (m, 2H, $CH_2$), 1.55 (m, 4H, aliphatic), 1.37 (m, 6H, aliphatic); MS (FAB): 559 (M+H), 553 (M+H; free acid).

EXAMPLE 15

3-[1-Thia-2-[2-(E-2-carboxyethenyl)-3-(8-(4-methoxyphenyl)octyloxy)-6-pyridyl]ethyl]-N,N-dimethylaniline, lithium salt

15(a) 3-[1-Thia-2-[2-(E-2-carboxymethylethenyl)-3-(8-(4-methoxyphenyl)octyloxy)-6-pyridyl]ethyl]-N,N-dimethylaniline.

To a solution of 3-[1-thia-2-[2-(E-2-carboxymethylethenyl)-3-(8-(4-methoxyphenyl)octyloxy)-6-pyridyl]ethyl]aniline (75 mg, 0.14 mmol) in acetonitrile (1 mL) was added formaldehyde (0.25 mL, 3.1 mmol; 37% aqueous solution) and $NaCNBH_3$ (50 mg, 0.80 mmol). The reaction was stirred at room temperature for 15 minutes. The reaction solution was made neutral by the addition of glacial acetic acid and stirred for an additional 2 hours. The reaction was diluted with $H_2O$ and the product extracted into EtOAc. The organic layer was washed with $H_2O$ and brine and dried ($MgSO_4$). Purification by flash column chromatography (silica, 20% EtOAc in hexane) gave a pale yellow oil: $^1H$ NMR (250 MHz, $CDCl_3$) $\delta$8.06 (d, J=15.7 Hz, 1H, olefin), 7.35 (d, J=8.6 Hz, 1H, 5-pyridyl), 7.08 (m, 4H, 4-pyridyl, 5'-phenyl, phenyl), 7.04 (d, J=15.7 Hz, 1H, olefin), 6.83 (d, J=8.6 Hz, 2H, phenyl), 6.74 (m, 2H, 2',4'phenyl), 6.52 (dd, J=8.0, 1.9 Hz, 1H, 6'-phenyl), 4.23 (s, 2H, $CH_2$—S), 4.00 (t, J=6.5 Hz, 2H, O—$CH_2$), 3.82 (s, 3H, methyl ester), 3.78 (s, 3H, OMe), 2.89 (s, 6H., $Me_2$), 2.55 (t, J=7.6 Hz, 2H, benzylic), 1.83 (m, 2H, $CH_2$), 1.60 (m, 2H, $CH_2$), 1.45 (m, 2H, $CH_2$), 1.35 (m, 6H, aliphatic); MS (CI): 563 (M+H).

15(b) 3-1-Thia-2-[2-(E-2-carboxyethenyl)-3-(8-(4-methoxyphenyl)octyloxy)-6-pyridyl]ethyl]-N,N-dimethylaniline, lithium salt 3-[1-Thia-2-[2-(E-2-carboxymethylethenyl)-3-(8-(4-methoxyphenyl)octyloxy)-6-pyridyl]ethyl]-N,N-dimethylaniline (100 mg, 0.178 mmol) was dissolved in THF (0.72 mL) and MeOH (0.36 mL) and treated with 1.0M LiOH (0.36 mL, 0.36 mmol). The reaction was stirred under an argon atmosphere for 6 hours. The solvent was evaporated and the product purified by Reversed Phased MPLC (RP-18 silica, $H_2O$—MeOH gradient). Lyophilization yielded a colorless amorphous solid: $^1H$ NMR (250 MHz, $d^4$-MeOH) $\delta$7.78 (d, J=15.7 Hz, 1H, olefin), 7.25 (s, 2H, 4,5-pyridyl), 7.07 (m, 4H, phenyl, olefin, 5'-phenyl), 6.80 (d, J=8.6 Hz, 2H, phenyl), 6.72 (dd, J=1.9 Hz, 1H, 2'-phenyl), 6.67-phenyl), 4.20 (s, (ddd, J=8.0, 1.9 Hz, 1H, 4'-phenyl), 6.55 (ddd, J=8.0, 1.9 Hz, 1H, 6'-phenyl), 4.20 (s, 2H, $CH_2$—S), 4.00 (t, J=6.5 Hz, 2H, O—$CH_2$), 3.76 (s, 3H, OMe), 2.85 (s, 6H, $Me_2$), 2.52 (t, J=7.6 Hz, 2H, benzylic), 1.85 (m, 2H, $CH_2$), 1.55 (m, 4H, aliphatic), 1.33 (m, 6H, aliphatic); Analysis calcd for $C_{32}H_{39}N_2O_4SLi$ . 5/4$H_2O$: C, 66.59: H. 7.25: N. 4.85; found: C, 66.50; H, 7.01; N, 4.75; MS (FAB): 555.2 (M+H).

EXAMPLE 16

3-[1-Oxythia-2-[2-(E-2-carboxyethenyl)-3-(8-(4-methoxyphenyl)octyloxy)-6-pyridyl]ethyl]-N,N-dimethylaniline, lithium salt

16(a) 3-[1-Oxythia-2-[2-(E-2-carboxymethylethenyl)-3-(8-(4-methoxyphenyl)octyloxy)-6-pyridyl]ethyl]-N,N-dimethylaniline Prepared from 3-[1-thia-2-[2-(E-2-carboxymethylethenyl)-3-(8-(4-methoxyphenyl)octyloxy)-6-pyridyl]ethyl]-N,N-dimethylaniline according to the procedure described for the preparation of 3-[1-oxythia-2-[2-(E-2-carboxymethylethenyl)-3-(8-(4-methoxyphenyl)octyloxy)-6-pyridyl]ethyl]aniline: $^1H$ NMR (250 MHz, $CDCl_3$) $\delta$8.01 (d, J=15.7 Hz, 1H, olefin), 7.22 (dd, J=8.0 Hz, 1H, 5'-phenyl), 7.17 (d, J=8.6 Hz 1H, 5-pyridyl), 7.13 (d, J=8.6 Hz, 1H, 4-pyridyl), 6.80 (m, 6H, phenyl, 2',4',6'-phenyl, olefin), 4.12 (s, 2H, $CH_2$—S), 4.00 (t, J=6.5 Hz, 2H, O—$CH_2$), 3.82 (s, 3H, methyl ester), 3.79 (s, 3H, OMe), 2.95 (s, 6H, $Me_2$), 2.55 (t, J=7.6 Hz, 2H, benzylic), 1.85 (m, 2H, $CH_2$), 1.60 (m, 2H, $CH_2$), 1.48 (m, 2H, $CH_2$), 1.36 (m, 6H, aliphatic); MS (CI): 579.2 (M+H).

16(b) 3-[1-Oxythia-2-[2-(E-2-carboxyethenyl)-3-(8-(4-methoxyphenyl)octyloxy)-6-pyridyl]ethyl]-N,N-dimethylaniline, lithium salt Prepared from 3-[1-oxythia-2-[2-(E-2-carboxymethylethenyl)-3-(8-(4-methoxyphenyl)octyloxy)-6-pyridyl]ethyl]-N,N-dimethylaniline according to the procedure described for the preparation of 3-[1-oxythia-2-[2-(E-2- carboxyethenyl)-3-(8-(4-methoxyphenyl)octyloxy)-6-pyridyl]ethyl]aniline, lithium salt. Colorless amorphous solid: $^1$H NMR (250 MHz, d$^4$-MeOH) δ7.75 (d, J=15.7 Hz, 1H, olefin), 7.31 (dd, J=8.0 Hz, 1H, 5'-phenyl), 7.24 (d, J=8.6 Hz, 1H, 5-pyridyl), 7.03 (m, 3H, 4-pyridyl, phenyl), 6.95 (d, J=15.7 Hz, 1H, olefin), 6.80 (m, 4H, aryl), 6.70 (m, 1H, aryl), 4.21 (q, J=13 Hz, 2H, CH$_2$—S), 4.02 (t, J=6.5 Hz, 2H, O—CH$_2$), 3.74 (s, 3H, OMe), 2.84 (s, 6H, Me$_2$), 2.56 (t, J=7.6 Hz, 2H, benzylic), 1.85 (m, 2H, CH$_2$), 1.53 (m, 4H, aliphatic), 1.37 (m, 6H, aliphatic); MS (FAB): 571.3 (M+H).

EXAMPLE 17

Preparation of 3-[N-[2-[2-(E-2-Carboxyethenyl)-3-(8-(4-methoxyphenyl)octyloxy)-6-pyridyl]methyl]] aminobenzoic acid, dilithium salt The captioned compound was prepared according to the method set out in Scheme 5 above by reacting the appropriate t-BOC-protected aminobenzoic acid with 2-(E-2-carboxymethylethenyl)-3-dodecyloxy-6-(chloromethyl)-pyridine hydrochloride or a similar intermediate, the captioned compound was prepared.

In a similar manner 3-[N-[2-[2-(E-2-carboxyethenyl)-3-(8-(4-methoxyphenyl)octyloxy)-6-pyridyl]-methyl]] aminobenzoic acid, N-oxide, dilithium salt and 3-[N-[2-[2-(E-2-carboxyethenyl)-3-(8-(4-methoxyphenyl)-octyloxy)-6-pyridyl]methyl]-N-methyl]aminobenzoic acid, dilithium salt were made.

EXAMPLE 18

4-[2-Thia-3-[2-(E-2-carboxyethenyl)-3-[8-(4-methoxyphenyl)octyloxy]-6-pyridyl]propyl]benzoic acid, dilithium salt 18(a). 3-Hydroxy-6-methyl-2-pyridine carboxaldehyde 2,6-Lutidine-a$^2$,3-diol (15 g, 107.8 mmol; Aldrich) was suspended in dry CH$_2$Cl$_2$ (200 mL) and treated with MnO$_2$ (47 g, 539 mmol). The reaction was stirred at room temperature for 6 hours. The reaction mixture was filtered through a pad of Celite and the solvent was evaporated. The crude aldehyde was obtained as a tan solid and was used directly for the next step: $^1$H NMR (250 MHz, CDCl$_3$) δ10.65 (s, 1H, OH), 10.30 (s, 1H, aldehyde), 7.30 (m, 2H, 4,5-pyridyl), 2.55 (s, 3H, methyl).

18(b). 3-[8-(4-Methoxyphenyl)octyloxy]-6-methyl-2-pyridine carboxaldehyde

To a solution of 1-iodo-8-(4-methoxyphenyl)octane (16.3 g, 47.1 mmol) in dry DMF (45 mL) under an argon atmosphere was added 3-hydroxy-6-methyl-2-pyridine carboxaldehyde (7.7 g, 56.2 mmol) and anhydrous K$_2$CO$_3$ (32 g, 235 mmol). The reaction was vigorously stirred at 90° C. for 1.5 hours. Upon cooling to room temperature the reaction was diluted with EtOAc and washed with H$_2$O, aq NH$_4$Cl, and brine and dried (MgSO$_4$). Evaporation provided crude aldehyde as a dark oil that was used without further purification.

18(c). 2-(E-2-Carboxymethylethenyl)-3-[8-(4-methoxyphenyl)-octyloxy]-6-methylpyridine 3-[8-(4-Methoxyphenyl)octyloxy]-6-methyl-2-pyridine carboxaldehyde obtained above was dissolved in dry toluene (100 mL) under an argon atmosphere and treated with methyl (triphenylphosphoranylidene)acetate (16 g, 48 mmol). The reaction was heated for 1 hour at 50° C. Upon cooling to room temperature the reaction was diluted with EtOAc and washed with H$_2$O and brine and dried (MgSO$_4$). Purification by flash column chromatography (silica, 20% EtOAc in hexane) gave the product as a pale yellow oil: $^1$H NMR (250 MHz, CDCl$_3$) δ8.07 (d, J=15.7 Hz, 1H, olefin), 7.10 (m, 4H, phenyl, 4,5-pyridyl), 7.07 (d, J=15.7 Hz, 1H, olefin), 6.81 (d, J=8.6 Hz, 2H, phenyl), 3.97 (t, J=6.5 Hz, 2H, O—CH$_2$), 3.79 (s, 3H, OCH$_3$), 3.78 (s, 3H, methyl ester), 2.54 (t, J=7.6 Hz, 2H, benzylic), 2.48 (s, 3H, methyl), 1.85 (m, 2H, CH$_2$), 1.60 (m, 2H, CH$_2$), 1.37 (m, 8H, aliphatic); MS (CI): 412.3 (M+H).

18(d). 2-(E-2-Carboxymethylethenyl)-3-[8-(4-methoxyphenyl)-octyloxy]-6-methylpyridine N-Oxide 2-(E-2-Carboxymethyl-ethenyl)-3-[8-(4-methoxyphenyl) octyloxy]-6-methylpyridine (17.1 g, 41.5 mmol) was dissolved in dry CH$_2$Cl$_2$ (105 mL) and cooled to 0° C.; 50% m-chlorperbenzoic acid (15.8 g, 45.8 mmol) was added in three portions over 10 minutes. The cooling bath was removed and the reaction was stirred for 15 hours at room temperature. The reaction was poured into aqueous NaHCO$_3$ and the product extracted into CH$_2$C$_{12}$. The organic extract was washed with H$_2$O and brine and dried (MgSO$_4$). The crude product was obtained as a yellow solid and was used without further purification.

18(e). 2-(E-2-Carboxymethylethenyl)-3-[8-(4-methoxyphenyl)-octyloxy]-6-hydroxymethylpyridine 2-(E-2-Carboxymethyl-ethenyl)-3-[8-(4-methoxyphenyl) octyloxy]-6-methylpyridine N-oxide obtained above was suspended in dry DMF (130 mL) and cooled to 0° C. under an argon atmosphere. To this was slowly added trifluoroacetic anhydride (56 mL, 400 mmol). The reaction was maintained at 0° C. for 20 minutes followed by 18 hours at room temperature. The reaction solution was slowly added to a solution of saturated aqueous Na$_2$CO$_3$ and stirred for 1 hour. The product was then extracted into EtOAc; the combined organic extracts were washed with H$_2$O and brine and dried (MgSO$_4$). Purification by flash column chromatography (silica, EtOAc:hexane:CH$_2$Cl$_2$,30:20:50) gave a waxy solid: $^1$H NMR (250 MHz, CDCl$_3$) δ8.08 (d, J=15.7 Hz, 1H, olefin), 7.23 (d, J=8.6 Hz, 1H, 5-pyridyl), 7.16 (d, J=8.6 Hz, 1H, 4-pyridyl), 7.09 (d, J=8.6 Hz, 2H, phenyl), 7.03 (d, J=15.7 Hz, 1H, olefin), 6.82 (d, J=8.6 Hz, 2H, phenyl), 4.69 (d, J=4.1 Hz, 2H, CH$_2$—OH), 4.01 (t, J=6.5 Hz, 2H, O—CH$_2$), 3.82 (s, 3H, OCH$_3$), 3.78 (s, 3H, methyl ester), 3.62 (t, J=4.1 Hz, 1H, OH), 2.55 (t, J=7.6 Hz, 2H, benzylic), 1.85 (m, 2H, CH$_2$), 1.58 (m, 2H, CH$_2$), 1.44 (m, 8H, aliphatic); MS (CI): 428.2 (M+H).

18(f) Methyl 4-[2-thia-3-[2-(E-2-carboxy-methylethenyl)-3-[8-(4-methoxyphenyl)octyloxy]-6-pyridyl]propyl]benzoate To a cooled (0° C.) solution of SOCl$_2$ (0.5 mL, 7.0 mmol) in dry toluene (2 mL) under an argon atmosphere was added a solution of 2-(E-2-carboxymethylethenyl)-3-[8-(4-methoxyphenyl)octyloxy]-6-hydroxymethylpyridine (300 mg, 0.70 mmol) in toluene (5 mL). After 5 minutes the cooling bath was removed and the reaction was stirred for 2 hours at room temperature. The toluene and excess SOCl$_2$ were evaporated. To this was added dry DMF (2 mL), methyl 4-mercaptomethylbenzoate (180 mg, 0.7 mmol) [prepared from 4-mercaptomethylbenzoic acid (Bader) and methanolic HCl], and anhydrous Cs$_2$CO$_3$ (1.63 g, 5.0 mmol). The reaction was heated at 60° C. under an atmosphere of argon for 2 hours. Upon cooling to room temperature the reaction was diluted with EtOAc and washed with H$_2$O, 10% NaOH, H$_2$O, and brine and dried (MgSO$_4$). Purification by flash column chromatography (silica, 15% EtOAc in hexane) yielded a colorless waxy solid: $^1$H NMR (250 MHz, CDCl$_3$) δ8.05 (d, J=15.8 Hz, 1H, olefin), 7.93 (d, J=8.6 Hz, 2H, phenyl), 7.35 (d, J=8.6 Hz, 2H, phenyl), 7.18 (d, J=8.6 Hz, 1H, pyridyl), 7.06 (d, J=8.6 Hz, 1H, pyridyl), 7.02 (d, J=8.6 Hz, 2H, phenyl), 6.98 (d, J=15.8 Hz, 1H, olefin), 6.78 (d, J=8.6 Hz, 2H, phenyl), 3.92 (t, J=6.5 Hz, 2H, OCH$_2$), 3.85 (s, 3H, methyl ester), 3.75 (s, 3H, OCH$_3$), 3.72 (s, 3H, methyl ester), 3.64 (s, 2H, SCH$_2$), 3.59 (s, 2H, SCH$_2$), 2.49 (t, J=7.6 Hz, 2H, benzylic), 1.78 (m, 2H CH$_2$), 1.40 (m, 10H, aliphatic); MS (CI): 592 (M+H).

18(g). 4-[2-Thia-3-[2-(E-2-carboxyethenyl)-3-[8-(4-methoxyphenyl)octyloxy]-6-pyridyl]propyl]benzoic, acid, dilithium salt Methyl 4-[2-thia-3-[2-(E-2-carboxymethylethenyl)-3-[8-(4-methoxyphenyl)octyloxy]-6-pyridyl]propyl]benzoate (80 mg, 0.13 mmol) was dissolved in tetrahydrofuran (THF) (1.5 mL) and MeOH (1.5 mL) and treated with 1.0M LiOH (0.8 mL, 0.8 mmol). The reaction was stirred under an argon atmosphere for 20 hours. The solvent was evaporated and the product purified by Reversed Phased MPLC (RP-18 silica, H$_2$O—MeOH gradient). Lyophilization yielded a colorless amorphous solid: $^1$H NMR (250 MHz, d$^4$-MeOH) δ7.87 (d, J=8.6 Hz, 2H, phenyl), 7.79 (d, J=15.8 Hz, 1H, olefin), 7.34 (m, 3H, phenyl, pyridyl), 7.23 (d, J=8.6 Hz, 1H, pyridyl), 7.08 (d, J=15.8 Hz, 1H, olefin), 7.06 (d, J=8.6 Hz, 2H, phenyl), 6.80 (d, J=8.6 Hz, 2H, phenyl), 4.04 (t, J=6.5 Hz, 2H, OCH$_2$), 3.74 (s, 2H, SCH$_2$), 3.73 (s, 3H, OCH$_3$), 3.69 (s, 2H, SCH$_2$), 2.55 (t, J=7.6 Hz, 2H, benzylic), 1.87 (m, 2H, CH$_2$), 1.50 (m, 10H, aliphatic); Analysis calcd for C$_{32}$H$_{35}$NO$_6$SLi$_2$. 3H$_2$O: C, 61.04; H, 6.56; N, 2.22; found: C, 60.96; H, 6.35; N, 2.39; MS (FAB): 576 (M+H), 582.3 (M+Li).

EXAMPLE 19

4-[2-Oxythia-3-[2-(E-2-carboxyethenyl)-3-[8-(4-methoxypheneyl)octyloxy]-6-pyridyl]propyl]benzoic acid, dilithium salt 19(a). Methyl 4-[2-oxythia-3-[2-(E-2-carboxymethylethenyl)-3-[8-(4-methoxyphenyl)octyloxy]-6-pyridyl]propyl]benzoate Methyl 4-[2-thia-3-[2-(E-2-carboxymethylethenyl)-3-[8-(4-methoxyphenyl)octyloxy]-6-pyridyl]propyl]benzoate (110 mg, 0.186 mmol) was dissolved in dry CH$_2$Cl$_2$ (4 mL) under an argon atmosphere and cooled to –20° C. To this was added 85% m-chloroperoxybenzoic acid (36 mg, 0.18 mmol) in two portions 15 minutes apart. The reaction was stirred for 15 minutes at –20° C. following the second addition and then quenched with 5% NaHCO$_3$. The product was extracted into CH$_2$Cl$_2$ and the organic extracts were dried (MgSO$_4$). Purification by flash column chromatography (silica, 50% EtOAc in hexane) gave a white solid: $^1$H NMR (250 MHz, CDCl$_3$) δ8.10 (d, J=15.8 Hz, 1H, olefin), 8.07 (d, J=8.6 Hz, 2H, phenyl), 7.50 (d, J=8.6 Hz, 2H, phenyl), 7.28 (d, J=8.6 Hz, 1H, pyridyl), 7.20 (d, J=8.6 Hz, 1H, pyridyl), 7.12 (d, J=8.6 Hz, 2H, phenyl), 7.07 (d, J=15.8 Hz, 1H, olefin), 6.83 (d, J=8.6 Hz, 2H, phenyl), 4.19 (d, J=12.8 Hz, 1H, SCH), 4.12 (d, J=12.8 Hz, 1H, SCH), 4.04 (t, J=6.5 Hz, 2H, OCH$_2$), 3.94 (s, 3H, methyl ester), 3.92 (m, 2H, SCH$_2$), 3.83 (s, 3H, OCH$_3$), 3.79 (s, 3H, methyl ester), 2.56 (t, J=7.6 Hz, 2H, benzylic), 1.87 (m, 2H, CH$_2$), 1.40 (m, 10H, aliphatic); Analysis calcd for C$_{34}$H$_{41}$NO$_7$S: C, 67.19; H, 6.80; N, 2.30; found: C, 66.80; H, 7.12; N, 2.25; MS (CI): 608 (M+H).

19(b). 4-[2-Oxythia-3-[2-(E-2-carboxyethenyl)-3-[8-(4-methoxyphenyl)octyloxy]-6-pyridyl]propyl]benzoic acid, dilithium salt Methyl 4-[2-oxythia-3-[2-(E-2-carboxymethylethenyl)-3-[8-(4-methoxyphenyl)octyloxy]-6-pyridyl]propyl]benzoate (90 mg, 0.148 mmol) was dissolved in THF (1.5 mL) and MeOH (1.5 mL) and treated with 1.0M LiOH (0.8 mL, 0.8 mmol). The reaction was stirred under an argon atmosphere for 20 hours. The solvent was evaporated and the product purified by Reversed Phased MPLC (RP-18 silica, H$_2$O—MeOH gradient). Lyophilization yielded a colorless amorphous solid: $^1$H NMR (250 MHz, d$^4$-MeOH) δ5 7.98 (d, J=8.6 Hz, 2H, phenyl), 7.81 (d, J=15.8 Hz, 1H, olefin), 7.40 (d, J=8.6 Hz, 2H, phenyl), 7.39 (d, J=8.6 Hz, 1H, pyridyl), 7.27 (d, J=8.6 Hz, 1H, pyridyl), 7.09 (d, J=15.8 Hz, 1H, olefin), 7.05 (d, J=8.6 Hz, 2H, phenyl), 6.77 (d, J=8.6 Hz, 2H, phenyl), 4.35 (d, J=12.8 Hz, 1H, SCH), 4.25 (d, J=12.8 Hz, 1H, SCH), 4.06 (m, 4H, OCH$_2$, SCH$_2$), 3.73 (s, 3H, OCH$_3$), 2.52 (t, J=7.6 Hz, 2H, benzylic), 1.86 (m, 2H, CH$_2$), 1.55 (m, 4H, aliphatic), 1.35 (m, 6H, aliphatic); MS (FAB): 592 (M+H), 500 (M+H; free acid).

EXAMPLE 20

3-[2-Thia-3-[2-(E-2-carboxyethenyl)-3-[8-(4-methoxyphenyl)octyloxy]-6-pyridyl]propyl]benzoic acid, dilithium salt 20(a). Methyl 3-mercaptomethylbenzoate To a solution of methyl 3-bromomethylbenzoate (6.9 g, 30 mmol; Lancaster) in dry acetone (10 mL) was added via dropwise addition a solution of thiourea (2.28 g, 30 mmol) in dry acetone (40 mL) at room temperature. After 15 minutes the precipitated thiouronium salt was collected by filtration; the solids were washed with acetone and dried. The thiouronium salt was dissolved in H$_2$O (65 mL) and the pH was adjusted to 10.5 by the addition of 10% NaOH. The mixture was refluxed for 2 hours. After cooling to room temperature the solution was extracted with EtOAc and the organic layer was discarded. The aqueous solution was acidified to pH 1.5 and extracted three times with EtOAc. The organic extracts were dried (MgSO$_4$), filtered and the solvent evaporated. The crude acid was then dissolved in anhydrous MeOH (125 mL), cooled to 0° C., and dry HCl gas was bubbled through the solution for 30 minutes. The reaction was then left for two days at room temperature. The mixture was concentrated in vacuo and the product was purified by flash column chromatography (silica, 5% EtOAc in hexane) providing a colorless oil: $^1$H NMR (250 MHz, CDCl$_3$) δ8.00 (s, 1H, 2-phenyl), 7.91 (d, J=7.6 Hz, 1H, 6-phenyl), 7.52 (d, J=7.6 Hz, 1H, 4-phenyl), 7.39 (dd, J=7.6 Hz, 1H, 5-phenyl), 3.92 (s, 3H, methyl ester), 3.78 (d, J=7.7 Hz, 2H, SCH$_2$), 1.79 (t, J=7.7 Hz, 1H, SH).

20(b). Methyl 3-[2-thia-3-2-(E-2-carboxy-methylethenyl)-3-[8-(4-methoxyphenyl)octyloxy]-6-pyridyl]propyl] benzoate To a cooled (0° C.) solution of SOCl$_2$ (2.5 mL, 35 mmol) in dry toluene (25 mL) under an argon atmosphere was added a solution of 2-(E-2-carboxymethylethenyl)-3-[8-(4-methoxyphenyl)octyloxy]-6-hydroxymethylpyridine (1.5 g, 3.5 mmol) in toluene (10 mL). After 5 minutes the cooling bath was removed and the reaction was stirred for 4 hours at room temperature. The toluene and excess SOCl$_2$ were evaporated. To this was added dry DMF (5 mL), methyl 3-mercaptomethylbenzoate (600 mg, 3.3 mmol), and anhydrous Cs$_2$CO$_3$ (6.6 g, 20 mmol). The reaction was heated at 60° C. under an atmosphere of argon for 1.5 hours. Upon cooling to room temperature the reaction was diluted with EtOAc and washed with H$_2$O, 10% NaOH, H$_2$O, and brine and dried (MgSO$_4$). Purification by flash column chromatography (silica, 15% EtOAc in hexane) yielded a colorless waxy solid: 1H NMR (250 MHz, CDCl$_3$) δ8.07 (d, J=15.8 Hz, 1H, olefin), 7.99 (s, 1H, 2-phenyl), 7.90 (d, J=7.7 Hz, 1H, 6-phenyl), 7.54 (d, J=7.7 Hz, 1H, 4-phenyl), 7.37 (dd, J=7.7 Hz, 1H, 5-phenyl), 7.28 (d, J=8.6 Hz, 1H, pyridyl), 7.14 (d, J=8.6 Hz, 1H, pyridyl), 7.11 (d, J=8.6 Hz, 2H, phenyl), 7.08 (d, J=15.8 Hz, 1H, olefin), 6.82 (d, J=8.6 Hz, 2H, phenyl), 3.99 (t, J=6.5 Hz, 2H, OCH$_2$), 3.91 (s, 3H, methyl ester), 3.81 (s, 3H, OCH$_3$), 3.78 (s, 3H, methyl ester), 3.71 (s, 2H, SCH$_2$), 3.68 (s, 2H, SCH$_2$), 2.55 (t, J=7.6 Hz, 2H, benzylic), 1.78 (m, 2H, CH$_2$), 1.5 (m, 10H, aliphatic); MS (CI): 592.2 (M+H).

20(c). 3-[2-Thia-3-[2-(E-2-carboxyethenyl)-3-[8-(4-methoxyphenyl)octyloxy]-6-pyridyl]propyl]benzoic acid, dilithium salt Methyl 3-[2-thia-3-[2-(E-2-carboxy-methylethenyl)-3-[8-(4-methoxyphenyl)octyloxy]-6-pyridyl]propyl]benzoate (1.5 g, 2.5 mmol) was dissolved in THF (20 mL) and MeOH (20 mL) and treated with 1.0M LiOH (11.5 mL, 11.5 mmol). The reaction was stirred under an argon atmosphere for 20 hours. The solvent was evaporated and the product purified by Reversed Phased MPLC (RP-18 silica, $H_2O$-MeOH gradient). Lyophilization yielded a colorless amorphous solid: $^1$H NMR (250 MHz, $d^4$-MeOH) δ7.96 (s, 1H, 2-phenyl), 7.85 (d, J=7.7 Hz, 1H, 6-phenyl), 7.79 (d, J=15.8 Hz, 1H, olefin), 7.30 (m, 4H, 4,5-phenyl, 4,5-pyridyl), 7.08 (d, J=15.8 Hz, 1H, olefin), 7.06 (d, J=8.6 Hz, 2H, phenyl), 6.80 (d, J=8.6 Hz, 2H, phenyl), 4.04 (t, J=6.5 Hz, 2H, $OCH_2$), 3.74 (s, 2H, $SCH_2$), 3.73 (s, 3H, $OCH_3$), 3.69 (s, 2H, $SCH_2$), 2.55 (t, J=7.6 Hz, 2H, benzylic), 1.87 .(m, 2H, $CH_2$), 1.50 (m, 10H, aliphatic); Analysis calcd for $C_{32}H_{35}NO_6SLi_2$. ⅝$H_2O$: C, 64.32; H, 6.32; N, 2.34; found: C, 64.28; H, 6.24; N, 2.32; MS (FAB): 564.2 (M+H; free acid).

Proceeding in a similar manner, but substituting another alcohol for 8-(4-methoxyphenyl)octan-1-ol, such as 4-(4-methoxyphenyl)butan-1-ol, preparing or purchasing the appropriate mercaptan and the appropriate benzoate or aniline, the following compounds were make:

3-[2-thia-3-[2-(E-2-carboxyethenyl)-3-[4-(4-methoxyphenyl)butyloxy]-6-pyridyl]propyl]benzoic acid, dilithium salt;

2-[2-thia-3-[2-(E-2-carboxyethenyl)-3-[8-(4-methoxyphenyl)octyloxy]-6-pyridyl]propyl]benzoic acid, dilithium salt;

4-[2-thia-3-[2-(E-2-carboxyethenyl)-3-[8-(4-methoxyphenyl)octyloxy]-6-pyridyl]ethyl]phenylacetic acid, dilithium salt;

1-fluoro-3-[2-thia-3-[2-(E-2-carboxyethenyl)-3-[4-(4-methoxyphenyl)butyloxy]-6-pyridyl]propyl]benzene, lithium salt 3-[2-thia-3-[2-(E-2-carboxyethenyl)-3-[4-(4-methoxyphenyl)butyloxy]-6-pyridyl]propyl]benzene, lithium salt 1-fluoro-4-[2-thia-3-[2-(E-2-carboxyethenyl)-3-[4-(4-methoxyphenyl)butyloxy]-6-pyridyl]propyl]benzene, lithium salt 3-[2-thia-3-[2-(E-2-carboxyethenyl)-3-[8-(4-methoxyphenyl)octyloxy]-6-pyridyl]propyl]aniline, dilithium salt;

N-[3-[2-thia-3-[2-(E-2-carboxyethenyl)-3-[8-(4-methoxyphenyl)octyloxy]-6-pyridyl]propyl]phenyltrifluoro-methanesulfonamide; [Mercaptan prepared by the method of Tagawa, H. and Veno, K *Chem. Pharm, Bull.*, 26(5), 1384 (1978)]; and N-[3-[2-thia-3-[2-(E-2-carboxyethenyl)-3-[8-(4-methoxyphenyl)octyloxy]-6-pyridyl]propyl]benzene-methanseulfonamide, [Mercaptan prepared by the method of Lutter, E. *Chem. Ber.*, 30, 1065 (1897)].

EXAMPLE 21

3-[2-Oxythia-3-[2-(E-2-carboxyethenyl)-3-[8-(4-methoxyphenyl)octyloxy]-6-pyridyl]propyl]benzoic acid, dilithium salt and 3-[2-Dioxythia-3-[2-(E-2-carboxyethenyl)-3-[8-(4-methoxyphenyl)octyloxy]-6-pyridyl]propyl]benzoic acid, dilithium salt 21(a). Methyl 3-[2-oxythia-3-[2-(E-2-carboxymethylethenyl )-3-[8-(4-methoxyphenyl)octyloxy]-6-pyridyl]propyl]benzoate and methyl 3-[2-dioxythia-3-[2-(E-2-carboxymethylethenyl)-3-[8-(4-methoxyphenyl) octyloxy]-6-pyridyl]propyl]benzoate.

Methyl 3-[2-thia-3-[2-(E-2-carboxymethylethenyl)-3-[8-(4methoxyphenyl)octyloxy]-6-pyridyl]propyl]benzoate (150 mg, 0.25 mmol) was dissolved in dry $CH_2Cl_2$ (5 mL) under an argon atmosphere and cooled to –20° C. To this was added 85% m-chloroperoxybenzoic acid (52 mg, 0.26 mmol) in two portions 15 minutes apart. The reaction was stirred for 25 minutes at –20° C. following the second addition and then quenched with 5% $NaHCO_3$. The product was extracted into $CH_2Cl_2$ and the organic extracts were dried ($MgSO_4$). Purification by flash column chromatography (silica, 20 and 50% EtOAc in hexane) gave the sulfoxide as a white solid and the sulfone as a white solid.

Sulfoxide: $^1$H NMR (250 MHz, $CDCl_3$) δ8.07 (d, J=1 5.8 Hz, 1H, olefin), 8.01 (s, 1H, 2-phenyl), 7.97 (d, J=7.7 Hz, 1H, 6-phenyl), 7.55 (d, J=7.7 Hz, 1H, 4-phenyl), 7.46 (dd, J=7.7 Hz, 1H, 5-phenyl), 7.28 (d, J=8.6 Hz, 1H, pyridyl), 7.20 (d, J=8.6 Hz, 1H, pyridyl), 7.07(d, J=8.6 Hz, 2H, phenyl), 7.05 (d, J=15.8 Hz, 1H, olefin), 6.78 (d, J=8.6 Hz, 2H, phenyl), 4.12 (d, J=12.8 Hz, 1H, SCH), 4.05 (d, J=12.8 Hz, 1H, SCH), 4.04 (t, J=6.5 Hz, 2H, $OCH_2$), 3.94 (s, 3H, methyl ester), 3.92 (m, 2H, $SCH_2$), 3.83 (s, 3H, $OCH_3$), 3.79 (s, 3H, methyl ester), 2.56 (t, J=7.6 Hz, 2H, benzylic), 1.87 (m, 2H, $CH_2$), 1.40 (m, 10H, aliphatic); Analysis calcd for $C_{34}H_{41}NO_7S$ . ¼$H_2O$: C, 66.70; H, 6.83; N, 2.29; found: C, 66.54; H, 6.68; N, 2.30; MS (CI): 608.2 (M+H);

Sulfone: $^1$H NMR (250 MHz, $CDCl_3$) δ8.23 (s, 1H, 2-phenyl), 8.13 (d, J=15.8 Hz, 1H, olefin), 8.08 (d, J=7.7 Hz, 1H, 6-phenyl), 7.74 (d, J=7.7 Hz, 1H, 4-phenyl), 7.51 (dd, J=7.7 Hz, 1H, 5-phenyl), 7.46 (d, J=8.6 Hz, 1H, pyridyl), 7.24 (d, J=8.6 Hz, 1H, pyridyl), 7.12 (d, J=8.6 Hz, 2H, phenyl), 7.11 (d, J=15.8 Hz, 1H, olefin), 6.84 (d, J=8.6 Hz, 2H, phenyl), 4.30 (s, 4H, $SCH_2$), 4.06 (t, J=6.5 Hz, 2H, $OCH_2$), 3.93 (s, 3H, methyl ester), 3.83 (s, 3H, $OCH_3$), 3.79 (s, 3H, methyl ester), 2.56 (t, J=7.6 Hz, 2H, benzylic), 1.9 (m, 2H, $CH_2$), 1.5 (m, 10H, aliphatic); MS (CI): 624.2 (M+H).

21(b). 3-[2-Oxythia-3-[2-(E-2-carboxyethenyl)-3-[8-(4-methoxyphenyl)octyloxy]-6-pyridyl]propyl]benzoic acid dilithium salt.

Methyl 3-[2-oxythia-3-[2-(E-2-carboxymethylethenyl)-3-[8-(4-methoxyphenyl)octyloxy]-6-pyridyl]propyl]benzoate (100 mg, 0.165 mmol) was dissolved in THF (1.5 mL) and MeOH (1.5 mL) and treated with 1.0M LiOH (0.8 mL, 0.8 mmol). The reaction was stirred under an argon atmosphere for 20 hours. The solvent was evaporated and the product purified by Reversed Phased MPLC (RP-18 silica, $H_2O$-MeOH gradient). Lyophilization yielded a colorless amorphous solid: $^1$H NMR (250 MHz, $d^4$-MeOH) δ7.95 (m, 2H, 2,6-phenyl), 7.82 (d, J=15.8 Hz, 1H, olefin), 7.40 (m, 2H, 4,5-phenyl), 7.37 (d, J=8.6 Hz, 1H, pyridyl), 7.29 (d, J=8.6 Hz, 1H, pyridyl), 7.10 (d, J=15.8 Hz, 1H, olefin), 7.06 (d, J=8.6 Hz, 2H, phenyl), 6.79 (d, J=8.6 Hz, 2H, phenyl), 4.36 (d, J=12.8 Hz, 1H, SCH), 4.25 (d, J=12.8 Hz, 1H, SCH), 4.08 (m, 4H, $OCH_2$, $SCH_2$), 3.73 (s, 3H, $OCH_3$), 2.54 (t, J=7.6 Hz, 2H, benzylic), 1.87 (m, 2H, $CH_2$), 1.55 (m, 4H, aliphatic), 1.37 (m, 6H, aliphatic); Analysis calcd for $C_{32}H_{35}NO_7SLi_2$. ¾$H_2O$: C, 61.68; H, 6.23; N, 2.25; found: C, 61.79; H, 6.10; N, 2.39; MS (FAB): 592.2 (M+H).

This reaction was also used to prepare 3-[2-oxythia-3-[2-(E-2-carboxyethenyl)-3-[4-(4-methoxyphenyl)butyloxy]-6-pyridyl]propyl]benzoic acid, lithium salt.

21(c). 3-[2-Dioxythia-3-[2-(E-2-carboxyethenyl)-3-[8-(4-methoxyphenyl)octyloxy]-6-pyridyl]propyl]benzoic acid, dilithium salt.

Methyl 3-[2-dioxythia-3-[2-(E-2-carboxymethylethenyl)-3-[8-(4-methoxyphenyl)octyloxy]-6-pyridyl]propyl] benzoate (20 mg, 0.0321 mmol) was dissolved in THF (0.5 mL) and MeOH (0.5 mL) and treated with 1.0M LiOH (0.2 mL, 0.2 mmol). The reaction was stirred under an argon atmosphere for 20 hours. The solvent was evaporated and the product purified by Reversed Phased MPLC (RP-18 silica, H$_2$O-MeOH gradient). Lyophilization yielded a colorless amorphous solid: $^1$H NMR (250 MHz, d$^4$-MeOH) δ8.08 (s, 1H, 2-phenyl), 7.96 (d, J=7.7 Hz, 1H, 6-phenyl), 7.85 (d, J=15.8 Hz, 1H, olefin), 7.58 (d, J=7.7 Hz 1H, 4-phenyl), 7.39 (m, 3H, 5-phenyl, 4,5-pyridyl), 7.13 (d, J=15.8 Hz, 1H, olefin), 7.08 (d, J=8.6 Hz, 2H, phenyl), 6.82 (d, J=8.6 Hz, 2H, phenyl), 4.86 (s, 4H, SCH$_2$), 4.10 (t, J=6.5 Hz, 2H, OCH$_2$), 3.75 (s, 3H, OCH$_3$), 2.52 (t, J=7.6 Hz, 2H, benzylic 1.87 (m, 2H, CH$_2$), 1.55 (m, 4H, aliphatic), 1.40 (m, 6H, aliphatic); Analysis calcd for C$_{32}$H$_{35}$NO$_8$SLi$_2$. ¾ H$_2$O: C, 59.30; H, 6.14; N, 2.16; found: C, 59.29; H, 6.20; N, 2.39; MS (FAB): 608.2 (M+H).

This reaction can also be used to make other sulfoxides and sulfones of this inventions including 3-[2-dioxythia-[2-(E-2-carboxyethenyl)-3-[4-(4-methoxyphenyl)butyloxy]-6-pyridyl]propyl]benzoic acid, dilithium salt, and 3-[2-oxythia-[2-(E-2-carboxyethenyl)-3-[4-(4-methoxyphenyl)butyloxy]-6-pyridyl]propyl]benzoic acid, dilithium salt.

EXAMPLE 22

3-[2-Thia-3-[2-(2-carboxyethanyl)-3-[8-(4-methoxyphenyl)octyloxy]-6-pyridyl]propyl]benzoic acid, dilithium salt 22(a)2-(2-Carboxymethylethanyl)-3-[8-(4-methoxyphenyl)-octyloxy-6-hydroxymethylpyridine. 2-(E-2-Carboxymethyl-ethenyl)-3-[8-(4-methoxyphenyl) octyloxy]-6-hydroxymethylpyridine (300 mg, 0.702 mmol) was dissolved in MeOH (3 mL) and treated with 5% Pd-C catalyst (30 mg). The reaction was stirred under an atmosphere of H$_2$ (balloon pressure) for 5 hours. The reaction was diluted with CH$_2$Cl$_2$, and filtered through Celite, and concentrated. Purification by flash column chromatography (silica, EtOAc:CH$_2$Cl$_2$:hexane, 25:50:25) gave a pale yellow oil: $^1$H NMR (250 MHz, CDCl$_3$) δ7.09 (m, 4H, phenyl, pyridyl), 6.80 (d, J=8.6 Hz, 2H, phenyl), 4.62 (s, 2H, CH$_2$), 3.93 (t, J=6.5 Hz, 2H, OCH$_2$), 3.77 (s, 3H, OCH$_3$), 3.68 (s, 3H, methyl ester), 3.16 (dd, J=7.3, 7.2 Hz, 2H, CH$_2$), 2.77 (dd, J=7.3, 7.2 Hz, 2H, CH$_2$), 2.54 (t, J=7.6 Hz, 2H, benzylic), 1.79 (m, 2H, CH$_2$), 1.57 (m, 2H, CH$_2$), 1.44 (m, 2H, CH$_2$), 1.34 (m, 6H, aliphatic); MS (CI): 430.2 (M+H).

22(b). Methyl 3-[2-thia-3-[2-(2-carboxymethylethanyl)-3-[8-(4-methoxyphenyl)octyloxy]-6-pyridyl]propyl]benzoate.

To a cooled (0° C.) solution of SOCl$_2$ (0.17 mL, 2.33 mmol) in dry toluene (1.5 mL) under an argon atmosphere was added 2-(carboxymethylethanyl)-3-[8-(4-methoxyphenyl)octyloxy]-6-hydroxymethylpyridine (100 mg, 0.233 mmol). After 5 minutes the cooling bath was removed and the reaction was stirred for 1.5 hours at room temperature. The toluene and excess SOCl$_2$ were evaporated. To this was added dry DMF (0.5 mL), methyl 3-mercaptomethylbenzoate (47 mg, 0.258 mmol), and anhydrous Cs$_2$CO$_3$ (380 mg, 1.16 mmol). The reaction was heated at 60° C. under an atmosphere of argon for 1 hour. Upon cooling to room temperature the reaction was diluted with EtOAc and washed with H$_2$O, 10% NaOH, H$_2$O, and brine and dried (MgSO$_4$). Purification by flash column chromatography (silica, EtOAc:CH$_2$C$_{12}$:hexane, 15:25:65) yielded a pale yellow oil: $^1$H NMR (250 MHz, CDCl$_3$) δ7.99 (s, 1H, 2-phenyl), 7.92 (d, J=7.7 Hz, 1H, 6-phenyl), 7.54 (d, J=7.7 Hz, 1H, 4-phenyl), 7.37 (dd, J=7.7 Hz, 1H, 5-phenyl), 7.09 (m, 4H, pyridyl, phenyl), 6.88 (d, J=8.6 Hz, 2H, phenyl), 3.93 (t, J=6.5 Hz, 2H, OCH$_2$), 3.91 (s, 3H, methyl ester), 3.78 (s, 3H, OCH$_3$), 3.71 (s, 2H, SCH$_2$), 3.65 (s, 3H, methyl ester), 3.64 (s, 2H, SCH$_2$), 3.14 (dd, J=7.3, 7.2 Hz, 2H, CH$_2$), 2.79 (dd, J=7.3, 7.2 Hz, 2H, CH$_2$), 2.55 (t, J=7.6 Hz, 2H, benzylic), 1.80 (m, 2H, CH$_2$), 1.58 (m, 2H, CH$_2$), 1.45 (m, 2H, CH$_2$), 1.34 (m, 6H, aliphatic); Analysis calcd for C$_{34}$H$_{43}$NO$_6$S: C, 68.77; H, 7.30; N, 2.36; found: C, 68.87; H, 7.21; N, 2.17; MS (CI): 594.6 (M+H).

22(c). 3-[2-Thia-3-[2-(2-carboxyethanyl)-3-[8-(4-methoxyphenyl)octyloxy]-6-pyridyl]propyl]benzoic acid, dilithium salt.

Methyl 3-[2-thia-3-[2-(2-carboxymethylethanyl)-3-[8-(4-methoxyphenyl)octyloxy]-6-pyridyl]propyl]benzoate (116 mg, 0.195 mmol) was dissolved in THF (2.25 mL) and MeOH (0.75 mL) and treated with 1.0M LiOH (0.75 mL, 0.75 mmol). The reaction was stirred under an argon atmosphere for 20 hours. The solvent was evaporated and the product purified by Reversed Phased MPLC (RP-18 silica, H$_2$O-MeOH gradient). Lyophilization yielded a colorless amorphous solid: $^1$H NMR (250 MHz, d$^4$-MeOH) δ7.90 (s, 1H, 2-phenyl), 7.83 (d, J=7.7 Hz, 1H, 6-phenyl), 7.34 (m, 2H, 4,5-phenyl), 7.25 (d, J=8.6 Hz, 1H, pyridyl), 7.14 (d, J=8.6 Hz, 1H, pyridyl), 7.07 (d, J=8.6 Hz, 2H, phenyl), 6.83 (d, J=8.6 Hz, 2H, phenyl), 4.01 (t, J=6.5 Hz, 2H, OCH$_2$), 3.77 (s, 3H, OCH$_3$), 3.73 (s, 2H, SCH$_2$), 3.71 (s, 2H, SCH$_2$), 3.07 (dd, J=7.3, 7.2 Hz, 2H, CH$_2$), 2.47 (m, 4H, CH$_2$, benzylic), 1.81 (m, 2H, CH$_2$), 1.50 (m, 4H, aliphatic), 1.30 (m, 6H, aliphatic); Analysis calcd for C$_{32}$H$_{37}$NO$_6$SLi$_2$. ¾ H$_2$O: C, 62.18; H, 6.77; N, 2.27; found: C, 61.93; H, 6.48; N, 2.10; MS (ES): 566 (M+H; free acid), 564 (M–H; free acid).

In a similiar manner, the following compounds were made:

3-[1-thia-2-[2-(2-carboxyethanyl)-3-[4-(4-methoxyphenyl)butyloxy]-6-pyridyl]ethyl]benzene, lithium salt;
3-[2-thia-3-[2-(2-carboxyethanyl)-3-[4-(4-methoxyphenyl)butyloxy]-6-pyridyl]propyl]benzene, lithium salt; and
1-fluoro-4-[2-thia-3-[2-(2-carboxyethanyl)-3-[4-(4-methoxyphenyl)butyloxy]-6-pyridyl]propyl]benzene, lithium salt.

EXAMPLE 23

4-[2-Thia-3-[2-(E-2-carboxyethenyl)-3-[8-(4-methoxyphenyl)octyloxy]-6-pyridyl]propyl] phenylacetic acid, dilithium salt 23(a). Methyl 4-mercaptomethylphenylacetate.

4-Bromomethyl-phenylacetic acid (1 g, 4.4 mmol) and thiourea (334 mg, 4.4 mmol) were heated (35°–40° C.) in acetone (20 mL) until a homogeneous solution resulted. Upon cooling to room temperature the thiouronium salt precipitated. The solvent was evaporated and the residue suspended in H$_2$O (10 mL). The pH was adjusted to 12 with 10% NaOH. The mixture was then refluxed for two hours. The solution was acidified with 6N HCl and the product was extracted into EtOAc. The organic extracts were washed with H$_2$O and dried (MgSO$_4$). The crude acid was dissolved in MeOH (20 mL) and treated with conc. H$_2$SO$_4$ (0.33 mL); the reaction was refluxed for 1.5 hours. Upon cooling to room temperature the reaction was diluted with H$_2$O and the product was extracted into EtOAc. The organic extracts were washed with H$_2$O and dried (MgSO$_4$). The methyl ester was obtained as an oil; crude product was used without further purification: $^1$H NMR (250 MHz, CDCl$_3$) δ7.23 (m, 4H, aryl), 3.71 (d, J=7.6 Hz, 2H, SCH$_2$), 3.68 (s, 3H, methyl ester), 3.60 (s, 2H, CH$_2$), 1.74 (t, J=7.6 Hz, 1H, SH); IR (film) n$_{max}$ 2570 (SH), 1740 (CO) cm$^{-1}$.

23(b). Methyl 4-[2-thia-3-[2-(E-2-carboxymethylethenyl)-3-[8-(4-methoxyphenyl)octyloxy]-6-pyridyl]propyl]phenylacetate.

To a cooled (0° C.) solution of SOCl₂ (0.44 mL, 6.2 mmol) in dry toluene (7 mL) under an argon atmosphere was added 2-(E-2-carboxymethylethenyl)-3-[8-(4-methoxyphenyl)octyloxy]-6-hydroxymethylpyridine (270 mg, 0.62 mmol). After 5 minutes the cooling bath was removed and the reaction was stirred for 2 hours at room temperature. The toluene and excess SOCl₂ were evaporated. To this was added dry DMF (3 mL), methyl 4-mercapto-methylphenylacetate (183 mg, 0.93 mmol), and anhydrous Cs₂CO₃ (907 mg, 2.79 mmol). The reaction was heated at 60° C. under an atmosphere of argon for 1 hour. Upon cooling to room temperature the reaction was diluted with EtOAc and washed with H₂O, 10% NaOH, HO₂O, and brine and dried (MgSO₄). Purification by flash column chromatography (silica, 20% EtOAc in hexane) yielded a pale yellow oil: ¹H NMR (250 MHz, CDCl₃) δ8.08 (d, J=15.8 Hz, 1H, olefin), 7.22 (m, 6H, phenyl, pyridyl), 7.12 (d, J=8.6 Hz, 2H, phenyl), 7.07 (d, J=15.8 Hz, 1H, olefin), 6.83 (d, J=8.6 Hz, 2H, phenyl), 4.00 (t, J=6.5 Hz, 2H, OCH₂), 3.82 (s, 3H, methyl ester), 3.78 (s, 3H, OCH₃), 3.70 (s, 3H, methyl ester), 3.68 (s, 2H, SCH₂), 3.67 (s, 2H, SCH₂), 3.62 (s, 2H, CH₂), 2.55 (t, J=7.6 Hz, 2H, benzylic), 1.85 (m, 2H, CH₂), 1.60 (m, 2H, CH₂) 1.50 (m, 2H, CH₂), 1.37 (m, 6H, aliphatic); MS (CI): 605 (M+H).

23(c). 4-[2-Thia-3-[2-(E-2-carboxyethenyl)-3-[8-(4-methoxyphenyl)octyloxy]-6-pyridyl]propyl]phenylacetic acid, dilithium salt.

Methyl 4-[2-thia-3-[2-(E-2-carboxymethyl-ethenyl)-3-[8-(4-methoxyphenyl)octyloxy]-6-pyridyl]propyl]phenylacetate (100 mg, 0.165 mmol) was dissolved in THF (1.4 mL) and MeOH (0.5 mL) and treated with 1.0M LiOH (0.5 mL, 0.5 mmol). The reaction was stirred under an argon atmosphere for 20 hours. The solvent was evaporated and the product purified by Reversed Phased MPLC (RP-18 silica, H₂O-MeOH gradient). Lyophilization yielded a colorless amorphous solid: ¹H NMR (250 MHz, d⁴-MeOH) δ7.76 (d, J=15.8 Hz, 1H, olefin), 7.21 (m, 6H, phenyl, pyridyl), 7.06 (d, J=8.6 Hz, 2H, phenyl), 7.05 (d, J=15.8 Hz, 1H, olefin), 6.77 (d, J=8.6Hz, 2H, phenyl), 4.02 (t, J=6.5 Hz, 2H, OCH₂), 3.72 (s, 3H, OCH₃), 3.66 (s, 4H, SCH₂), 3.44 (s, 2H, CH₂), 2.51 (t, J=7.6 Hz, 2H, benzylic), 1.86 (m, 2H, CH₂), 1.53 (m, 4H, aliphatic), 1.34 (m, 6H, aliphatic); MS (FAB): 578.2 (M+H; free acid).

EXAMPLE 24

4-[2-Oxythia-3-[2-(E-2-carboxyethenyl)-3-[8-(4-methoxyphenyl)octyloxy]-6-pyridyl]propyl]phenylacetic acid, dilithium salt 24(a). Methyl 4-[2-oxythia-3-[2-(E-2-carboxymethylethenyl)-3-[8-(4-methoxyphenyl)octyloxy]-6-pyridyl]propyl]phenylacetate.

Methyl 4-[2-thia-3-[2-(E-2-carboxymethylethenyl)-3-[8-(4-methoxyphenyl)octyloxy]-6-pyridyl]propyl]phenylacetate (171 mg, 0.28 mmol) was dissolved in dry CH₂Cl₂ (5 mL) under an argon atmosphere and cooled to −10° C. To this was added 85% m-chloroperoxybenzoic acid (67 mg, 0.31 mmol) in two portions 15 minutes apart. The reaction was stirred for 20 minutes at −10° C. following the second addition and then quenched with aq NaHCO₃. The product was extracted into EtOAc and the organic extracts were washed with H₂O and brine and dried (MgSO₄). Purification by flash column chromatography (silica, 30% EtOAc in hexane) gave the sulfoxide as a white solid: ¹H NMR (250 MHz, CDCl₃) δ8.00 (d, J=15.8 Hz, 1H, olefin), 7.30 (d, J=8.2 Hz, 2H, phenyl), 7.23 (d, J=8.2 Hz, 2H, phenyl), 7.20 (d, J=8.6 Hz, 1H, pyridyl), 7.13 (d, J=8.6 Hz, 1H, pyridyl), 7.01 (d, J=8.6 Hz, 2H, phenyl), 6.98 (d, J=15.8 Hz, 1H, olefin), 6.76 (d, J=8.6 Hz, 2H, olefin), 4.05 (d, J=12.9 Hz, 1H, SCH), 4.02 (d, J=12.9 Hz, 1H, SCH), 3.94 (t, J=6.5 Hz, 2H, OCH₂), 3.83 (d, J=12.9 Hz, 1H, SCH), 3.80 (d, J=12.9 Hz, 1H, SCH), 3.74 (s, 3H, methyl ester), 3.70 (s, 3H, OCH₃), 3.62 (s, 3H, methyl ester), 3.56 (s, 2H, CH₂), 2.47 (t, J=7.6 Hz, 2H, benzylic), 1.78 (m, 2H, CH₂), 1.57 (m, 2H, CH₂), 1.39 (m, 2H, CH₂), 1.28 (m 6H, aliphatic); MS (FAB): 622.3 (M+H); mp 87°–89° C.

24(b). 4-[2-Oxythia-3-[2-(E-2-carboxyethenyl)-3-[8-(4-methoxyphenyl)octyloxy]-6-pyridyl]propyl]phenylacetic acid, dilithium salt.

Methyl 4-[2-oxythia-3-[2-(E-2-carboxy-methylethenyl)-3-[8-(4-methoxyphenyl)octyloxy]-6-pyridyl]-propyl]phenylacetate (110 mg, 0.177 mmol) was dissolved in THF (1.0 mL) and MeOH (0.53 mL) and treated with 1.0M LiOH (0.53 mL, 0.53 mmol). The reaction was stirred under an argon atmosphere for 20 hours. The solvent was evaporated and the product purified by Reversed Phased MPLC (RP-18 silica, H₂O-MeOH gradient). Lyophilization yielded a colorless amorphous solid: ¹H NMR (250 MHz, d⁴-MeOH) δ7.79 (d, J=15.8 Hz, 1H, olefin), 7.34 (m, 6H, phenyl, pyridyl), 7.09 (d, J=15.8 Hz, 1H, olefin), 7.06 (d, J=8.6 Hz, 2H, phenyl), 6.79 (d, J=8.6 Hz, 2H, phenyl), 4.29 (d, J=12.9 Hz, 1H, SCH) 4.18 (d, J=12.9 Hz, 1H, SCH), 4.04 (m, 4H, SCH₂, OCH₂), 3.73 (s, 3H, OCH₃), 3.48 (s, 2H, CH₂), 2.55 (t, J=7.6 Hz, 2H, benzylic), 1.85 (m, 2H, CH₂), 1.55 (m, 4H, aliphatic), 1.35 (m, 6H, aliphatic); MS (FAB): 606.3 (M+H), 594.4 (M+H; free acid).

EXAMPLE 25

3-[2-Thia-3-[2-(E-2-carboxyethenyl)-3-(8-(4-methoxyphenyl)octyloxy)-6-pyridyl]propyl-N,N-dimethylbenzamide, lithium salt 25(a). 3-[2-Thia-3-[2-(E-2-carboxymethylethenyl)-3-(8-(4-methoxyphenyl)octyloxy)-6-pyridyl]propyl]benzoic acid.

To a cooled (0° C.) solution of SOC₁₂ (0.85 mL, 11.7 mmol) in dry toluene (5 mL) under an argon atmosphere was added a solution of 2-(E-2-carboxymethylethenyl)-3-[8-(4-methoxyphenyl)octyloxy]-6-hydroxymethylpyridine (500 mg, 1.17 mmol) in toluene (6 mL). After 5 minutes the cooling bath was removed and the reaction was stirred for 2 hours at room temperature. The toluene and excess SOCl₂ were evaporated. To this was added dry DMF (2 mL), 3-mercaptomethyl-benzoic acid (216 mg, 1.29 mmol) in DMF (2 mL), and anhydrous Cs₂CO₃ (3.8 g, 11.7 mmol). The reaction was heated at 60° C. under an atmosphere of argon for 6 hours. Upon cooling to room temperature the reaction was diluted with H₂O and washed with EtOAc. The aqueous phase was acidified to pH 1.2 and extracted with EtOAc. The combined organic extracts were washed with H₂O, and brine and dried (MgSO₄). Purification by flash column chromatography (silica, 5% MeOH in CH₂Cl₂) yielded a pale yellow oil: ¹H NMR (250 MHz, CDCl₃) δ8.07 (d, J=15.7 Hz, 1H, olefin), 8.05 (s, 1H, 2-phenyl), 7.96 (d, J=7.6 Hz, 1H, 6-phenyl), 7.58 (d, J=7.6 Hz, 1H, 4-phenyl), 7.39 (dd, J=7.6 Hz, 1H, 5-phenyl), 7.24 (d, J=8.6 Hz, 1H, pyridyl), 7.13 (d, J=8.6 Hz, 1H, pyridyl), 7.08 (d, J=8.6 Hz, 2H, phenyl), 7.06 (d, J=15.7 Hz, 1H, olefin), 6.82 (d, J=8.6 Hz, 2H, phenyl), 4.01 (t, J=6.5 Hz, 2H, O—CH₂), 3.81 (s, 3H, methyl ester) 3.78 (s, 3H, OMe), 3.72 (s, 2H, S—CH₂), 3.69 (s, 2H, S—CH₂), 2.52 (t, J=7.6 Hz, 2H, benzylic), 1.85 (m, 2H, CH₂), 1.57 (m, 2H, CH₂), 1.49 (m, 2H, CH₂), 1.35 (m, 6H, aliphatic).

25(b). 3-[2-Thia-3-[2-(E-2-carboxymethylethenyl)-3-(8-(4-methoxyphenyl)octyloxy)-6-pyridyl]propyl]-N,N-dimethylbenzamide.

3-[2-Thia-3-[2-(E-2-carboxymethylethenyl)-3-(8-(4-methoxyphenyl)octyloxy)-6-pyridyl]propyl]benzoic acid (98 mg, 0.17 mmol) was dissolved in $SOCl_2$ (5 mL) and refluxed for 1 hour. The excess $SOCl_2$ was removed in vacuo. The resulting acid chloride was dissolved in dry $CH_2Cl_2$ (5 mL), cooled to 0° C., and treated with triethylamine (52 mL, 0.37 mmol). Diethylamine was then introduced into the reaction via a cooling finger, reaction was stirred for 15 minutes. The solvent was removed in vacuo and the product was purified by flash column chromatography (silica, 35% EtOAc in hexane) to give a pale yellow oil: $^1H$ NMR (250 MHz, $CDCl_3$) δ8.07 (d, J=15.7 Hz, 1H, olefin), 7.38 (m, 4H, 4,5,6-phenyl, pyridyl), 7.29 (s, 1H, 2-phenyl), 7.20 (d, J=8.6 Hz, 1H, pyridyl), 7.11 (d, J=8.6 Hz, 2H, phenyl), 7.03 (d, J=15.7 Hz, 1H, olefin), 6.82 (d, J=8.6 Hz, 2H, phenyl), 4.02 (t, J=6.5 Hz, 2H, O—$CH_2$), 3.82 (s, 3H, methyl ester), 3.78 (s, 3H, OMe), 3.70 (s, 2H, S—$CH_2$), 3.68 (s, 2H, S—$CH_2$), 3.12 (s, 3H, N—Me), 2.97 (s, 3H, N—Me), 2.55 (t, J=7.6 Hz, 2H, benzylic), 1.86 (m, 2H, $CH_2$), 1.6–1.3 (m, 10H, aliphatic).

25(c). 3-[2-Thia-3-[2-(E-2-carboxyethenyl)-3-(8-(4-methoxyphenyl)octyloxy)-6-pyridyl]propyl]-N,N-dimethylbenzamide, lithium salt.

3-[2-Thia-3-[2-(E-2-carboxymethylethenyl)-3-(8-(4-methoxyphenyl)octyloxy)-6-pyridyl]propyl]-N,N-dimethylbenzamide (80 mg, 0.132 mmol) was dissolved in THF (1.5 mL) and MeOH (1.5 mL) and treated with 1.0M LiOH (0.4 mL, 0.4 mmol). The reaction was stirred under an argon atmosphere for 24 hours. The solvent was evaporated and the product purified by Reversed Phased MPLC (RP-18 silica, $H_2O$-MeOH gradient). Lyophilization yielded a colorless amorphous solid: $^1H$ NMR (250 MHz, $d^4$-MeOH) δ7.79 (d, J=15.7 Hz, 1H, olefin), 7.33 (m, 6H, 2,4,5,6-phenyl, 4,5-pyridyl), 7.07 (d, J=8.6 Hz, 2H, phenyl), 7.05 (d, J=15.7 Hz, olefin), 6.80 (d, J=8.6 Hz, 2H, phenyl), 4.03 (t, J=6.5 Hz, 2H, O—$CH_2$), 3.76 (s, 2H, S—$CH_2$), 3.74 (s, 3H, OMe), 3.69 (s, 2H, S—$CH_2$), 3.09 (s, 3H, N—Me), 2.97 (s, 3H, N—Me), 2.52 (t, J=7.6 Hz, 2H, benzylic), 1.86 (m, 2H, $CH_2$), 1.54 (m, 4H, aliphatic), 1.36 (m, 6H, aliphatic).

EXAMPLE 26

5-[3-[2-Thia-3-[2-(E-2-carboxyethenyl)-3-[8-(4-methoxyphenyl)octyloxy]-6-pyridyl]propyl]phenyl] tetrazole, dilithium salt This tetrazole is prepared via the acid chloride described above according to Duncia, Pierce, and Santella, *J. Org. Chem.*, 1991,56, 2395–2400.

EXAMPLE 26bis (E)-Sodium 3-[3-[4-(4-methoxyphenyl)butyloxy]-6-[phenylthiomethyl]-2-pyridinyl]-2-propenoate 26bis(a) (E)-Methyl 3-[3-[4-(4-methoxyphenyl)butyloxy]-6-[phenlthiomethyl]-2-pyridinyl]-2-propenoate.

Thiophenol (0.017 mL, 0.166 mmol) was dissolved in dry MeCN (0.30 mL) and treated with 2-(E-2-carboxymethylethenyl)-3-[4-(4-methoxyphenyl)butyloxy]-6-chloromethylpyridine hydrochloride (65 mg, 0.152 mmol) and 1,8-diazabicyclo[5.4.0]undec-7-ene (DBU, 0.08 mL, 0.532 mmol). The reaction was stirred under an atmospere of argon at 50° C. for 3 h. The reaction solution was diluted with EtOAc and washed with $H_2O$ and brine and dried ($MgSO_4$). Purification by flash column chromatography (silica, EtOAc: $CH_2Cl_2$:hexane, 10:15:75) gave a colorless waxy solid: $^1H$ NMR (250 MHz, $CDCl_3$) δ8.04 (d, J=15.7 Hz, 1H, vinyl), 7.36–7.07 (m, 9H, aryl), 6.99 (d, J=15.7 Hz, 1H, vinyl), 6.83 (d, J=8.7 Hz, 2H, phenyl), 4.21 (s, 2H, $CH_2$—S), 3.97 (t, J=6.1 Hz, 2H, $CH_2$—O), 3.81 (s, 3H, OMe), 3.78 (s, 3H, methyl ester), 2.64 (t, J=7.2 Hz, 2H, benzylic), 1.81 (m, 4H, $CH_2CH_2$); analysis calcd. for $C_{27}H_{29}NO_4S$ . ⅜$H_2O$: C, 68.95; H, 6.38; N, 2.98; found: C, 68.89; H, 6.23; N, 2.94; MS (ES+): 464.2 (M+H).

26bis(b) (E)-Sodium 3-[3-[4-(4-methoxyphenyl)butyloxy]-6-[phenylthiomethyl]-2-pyridinyl]-2-propenoate.

(E)-Methyl 3-[3-[4-(4-methoxyphenyl)butyloxy]-6-[phenylthiomethyl]-2-pyridinyl]-2-propenoate (55 mg, 0.119 mmol) was dissolved in THF (1.0 mL) and MeOH (0.30 mL) and treated with 1.0M NaOH (0.25 mL, 0.25 mmol). The reaction was stirred under an argon atmosphere for 20 h. The solvent was evaporated and the product purified by Reversed Phased MPLC (RP-18 silica, $H_2O$-MeOH gradient). Lyophilization yielded the captioned product as a colorless amorphous solid: $^1H$ NMR (250 MHz, $d^6$-DMSO) δ7.42 (d, J=15.7 Hz, 1H, vinyl), 7.40–7.20 (m, 7H, aryl), 7.12 (d, J=8.7 Hz, 2H, phenyl), 6.83 (d, J=8.7 Hz, 2H, phenyl), 6.82 (d, J=15.7 Hz, 1H, vinyl), 4.26 (s, 2H, $CH_2$—S), 4.01 (t, J=6.1 Hz, 2H, $CH_2$—O), 3.71 (s, 3H, OMe), 2.61 (t, J=7.2 Hz, 2H, benzylic), 1.73 (m, 4H, $CH_2CH_2$); analysis calcd. for $C_{26}H_{26}NO_{4}SNa$ . ¾$H_2O$: C, 64.38; H, 5.71; N, 2.89; found: C, 64.46; H, 6.04; N, 2.97; MS (ES+): 450.2 (M+H, free acid), (ES–): 448.0 (M–H, free acid).

Proceeding in a similar manner, the following compounds were made:

(E)-lithium 3-[3-[4-(4-methoxyphenyl)butyloxy]-6-[(2-chlorophenylthio)methyl]-2-pyridinyl]-2-propenoate (E)-lithium 3-[3-[4-(4-methoxyphenyl)butyloxy]-6-[(3,4-dichlorophenylthio)methyl]-2-pyridinyl]-2-propenoate (E)-lithium 3-[3-[4-(4-methoxyphenyl)butyloxy]-6-[(4-chlorophenylthio)methyl]-2-pyridinyl]-2-propenoate, (E)-sodium 3-[3-[4-(4-methoxyphenyl)butyloxy]-6-[(4-fluorophenylthio)methyl]-2-pyridinyl]-2-propenoate, (E)-sodium 3-[3-[4-(4-methoxyphenyl)butyloxy]-6-[(3-chlorophenylthio)methyl]-2-pyridinyl]-2-propenoate, (E)-sodium 3-[3-[4-(4-methoxyphenyl)butyloxy]-6-[(2-chlorobenzylthio)methyl]-2-pyridinyl]-2-propenoate, (E)-sodium 3-[3-[4-(4-methoxyphenyl)butyloxy]-6-[(2-methoxyphenylthio)methyl]-2-pyridinyl]-2-propenoate, (E)-sodium 3-[3-[4-(4-methoxyphenyl)butyloxy]-6-[(2,4-dichlorophenylthio)methyl]-2-pyridinyl]-2-propenoate, (E)-sodium 3-[3-[4-(4-methoxyphenyl)butyloxy]-6-[(2-bromophenylthio)methyl]-2-pyridinyl]-2-propenoate, (E)-sodium 3-[3-[4-(4-methoxyphenyl)butyloxy]-6-[(2-methylphenylthio)methyl]-2-pyridinyl]-2-propenoate.

EXAMPLE 27

Formulations for pharmaceutical use incorporating compounds of the present invention can be prepared in various forms and with numerous excipients. Means for making various formulations can be found in standard texts such as Remington's Pharmaceutical Sciences, and similar publications and compendia. Specific examples of formulations are given below.

Tablets

| Ingredients | Per Tablet | Per 10,000 Tablets |
| --- | --- | --- |
| 1. Active ingredient (Cmpd of Form. I) | 40 mg | 400 g |
| 2. Corn Starch | 20 mg | 200 g |
| 3. Alginic acid | 20 mg | 200 g |
| 4. Sodium alginate | 20 mg | 200 g |
| 5. Magnesium stearate | 1.3 mg | 13 g |
| | 101.3 mg | 1013 g |

Procedure for making tablets:

Step 1. Blend ingredients No. 1, No. 2, No. 3 and No. 4 in a suitable mixer/blender.

Step 2. Add sufficient water portionwise to the blend from Step 1 with careful mixing after each addition. Such additions of water and mixing until the mass is of a consistency to permit its conversion to wet granules.

Step 3. The wet mass is converted to granules by passing it through an oscillating granulator using a No. 8 mesh (2.38 mm) screen.

Step 4. The wet granules are then dried in an oven at 410° F. (60° C.) until dry.

Step 5. The dry granules are lubricated with ingredient No. 5.

Step 6. The lubricated granules are compressed on a suitable tablet press.

Suppositories:

| Ingredients | Per Supp. | Per 1000 Supp. |
| --- | --- | --- |
| 1. Formula I compound Active ingredient | 4.0 mg | 40 g |
| 2. Polyethylene Glycol 1000 | 135.0 mg | 1,350 g |
| 3. polyethylene glycol 4000 | 45.0 mg | 450 g |
| | 184.0 mg | 1,840 g |

Procedure:

Step 1. Melt ingredient No. 2 and No. 3 together and stir until uniform.

Step 2. Dissolve ingredient No. 1 in the molten mass from Step 1 and stir until uniform.

Step 3. Pour the molten mass from Step 2 into supository moulds and chill.

Step 4. Remove the suppositories from moulds and wrap.

EXAMPLE 28

Inhalation Formulation

A compound of formula I, 1 to 10 mg/ml, is dissolved in isotonic saline and aerosolized from a nebulizer operating at an air flow adjusted to deliver the desired amount of drug per use.

EXAMPLE 29

Topical formulations

Formulations for pharmaceutical use incorporating compounds of the present invention can be prepared in various forms and with numerous excipients. Means for making various formulations can be found in standard texts such as Remington's Pharmaceutical Sciences, and similar publications and compendia. Specific examples of formulations are given below.

Ointments
Hydrophyllic Petrolatum

| Ingredients | Amount (% Weight/weight) |
| --- | --- |
| Cholesterol | 30.0 g |
| Stearyl Alcohol | 30.0 g |
| White Wax | 78.0 g |
| Active Ingredient | 2.0 g |
| White Petolatum | 860.0 g |

The stearyl alcohol, white wax and white petrolatum are melted together (steam bath for example) and cholesterol and the active ingredient are added. Stirring is commenced and continued until the solids disappear. The source of heat is removed and the mix allowed to congeal and packaged in metal or plastic tubes.

Emulsion Ointment

| Ingredients | Amount (% W/W) |
| --- | --- |
| Methylparaben | 0.25 g |
| Propylparaben | 0.15 |
| Sodium Lauryl Sulfate | 10.0 g |
| Active Ingredient | 5.0 g |
| Propylene Glycol | 120.0 g |
| Stearyl Alcohol | 250.0 g |
| White Petrolatum | 250.0 g |
| Purified Water | QS to 1000.0 g |

The stearyl alcohol and white petrolatum are combined over heat. Other ingredients are dissolved in water, then this solution is added to the warm (ca 50° to 100° C.) alcohol/petrolatum mixture and stirred until the mixture congeals. It can then be packed in tubes or another appropriate package form.

What is claimed is:

1. A compound of formula I

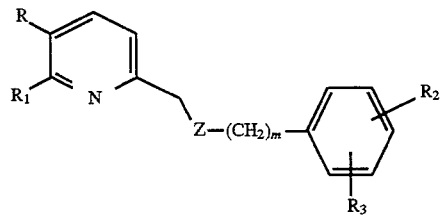

or an N-oxide, or a pharmaceutically acceptable salt where Z is NH, or NCH$_3$, m is 0–5;

R is $C_1$ to $C_{20}$-aliphatic, unsubstituted or substituted phenyl $C_1$ to $C_{10}$-aliphatic where substituted phenyl has one or more radicals selected from the group consisting of lower alkoxy, lower alkyl, trihalomethyl, and halo, or R is $C_1$ to $C_{20}$-aliphatic-O—, or R is unsubstituted or substituted phenyl $C_1$ to $C_{10}$-aliphatic-O— where substituted phenyl has one or more radicals selected from the group consisting of lower alkoxy, lower alkyl, trihalomethyl, and halo;

$R_1$ is -($C_1$ to $C_5$ aliphatic)$R_4$,-($C_1$ to $C_5$ aliphatic)CHO, -($C_1$ to $C_5$ aliphatic)$CH_2OR_8$,—$R_4$, —$CH_2OH$, or CHO;

$R_2$ is H, halo, lower alkyl, lower alkoxy, —CN, —$(CH_2)_n$ $R_4$, —CH(NH$_2$)($R_4$), or —$(CH_2)_n$ $R_9$ where n is 0–5 and where $R_9$ is $-N(R_7)_2$ where each $R_7$ is independently H, or an aliphatic group of 1 to 10 carbon atoms, or acyl of 1–6 carbon atoms, or a cycloalkyl-$(CH_2)_n$- group of 4 to 10 carbons where n is 0–3, or both $R_7$ groups form a ring having 4 to 6 carbons; or $R_3$ is hydrogen, lower alkyl, lower alkoxy, halo, —CN, $R_4$, $NHCONH_2$, or OH;

each $R_4$ group is independently —$COR_5$ where $R_5$ is —OH, a pharmaceutically acceptable ester-forming group —$OR_6$, or —OX where X is a pharmaceutically acceptable cation, or $R_5$ is —$N(R_7)_2$ where each $R_7$ is independently H, or an aliphatic group of 1 to 10 carbon atoms, or a cycloalkyl-$(CH_2)_n$- group of 4 to 10 carbons where n is 0–3, or both $R_7$ groups form a ring having 4 to 6 carbons, or $R_4$ is a sulfonamide, or tetrazol-5-yl; and $R_8$ is hydrogen, $C_1$ to $C_6$ alkyl, or $C_1$ to $C_6$-acyl, excluding those compounds where $R_2$ and $R_3$ are other than hydrogen and are substituted in the 2 and 6 positions.

2. A compound of claim 1 where R is alkoxy of 8 to 15 carbon atoms or unsubstituted or substituted pheny-$C_1$ to $C_{10}$-alkyl-O— where substituted phenyl is substituted with fluoro, trifluoromethyl or methoxy and $R_1$ is $R_4CH=CH—$ or $R_4CH_2CH_2—$.

3. A pharmaceutical composition comprising an effective amount of a compound of formula I according to claim 1 and a pharmaceutically acceptable excipient.

4. The composition of claim 3 for treating psoriasis.

* * * * *